US012582718B2

(12) United States Patent
Li et al.

(10) Patent No.: US 12,582,718 B2
(45) Date of Patent: Mar. 24, 2026

(54) INTEGRIN TARGETING LIGANDS AND USES THEREOF

(71) Applicant: Arrowhead Pharmaceuticals, Inc., Pasadena, CA (US)

(72) Inventors: Zhen Li, Westfield, NJ (US); Jeffrey Carlson, Madison, WI (US); Anthony Nicholas, Oregon, WI (US); Xiaokai Li, Middleton, WI (US); Dongxu Shu, Madison, WI (US); Matthew Fowler-Watters, Madison, WI (US)

(73) Assignee: Arrowhead pharmaceuticals, Inc., Pasadena, CA (US)

( * ) Notice: Subject to any disclaimer, the term of this patent is extended or adjusted under 35 U.S.C. 154(b) by 1356 days.

(21) Appl. No.: 17/078,331

(22) Filed: Oct. 23, 2020

(65) Prior Publication Data

US 2021/0069337 A1 Mar. 11, 2021

Related U.S. Application Data

(63) Continuation of application No. PCT/US2019/029676, filed on Apr. 29, 2019.

(60) Provisional application No. 62/663,763, filed on Apr. 27, 2018.

(51) Int. Cl.

| | |
|---|---|
| ***A61K 47/54*** | (2017.01) |
| ***A61K 47/60*** | (2017.01) |
| ***C07D 401/12*** | (2006.01) |
| ***C07D 403/12*** | (2006.01) |
| ***C07D 471/04*** | (2006.01) |
| ***C12N 15/113*** | (2010.01) |

(52) U.S. Cl.

CPC .......... *A61K 47/545* (2017.08); *A61K 47/549* (2017.08); *A61K 47/60* (2017.08); *C07D 401/12* (2013.01); *C07D 403/12* (2013.01); *C07D 471/04* (2013.01); *C12N 15/1138* (2013.01); *C12N 2310/14* (2013.01); *C12N 2310/351* (2013.01); *C12N 2320/32* (2013.01)

(58) Field of Classification Search

CPC .................................................... A61K 47/545
USPC .......................................................... 540/523
See application file for complete search history.

(56) References Cited

U.S. PATENT DOCUMENTS

| | | | |
|---|---|---|---|
| 4,522,811 A | 6/1985 | Eppstein et al. | |
| 6,117,866 A * | 9/2000 | Bondinell | A61P 43/00 540/523 |
| 6,825,188 B2 * | 11/2004 | Callahan | A61K 45/06 514/212.07 |
| 9,132,188 B2 | 9/2015 | Barbas, III | |
| 2002/0019387 A1 | 2/2002 | Bondinell | |
| 2002/0032187 A1 * | 3/2002 | Drake | C07D 267/14 514/212.07 |
| 2003/0125317 A1 | 7/2003 | Callahan et al. | |
| 2003/0129188 A1 | 7/2003 | Barbas et al. | |

FOREIGN PATENT DOCUMENTS

| | | |
|---|---|---|
| WO | 2006020768 A2 | 2/2006 |
| WO | 2014134255 A2 | 9/2014 |
| WO | 2016196239 A1 | 12/2016 |
| WO | 2019161213 A2 | 8/2019 |

OTHER PUBLICATIONS

Farzan, Valentina M. et al.; "Automated Solid-Phase Click Synthesis of Oligonucleotide Conjugates: From Small Molecules to Diverse N-Acetylgalactosamine Clusters" Bioconjugate Chem.; 28(10); pp. 2599-2607; 2017.
Gavrilyuk et al.; "An efficient chemical approach to bispecific antibodies and antibodies of high valency"; Bioorg. Med. Chem. Lett. 19(14), pp. 3716-3720; 2009.
Li, L-S. et al.; "Chemical adaptor immunotherapy: design, synthesis, and evaluation of novel integrin-targeting devices"; J. Med. Chem.; 47(23); pp. 5630-5640; 2004. and supp. Information to Lian-Sheng Li et al.; J. Med. Chem.; 47(23); pp. 5630-5640; 2004.
Miller, W. H. et al.; "Discovery of orally active nonpeptide vitronectin receptor antagonists based on a 2-benzazepine Gly-Asp mimetic"; J. Med. Chem.; 43(1); pp. 22-26; 2000.
Radar, C. et al.; "Chemically programmed monoclonal antibodies for cancer therapy: Adaptor immunotherapy based on a covalent antibody catalyst"; Proc. Nat. Ac. Sci.; 100(9), pp. 5396-5400; 2003.
Extended European Search Report for corresponding European Patent Application No. 19792933.4 dated Jan. 28, 2022.
Brooks, et al., "Integrin avβ3 Antagonists Promote Tumor Regression by Inducing Apoptosis of Angiogenic Blood Vessels"; 79 Cell 1157-1164 (1994).
Desgrosellier, JS et al., "Integrins in cancer: biological implications and therapeutic opportunities"; Nat Rev Cancer, 10(1):9-22 (2010).
Horton, MA, "The avβ3 Integrin 'vitronectin receptor'"; Int. J. Biochem. Cell Biol.; vol. 29, No. 5, pp. 721-725; 1997.

(Continued)

*Primary Examiner* — Niloofar Rahmani

(74) *Attorney, Agent, or Firm* — Paul VanderVelde; Meibo Chen; Mitchell Porter

(57) ABSTRACT

Compounds having affinity for integrins, the synthesis of these compounds, and the use of these compounds as ligands to facilitate the delivery of cargo molecules to cells expressing integrins are described. The described integrin targeting ligands have serum stability and affinity for αvβ3 integrin and/or αvβ5 integrin, and are suitable for conjugation to cargo molecules, such as such as oligonucleotide-based therapeutic agents (e.g., RNAi agents), to facilitate delivery of the cargo molecules to cells and tissues, such as tumor cells, that express integrin αvβ3, integrin αvβ5, or both integrin αvβ3 and integrin αvβ5. Compositions that include integrin targeting ligands and methods of use are also described.

10 Claims, No Drawings

Specification includes a Sequence Listing.

(56) References Cited

OTHER PUBLICATIONS

Kapp T. et al.; "A Comprehensive Evaluation of the Activity and Selectivity Profile of Ligands for RGD-binding Integrins"; Nature Scientific Reports; vol. 7; 1-13; 2017.

Ley, et al., "Integrin-based therapeutics: biological basis, clinical use and new drugs"; 15(3) Nat. Rev. Drug Discov.; vol. 15; pp. 173-183 (2016).

Mas-Moruno, et al., "Cilengitide: The First Anti-Angiogenic Small Molecule Drug Candidate. Design, Synthesis and Clinical Evaluation"; Anticancer Agents Med Chem, 10:753-768; 2010.

Wallace, et al., "Multi-Kiloscale Enantioselective Synthesis of a Vitronectin Receptor Antagonist", Organic Process Research & Development; vol. 8; pp. 738-743; (2004).

Zajac, et al., "An Application of Borane as a Protecting Group for Pyridine"; J. Org. Chem.; vol. 73; p. 6901; 2008.

* cited by examiner

SEQUENCE LISTING

```
<160> NUMBER OF SEQ ID NOS: 9

<210> SEQ ID NO 1
<211> LENGTH: 21
<212> TYPE: RNA
<213> ORGANISM: Homo sapiens
<220> FEATURE:
<223> OTHER INFORMATION: RNAi agent antisense strand modified sequence

<400> SEQUENCE: 1

uuucaugaaa ucguuacguu g                                              21


<210> SEQ ID NO 2
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 2

caacguaacg auuucaugaa a                                              21


<210> SEQ ID NO 3
<211> LENGTH: 21
<212> TYPE: RNA
<213> ORGANISM: Artificial sequence
<220> FEATURE:
```

-continued

<223> OTHER INFORMATION: RNAi agent sense strand modified sequence

<400> SEQUENCE: 3
caacguaacg auuucaugaa a 21

<210> SEQ ID NO 4
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 4
caacguaacg auuucaugaa a 21

<210> SEQ ID NO 5
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 5
caacguaacg auuucaugaa a 21

<210> SEQ ID NO 6
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 6
caacguaacg auuucaugaa a 21

<210> SEQ ID NO 7
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 7
caacguaacg auuucaugaa a 21

<210> SEQ ID NO 8
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 8
caacguaacg auuucaugaa a 21

<210> SEQ ID NO 9
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 9
caacguaacg auuucaugaa a 21

INTEGRIN TARGETING LIGANDS AND USES THEREOF

CROSS REFERENCE TO RELATED APPLICATIONS

This application is a continuation of International Patent Application No. PCT/US19/29676, filed on Apr. 29, 2019 which claims priority to U.S. Provisional Patent Application No. 62/663,763, filed on Apr. 27, 2018, the entirety of each of which are incorporated by reference herein.

FIELD OF INVENTION

Disclosed herein are compounds that have affinity for integrins, methods of synthesis of such compounds, and the use of such compounds as ligands to deliver cargo molecules in vivo.

BACKGROUND

Integrins are transmembrane glycoproteins that mediate cell-cell and cell-matrix interactions. The integrins alpha-v beta-3 (αvβ3) and alpha-v beta-5 (αvβ5) are members of the integrin superfamily of adhesion molecules and are known for being receptors for the extracellular matrix (ECM) protein vitronectin. (Horton, M A, 29(5) *Int. J. Biochem. Cell Biol.* 721-725 (1997)). Altered expression of certain integrins, including integrin αvβ3 and integrin αvβ5, are believed to contribute to tumor progression, invasiveness, and metastases.

Indeed, overexpression of integrins, including integrins αvβ3 and αvβ5, have been reported in many tumor cells. (Desgrosellier, J S et al., Nat Rev Cancer, 10(1):9-22 (2010)). Antagonists of αvβ3 (and to a lesser extent αvβ5) have been considered for use in a variety of diseases associated with altered integrin function. For example, attempts have been made to develop αvβ3 inhibitors as potential cancer treatments, as the inhibition of the αvβ3 receptor has been shown to inhibit angiogenesis, thereby preventing the formation of new blood vessels which are believed to be necessary for tumor growth. (See, e.g., Brooks et al., 79 *Cell* 1157-1164 (1994); Mas-Moruno et al., Anticancer Agents Med Chem, 10(10):753-768). However, one leading example of an αvβ3 inhibitor, the antagonist Cilengitide, was shown to be non-efficacious in clinical trials aimed at limiting tumor angiogenesis and progression in patients with glioblastoma. (See, e.g., Ley et al., *Integrin-based Therapeutics: Biological Basis, Clinical Use and New Drugs,* 15(3) Nat. Rev. Drug Discov. 173-183 (2016)).

In general, the delivery of cargo molecules in vivo, including therapeutically effective pharmaceutical compounds or active pharmaceutical ingredients, to desired cells and/or tissues, continues to be a general challenge in the development of therapeutically viable drug products. There continues to exist a need for stable and effective targeting compounds that have affinity for and/or are able to selectively bind to specific cells and tissues, which can be utilized or employed as ligands to facilitate the delivery of therapeutic cargo molecules to those specific cells or tissues. Moreover, there exists a specific need for compounds that are capable of selectively targeting integrin alpha-v beta-3 and which are suitable to be conjugated to cargo molecules and deliver the cargo molecules to cells expressing such integrins, such as tumor cells, in vivo. For oligonucleotides and oligonucleotide-based therapeutics in particular (e.g., an oligonucleotide-based compound such as an antisense oligonucleotide or an RNAi agent), there continues to exist a need for ligands that are able to target integrin alpha-v beta-3 and/or integrin alpha-v beta-5 and facilitate the delivery of these oligonucleotide-based compounds to cells expressing such integrins.

SUMMARY

Described herein are compounds that have affinity for certain integrins, including αvβ3 and αvβ5, which can be employed as ligands (referred to herein as "integrin targeting ligands," "αvβ3 integrin targeting ligands," "αvβ3 integrin ligands," or simply "integrin ligands") to selectively direct compounds or other molecules to which they are attached to cells or tissues that express integrin αvβ3 and/or αvβ5. The integrin targeting ligands disclosed herein are stable in serum and have affinity for, and can bind with specificity to, these integrins. The integrin targeting ligands disclosed herein can be conjugated to cargo molecule(s) to facilitate the delivery of the cargo molecule(s) to cells or tissues that express integrin αvβ3 and/or αv5.

In another aspect, described herein are methods of delivering a cargo molecule to a tissue and/or cell expressing integrin αvβ3 and/or integrin αvβ5 in vivo, wherein the methods include administering to a subject one or more integrin targeting ligands disclosed herein that has been conjugated to one or more cargo molecules. Further disclosed herein are methods of treatment of a subject having a disease, symptom, or disorder for which the delivery of a therapeutic cargo molecule (e.g., an active pharmaceutical ingredient) to a cell expressing αvβ3 integrin and/or αvβ5 integrin is capable of treating the subject, wherein the methods include administering to a subject one or more integrin targeting ligands disclosed herein that has been conjugated to one or more therapeutic cargo molecules.

Further described herein are methods of inhibiting expression of a target gene in a cell in vitro or in vivo, wherein the methods include administering to the cell an effective amount of a conjugate that includes one or more integrin targeting ligands disclosed herein that have been conjugated to one or more oligonucleotide-based therapeutics, such as an RNAi agent, that are capable of inhibiting expression of a target gene in a cell. In some embodiments, described herein are methods of inhibiting expression of a target gene in a cell of a subject, wherein the subject is administered an effective amount of one or more oligonucleotide-based therapeutics (such as an RNAi agent) that has been conjugated to one or more integrin targeting ligands disclosed herein.

In yet another aspect, described herein are compositions that include the integrin targeting ligands disclosed herein. The compositions described herein can be pharmaceutical compositions or medicaments that include one or more integrin targeting ligands disclosed herein conjugated to one or more therapeutic cargo molecules, such as an RNAi agent or other cargo molecule or therapeutic substance.

In some embodiments, described herein are methods of treatment of a subject having a disease or disorder mediated at least in part by expression of a target gene in a cell that expresses integrin αvβ3, wherein the methods include administering to a subject in need thereof an effective amount of a pharmaceutical composition, wherein the pharmaceutical composition includes one or more oligonucleotide-based therapeutics capable of inhibiting expression of a targeted gene, such as an RNAi agent, that is conjugated to one or more integrin targeting ligands disclosed herein. In some embodiments, described herein are methods of treatment of a subject having a disease or disorder mediated at least in part by expression of a target gene in a tumor cell, wherein the methods include administering to a subject in need thereof an effective amount of a pharmaceutical composition, wherein the pharmaceutical composition includes one or more oligonucleotide-based therapeutics capable of inhibiting expression of a targeted gene, such as an RNAi agent, conjugated to one or more integrin targeting ligands disclosed herein. In some embodiments, described herein are methods of treatment of a subject having a disease or disorder mediated at least in part by expression of a target gene in a kidney tumor cell, such as a clear cell renal carcinoma tumor cell, wherein the methods include administering to a subject in need thereof an effective amount of a pharmaceutical composition, wherein the pharmaceutical composition includes one or more oligonucleotide-based therapeutics capable of inhibiting expression of a targeted gene, such as an RNAi agent, conjugated to one or more integrin targeting ligands disclosed herein.

In a first aspect, this disclosure provides synthetic integrin targeting ligands.

In some embodiments, an integrin targeting ligand disclosed herein includes the structure of the following formula:

(Formula I)

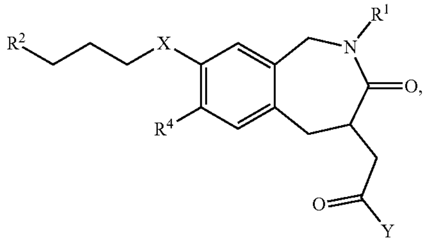

wherein,

X is O, $NR^3$, or S;

Y is $OR^3$, $N(R^3)_2$, or $SR^3$ $R^1$ is optionally substituted alkyl or $R^1$ comprises a cargo molecule;

$R^2$ is $NR^3R^5$ or optionally substituted heteroalkyl;

each instance of $R^3$ is independently H or optionally substituted alkyl;

$R^4$ is H, optionally substituted alkyl, optionally substituted alkoxy, or $R^4$ comprises a cargo molecule;

$R^5$ is optionally substituted aryl, optionally substituted heteroaryl, optionally substituted heterocyclyl, guanidinyl, or $R^2$ comprises a cargo molecule;

and at least one of $R^1$, $R^2$, or $R^4$ comprises a cargo molecule.

In some embodiments, an integrin targeting ligand disclosed herein includes the structure of Formula I, wherein $R^2$ is $NHR^5$, and $R^5$ is selected from the group consisting of

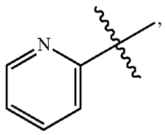,
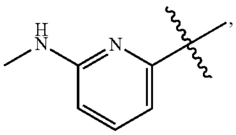,

-continued

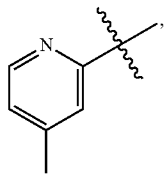,
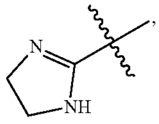,
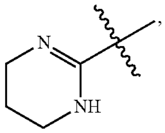,
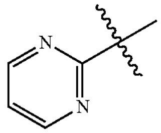

and

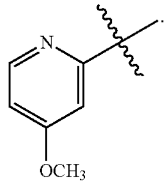.

In some embodiments, an integrin targeting ligand disclosed herein includes the structure of Formula I, wherein $R^2$ is:

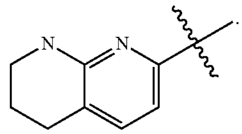 [SMILES: *c1ccc2c(n1)NCCC2].

Any of the integrin targeting ligands disclosed herein can be linked to a cargo molecule, a reactive group, and/or a protected reactive group. Linking to a reactive group, for example, can be used to facilitate conjugation of the integrin targeting ligand to a cargo molecule. The integrin targeting ligands disclosed herein can increase targeting of a cargo molecule to a cell expressing an integrin, including αvβ3 integrin and/or αvβ5 integrin. A cargo molecule can be, but is not limited to, a pharmaceutically active ingredient or compound, a prodrug, or another substance with known therapeutic benefit. In some embodiments, a cargo molecule can be, but is not limited to, a small molecule, an antibody, an antibody fragment, an immunoglobulin, a monoclonal antibody, a label or marker, a lipid, a natural or modified oligonucleotide, a modified oligonucleotide-based compound (e.g., an antisense oligonucleotide or an RNAi agent), a natural or modified nucleic acid, a peptide, an aptamer, a polymer, a polyamine, a protein, a toxin, a vitamin, a polyethylene glycol, a hapten, a digoxigenin, a biotin, a radioactive atom or molecule, or a fluorophore. In some embodiments, a cargo molecule includes a pharmaceutically active ingredient or a prodrug. In some embodiments, a cargo molecule is or includes an oligonucleotide-based therapeutic, such as an antisense compound or an RNAi agent. In some embodiments, a cargo molecule is or includes an oligonucleotide-based compound that is a pharmaceutically active ingredient. In some embodiments, a cargo molecule is or includes an RNAi agent that is a pharmaceutically active ingredient.

Described herein is the use of the described αvβ3/5 integrin targeting ligands to target and deliver a cargo molecule to a cell that expresses integrins. The cargo molecule can be delivered to a cell in vitro, in situ, ex vivo, or in vivo.

In another aspect, this disclosure provides compositions that include one or more of the integrin targeting ligands described herein. For example, in some embodiments, compositions comprising one or more integrin targeting ligands disclosed herein include one or more oligonucleotide-based compounds, such as one or more RNAi agents, to be delivered to a cell in vivo. In some embodiments, described herein are compositions for delivering an RNAi agent to a cell in vivo, wherein the RNAi agent is linked to one or more integrin targeting ligands.

Compositions that include one or more integrin targeting ligands are described. In some embodiments, a composition comprises a pharmaceutically acceptable excipient. In some embodiments, a composition that includes one or more integrin targeting ligands comprises one or more other pharmaceutical substances or pharmaceutically active ingredients or compounds. In some embodiments, medicaments that include one or more integrin targeting ligands are described herein.

Compositions that include one or more integrin targeting ligands disclosed herein can be delivered in vivo or in vitro to various cancer cells, including for example, clear cell renal carcinoma tumor cells (e.g., A498), other kidney cancer cells (e.g., ACHN, CAKI-2, 769-P, 786-O), melanoma cells (e.g., A375), glioblastoma cells (e.g., U87 MG), pancreatic cancer cells (e.g., (PANC-1), lung cancer cells (e.g., H460, H661, H1573, H2126), colon cancer cells (e.g., HT29, HCT116), liver cancer cells (e.g., Hep2G, Hep3B), breast cancer cells (e.g., MCF7, SK-BR3), prostate cancer cells (e.g., DU145, PC3, LNCaP, MDA-PCa-2b), oral cancer cells (e.g., KB), tongue cancer cells (e.g., CAL27, SCC9), pharynx cancer cells (e.g., Detroit562), and/or ovarian cancer cells (e.g., OVCAR3, SKOV3, A2780) and/or other patient derived xenografts.

In another aspect, the present disclosure provides methods that include the use of one or more integrin targeting ligands and/or compositions as described herein and, if desired, bringing the disclosed integrin targeting ligands and/or compositions into a form suitable for administration as a pharmaceutical product. In other embodiments, the disclosure provides methods for the manufacture of the ligands and compositions, e.g., medicaments, described herein.

Compositions that include one or more integrin targeting ligands can be administered to subjects in vivo using routes of administration known in the art to be suitable for such administration in view of the cargo molecule sought to be administered, including, for example, subcutaneous, intravenous, intratumoral, inhaled (aerosol or dry powder formulations), intranasal, intraperitoneal, intradermal, transdermal, oral, sublingual, or topical administration. In some embodiments, the compositions that include one or more integrin targeting ligands may be administered for systemic delivery, for example, by intravenous or subcutaneous administration.

In some embodiments, disclosed herein are methods for delivering one or more desired cargo molecule(s) to a clear cell renal carcinoma tumor cell in vivo, wherein the methods include administering to the subject one or more integrin targeting ligands conjugated to one or more cargo molecules.

In some embodiments, disclosed herein are methods of delivering an oligonucleotide-based compound to a tumor cell in vivo, wherein the methods include administering to the subject one or more integrin targeting ligands conjugated to the one or more oligonucleotide-based compounds. In some embodiments, disclosed herein are methods of delivering an RNAi agent to a tumor cell in vivo, wherein the methods include administering to the subject one or more integrin targeting ligands conjugated to the one or more RNAi agents. In some embodiments, disclosed herein are methods of inhibiting the expression of a target gene in a clear cell renal carcinoma tumor cell in vivo, wherein the methods include administering to the subject an RNAi agent conjugated to one or more ligands having affinity for αvβ3 integrin and/or αvβ5 integrin.

Other objects, features, aspects, and advantages of the invention will be apparent from the following detailed description and from the claims.

DETAILED DESCRIPTION

Integrin Targeting Ligands

Described herein are compounds that have affinity for integrins, exhibit serum stability in vivo, and can be used as ligands to facilitate the delivery of cargo molecules to cells and/or tissues that express integrins, such as integrin αvβ3 and/or integrin αvβ5. The integrin targeting ligands can be used to target cells that express integrins in vitro, in situ, ex vivo, and/or in vivo.

In some embodiments, the integrin targeting ligands disclosed herein can be conjugated to one or more cargo molecules to preferentially direct and target the cargo molecules to cells or tissues that express integrins, including integrin αvβ3 and/or integrin αvβ5. In some embodiments, the cargo molecules include or consist of pharmaceutically active compounds. In some embodiments, the cargo molecules include or consist of oligonucleotide-based compounds, such as RNAi agents. In some embodiments, the integrin targeting ligands disclosed herein are conjugated to cargo molecules to direct the cargo molecules to tumor cells in vivo. In some embodiments, the integrin targeting ligands disclosed herein are conjugated to cargo molecules to direct the cargo molecules to clear cell renal carcinoma tumor cells in vivo.

Formula I

In one aspect, the invention provides integrin ligands of the structure:

(Formula I)

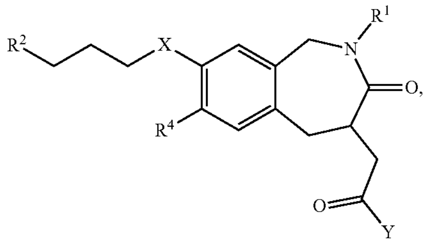

wherein,

X is O, $NR^3$, or S;

Y is $OR^3$, $N(R^3)_2$, or $SR^3$ $R^1$ is optionally substituted alkyl or R comprises a cargo molecule;

$R^2$ is $NR^3R^5$ or optionally substituted heteroalkyl;

each instance of $R^3$ is independently H or optionally substituted alkyl;

$R^4$ is H, optionally substituted alkyl, optionally substituted alkoxy, or $R^4$ comprises a cargo molecule;

$R^5$ is optionally substituted aryl, optionally substituted heteroaryl, optionally substituted heterocyclyl, guanidinyl, or $R^2$ comprises a cargo molecule;

and at least one of $R^1$, $R^2$, or $R^4$ comprises a cargo molecule.

In some embodiments of Formula I, $R^2$ is $NHR^5$, and $R^5$ is selected from the group consisting of:

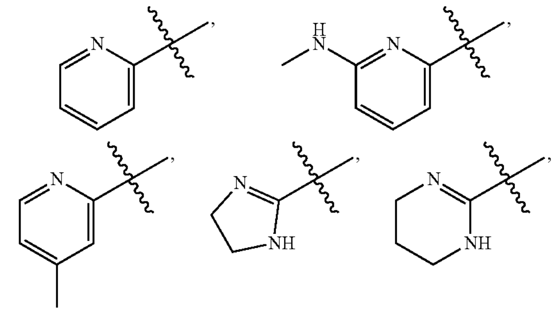

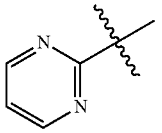

and

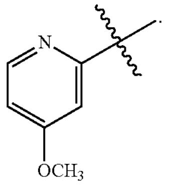

In some embodiments, an integrin targeting ligand disclosed herein includes the structure of Formula I, wherein $R^2$ is:

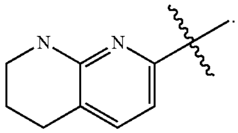 [SMILES: *c1ccc2c(n1)NCCC2]

Integrin Targeting Ligand Precursors

In some embodiments, the invention provides integrin targeting ligand precursors which can be used to attach an integrin targeting ligand to a moiety comprising a cargo molecule. Provided herein are integrin targeting ligand precursors of the formula:

(Formula Ip)

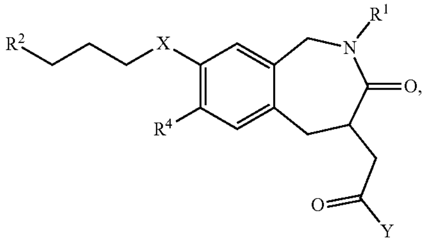

wherein,

X is O, $NR^3$, or S;

Y is $OR^3$, $N(R^3)_2$, or $SR^3$ $R^1$ is optionally substituted alkyl or R comprises a cargo molecule;

$R^2$ is $NR^3R^5$ or optionally substituted heteroalkyl;

each instance of $R^3$ is independently H or optionally substituted alkyl;

$R^4$ is H, optionally substituted alkyl, optionally substituted alkoxy, or $R^4$ comprises a cargo molecule;

$R^5$ is optionally substituted aryl, optionally substituted heteroaryl, optionally substituted heterocyclyl, guanidinyl, or $R^2$ comprises a cargo molecule;

and at least one of $R^1$, $R^2$, or $R^4$ comprises a reactive group.

In some embodiments of compounds of Formula Ip, the reactive group comprises an azide.

Compounds of Formula I

In some embodiments, the integrin targeting ligands disclosed herein have structures that include, consist of, or consist essentially of, any of the structures represented by the following:

(Structure 4.1a)

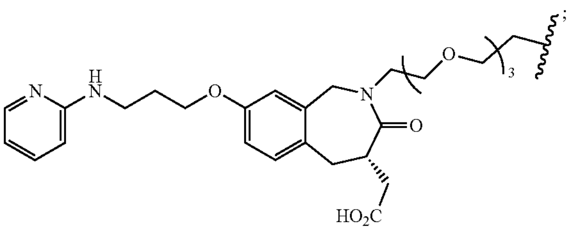

(Structure 4.2a)

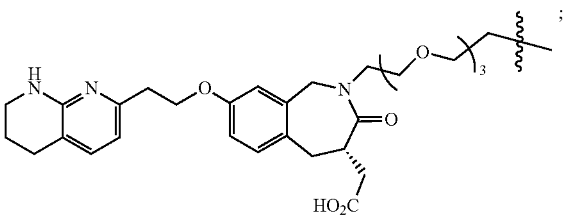

(Structure 4.3a)

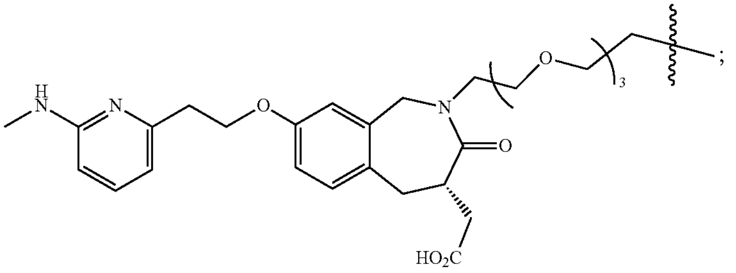

-continued
(Structure 4.4a)
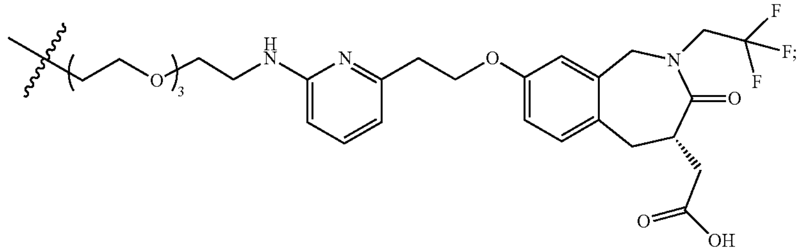
(Structure 4.5a)
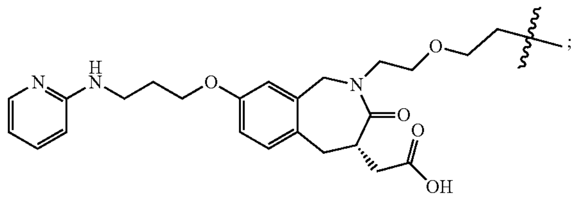
(Structure 4.6a)
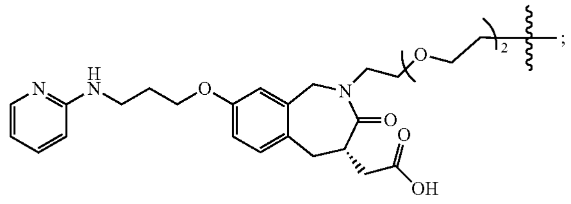
(Structure 4.8a)
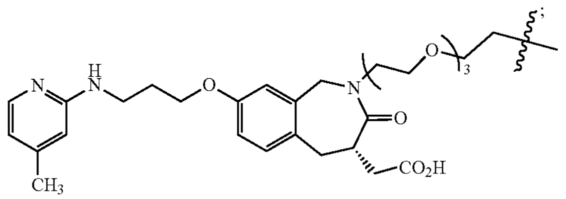
(Structure 4.9a)
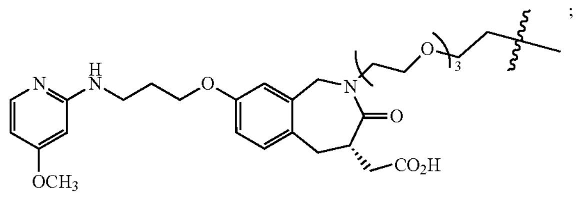
(Structure 4.10a)
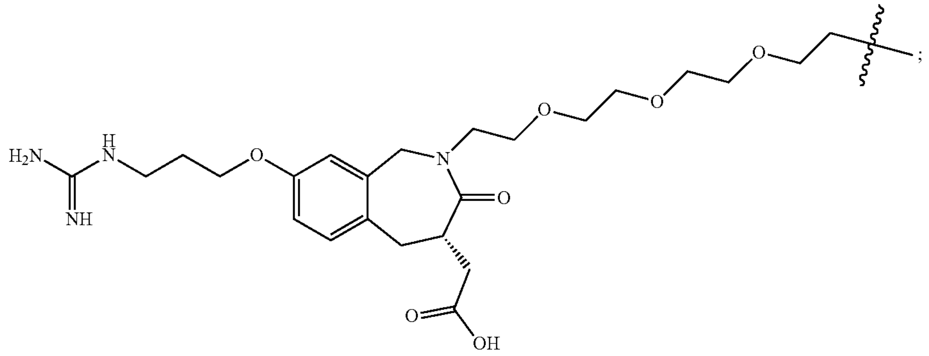
(Structure 4.11a)
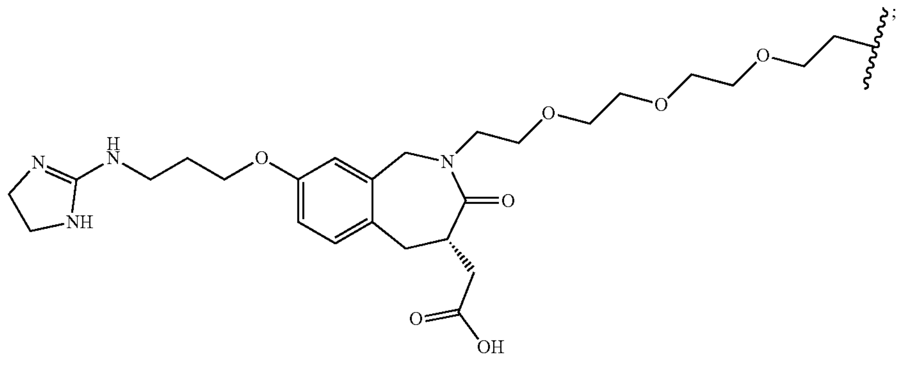

-continued (Structure 4.12a)

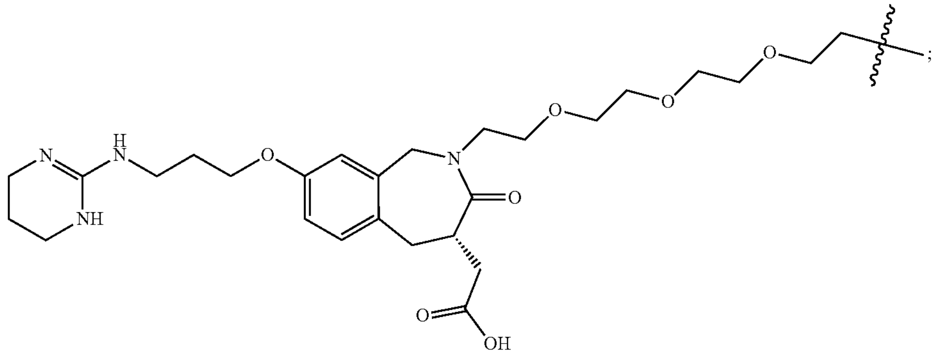

(Structure 4.13a)

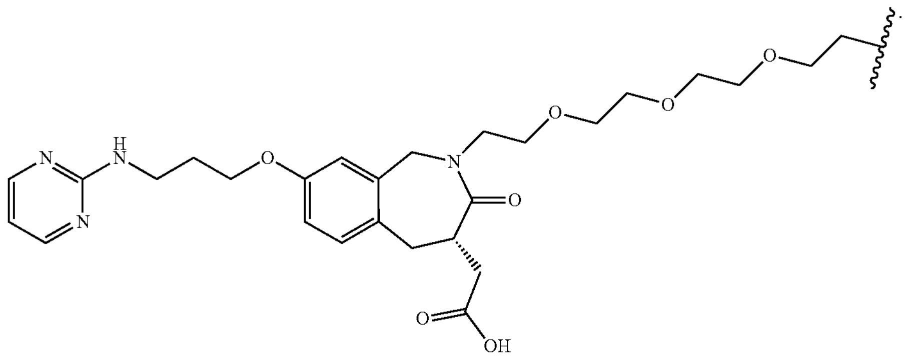

In some embodiments, an integrin targeting ligand disclosed herein can be conjugated to one or more (e.g., 2, 3, 4, 5, 6, 7, 8, 9, 10; or 1 to 10, 2 to 10, 1 to 9, 1 to 8, 1 to 7, 1 to 6, 1 to 5, 1 to 4, 1 to 3, 1 to 2, 2 to 10, 3 to 10, 4 to 10, 5 to 10, 2 to 5, 2 to 4, or 3 to 5) cargo molecules (e.g., any of the cargo molecules described herein or known in the art).

In some embodiments, more than one integrin targeting ligand disclosed herein (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30 integrin targeting ligands) can be conjugated to one cargo molecule (e.g., any of the cargo molecules described herein or known in the art).

In some embodiments, the integrin targeting ligands disclosed herein are optionally conjugated to one or more cargo molecules via a linking group, such as, for example, a polyethylene glycol (PEG) group.

In some embodiments, the integrin targeting ligands disclosed herein are optionally conjugated to one or more cargo molecules via a scaffold that includes at least one attachment point for each ligand and at least one attachment point for each cargo molecule. In some embodiments, the integrin targeting ligands comprise, consist of, or consist essentially of, an integrin targeting ligand conjugated to one cargo molecule. In some embodiments, the integrin targeting ligands comprise, consist of, or consist essentially of, an integrin targeting ligand conjugated to more than one cargo molecule.

In some embodiments, the integrin targeting ligand comprises, consists of, or consists essentially of, any of Structure 4.1a, Structure 4.2a, Structure 4.3a, Structure 4.4a, Structure 4.5a, Structure 4.6a, Structure 4.8a, Structure 4.9a, Structure 4.10a, Structure 4.11a, Structure 4.12a, Structure 4.13a, each as disclosed herein.

In some embodiments, an integrin targeting ligand disclosed herein comprises the following structure:

(Structure 4.1a)

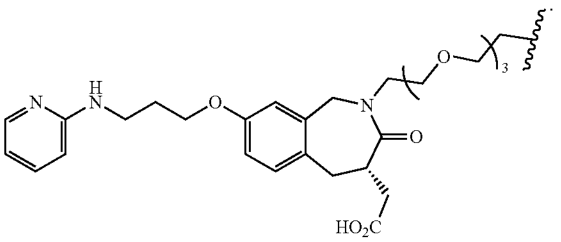

In some embodiments, the integrin targeting ligand of Structure 4a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.1b)

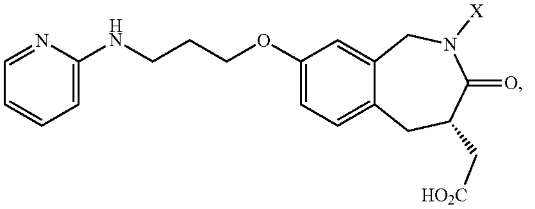

wherein X includes a reactive group, a protected reactive group, or a cargo molecule (e.g., an RNAi agent).

In some embodiments, the integrin targeting ligand precursor can be synthesized to include an azide reactive group and comprises the following structure:

(Structure 4.1c)

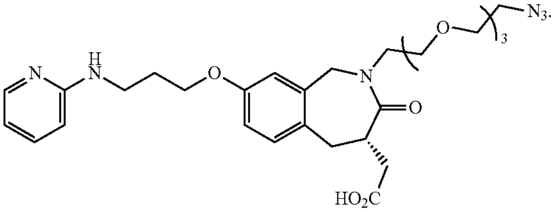

In some embodiments, an integrin targeting ligand disclosed herein comprises the following structure:

(Structure 4.2a)

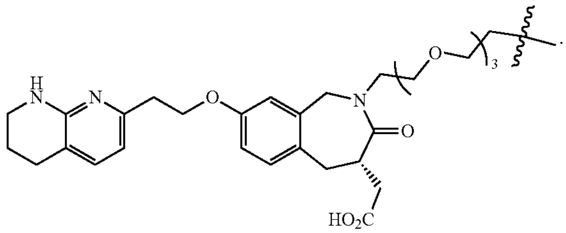

In some embodiments, the integrin targeting ligand of Structure 4.2a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.2b)

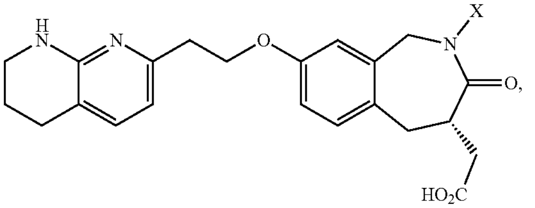

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.2c)

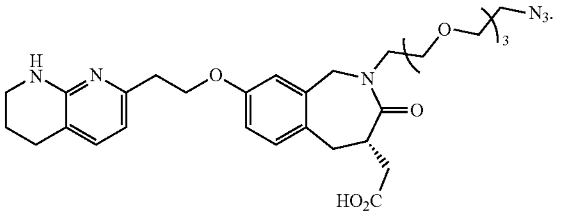

In some embodiments, an integrin targeting ligand disclosed herein comprises the following structure:

(Structure 4.3a)

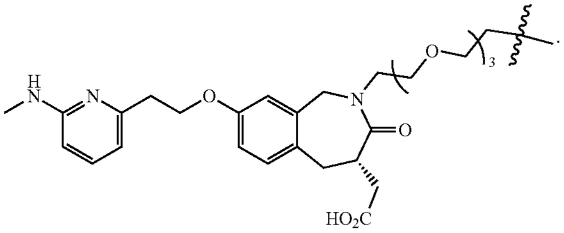

In some embodiments, the integrin targeting ligand of Structure 4.3a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.3b)

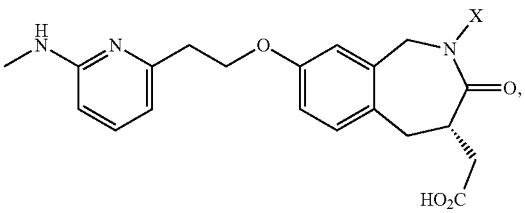

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.3c)

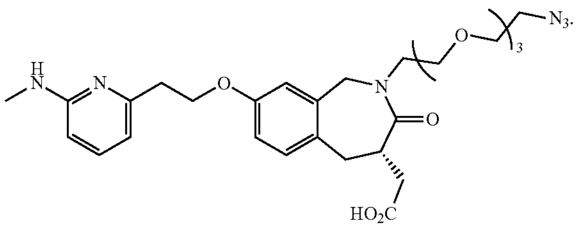

In some embodiments, an integrin targeting ligand disclosed herein comprises the following structure:

(Structure 4.4a)

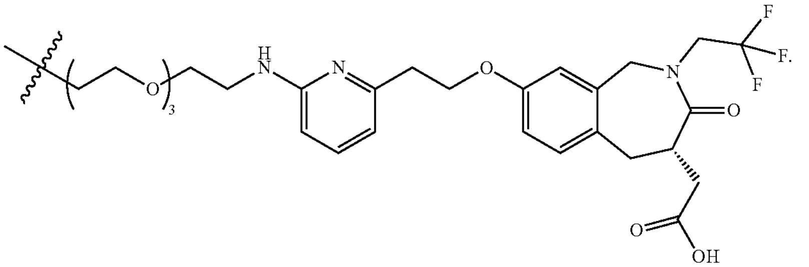

In some embodiments, the integrin targeting ligand of Structure 4.4a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.4b)

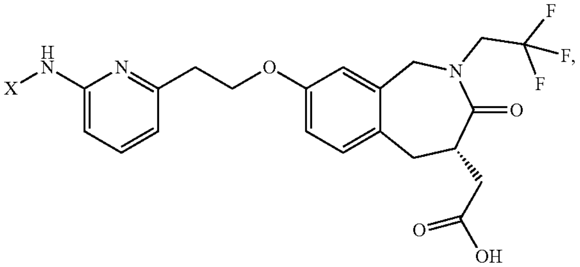

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.4c)

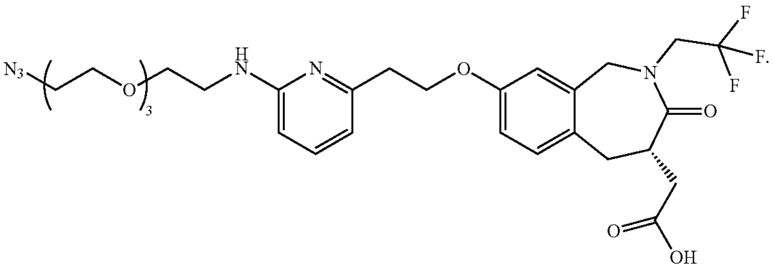

In some embodiments, an integrin targeting ligand disclosed herein comprises the following structure:

(Structure 4.5a)

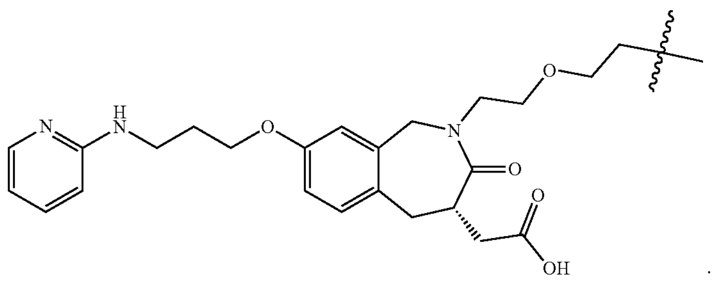

In some embodiments, the integrin targeting ligand of Structure 4.5a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.5b)

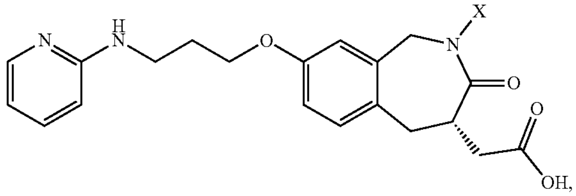

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.5c)

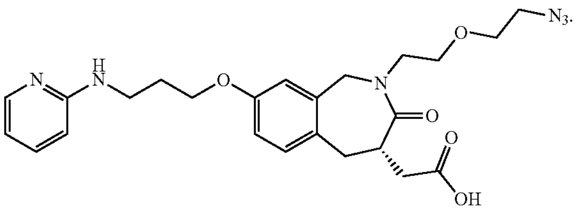

In some embodiments, an integrin targeting ligand disclosed herein comprises the following structure:

(Structure 4.6a)

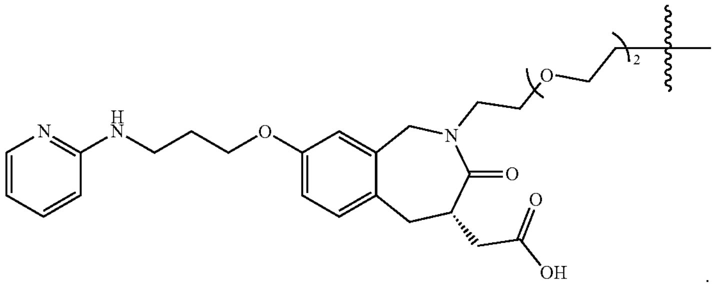

In some embodiments, the integrin targeting ligand of Structure 4.6a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.6b)

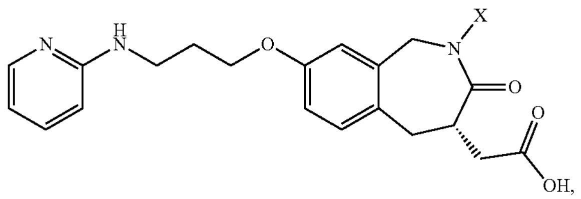

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.6c)

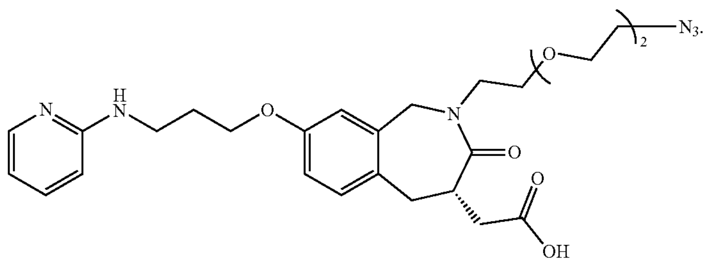

In some embodiments, an integrin targeting ligand disclosed herein comprises the following structure:

(Structure 4.8a)

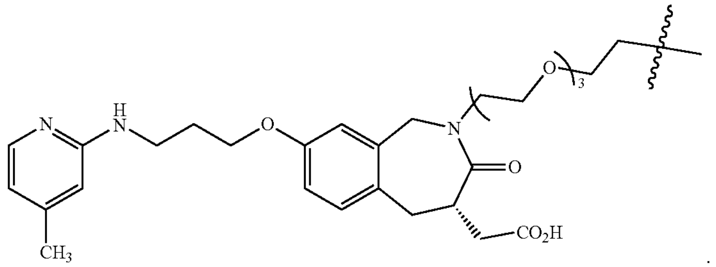

In some embodiments, the integrin targeting ligand of Structure 4.8a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.8b)

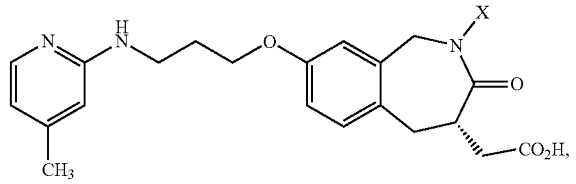

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.8c)

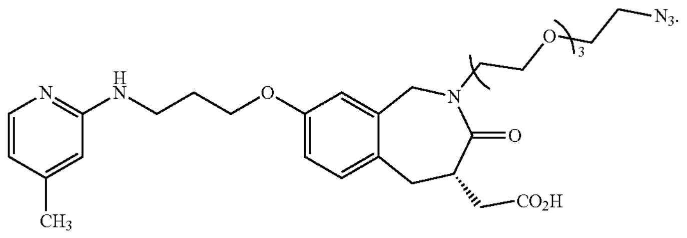

In some embodiments, an integrin targeting ligand disclosed herein comprises the following structure:

(Structure 4.9a)

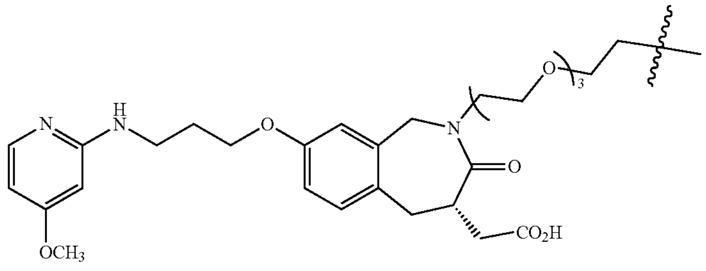

In some embodiments, the integrin targeting ligand of Structure 4.9a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.9b)

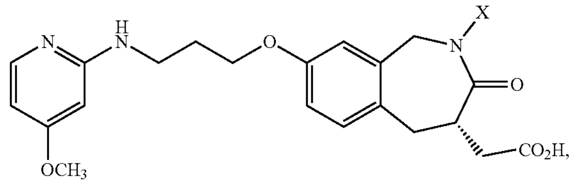

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.9c)

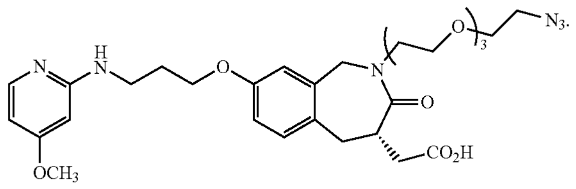

In some embodiments, an integrin targeting ligand disclosed herein comprises the following structure:

(Structure 4.10a)

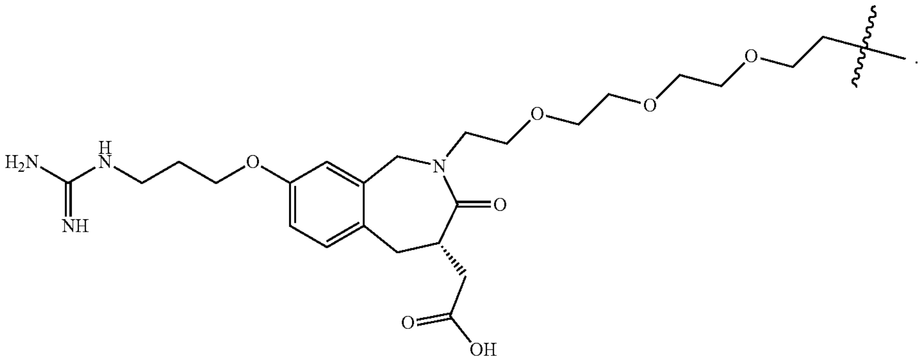

In some embodiments, the integrin targeting ligand of Structure 4.10a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.10b)

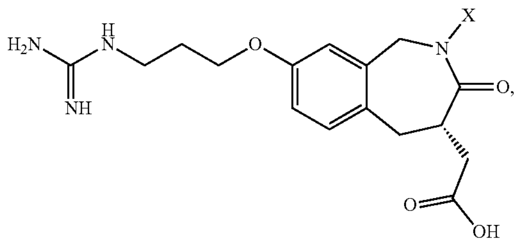

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.10c)

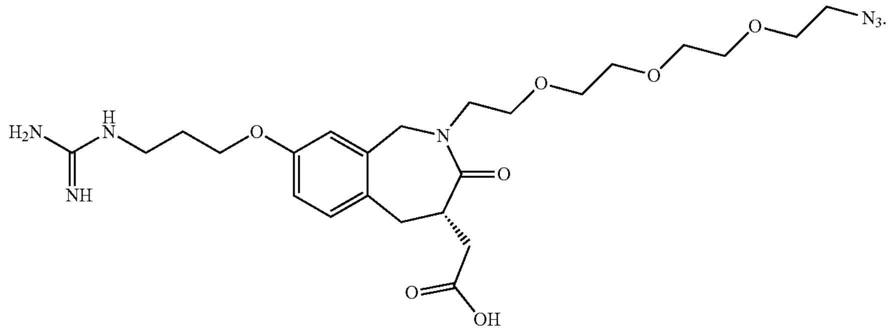

In some embodiments, an integrin targeting ligand disclosed herein comprises the following structure:

(Structure 4.11a)

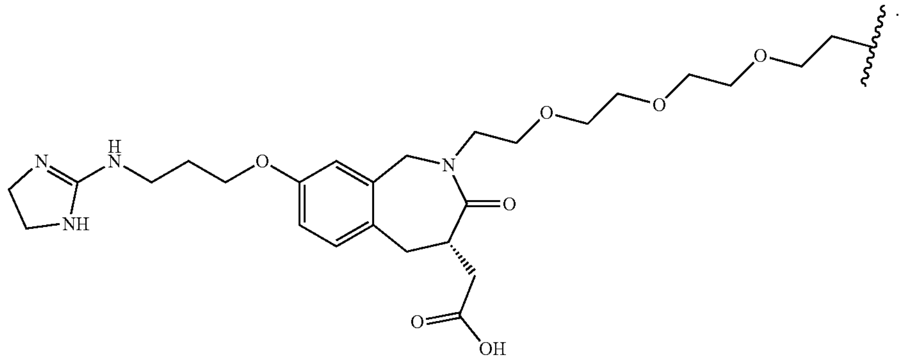

In some embodiments, the integrin targeting ligand of Structure 4.11a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.11b)

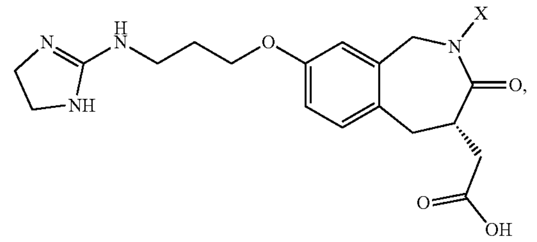

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.11c)

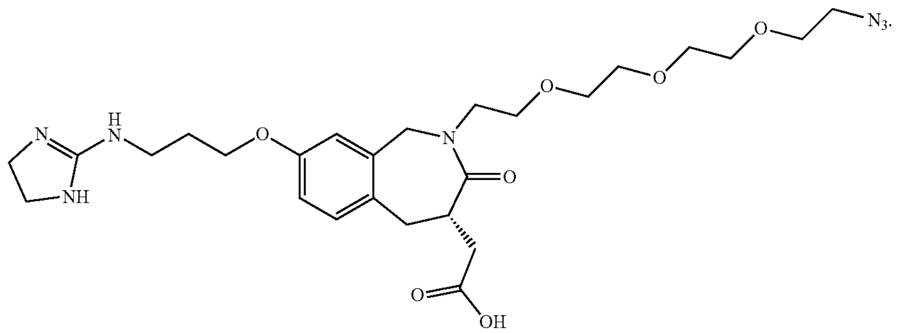

In some embodiments, an integrin targeting ligand disclosed herein comprises the following structure:

(Structure 4.12a)

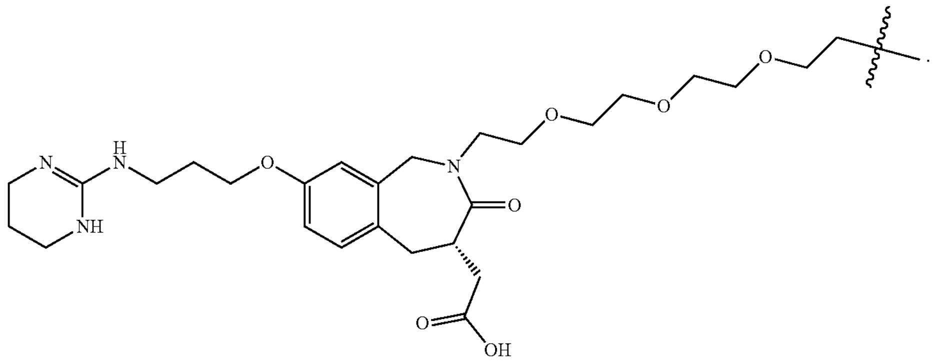

In some embodiments, the integrin targeting ligand of Structure 4.12a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.12b)

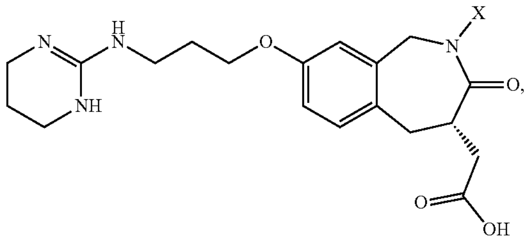

wherein X includes a reactive group, a protected reactive group, or a cargo molecule (e.g., an RNAi agent).

In some embodiments, the integrin targeting ligand precursor can be synthesized to include an azide reactive group, and comprises the following structure:

(Structure 4.12c)

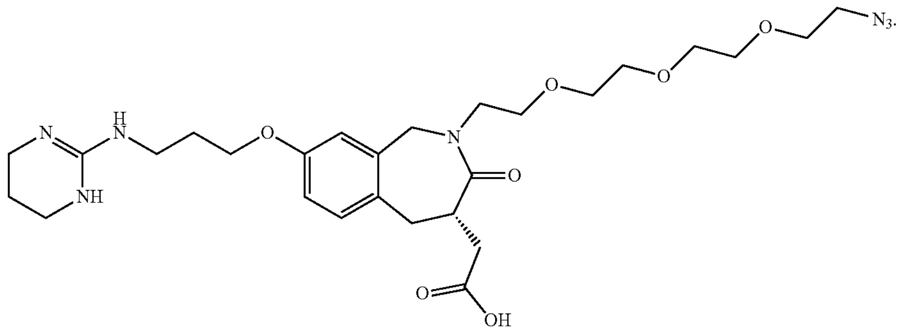

In some embodiments, an integrin targeting ligand disclosed herein comprises the following structure:

(Structure 4.13a)

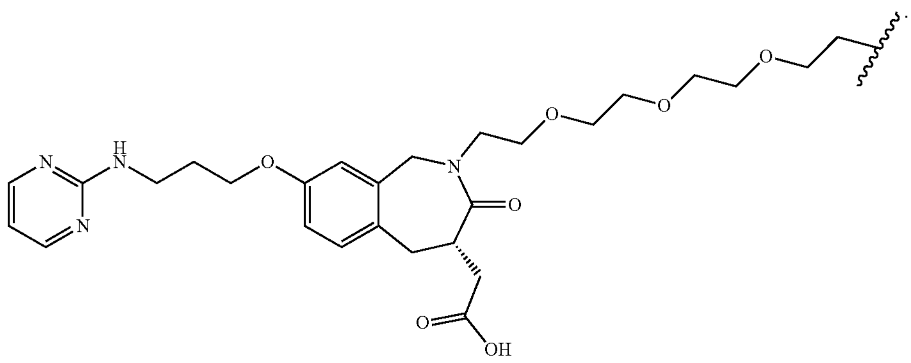

In some embodiments, the integrin targeting ligand of Structure 4.13a is linked to one or more cargo molecules (e.g., RNAi agent(s)).

In some embodiments, the integrin targeting ligand can be synthesized to include a reactive group, a protected reactive group, or a cargo molecule, and comprises the following structure:

(Structure 4.13b)

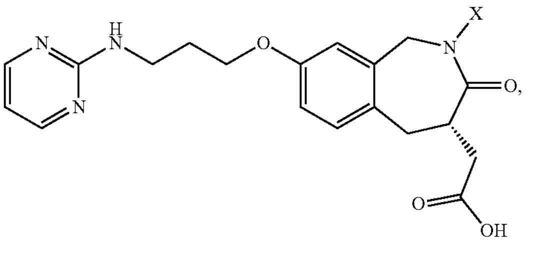

wherein X includes a reactive group, a protected reactive group, or a cargo molecule (e.g., an RNAi agent).

In some embodiments, the integrin targeting ligand precursor can be synthesized to include an azide reactive group, and comprises the following structure:

Non-limiting examples of cycloalkyl groups include, but are not limited to, cyclopropyl, methyl-cyclopropyl, 2,2-dimethyl-cyclobutyl, 2-ethyl-cyclopentyl, and cyclohexyl. Cycloalkyls may include multiple spiro- or fused rings. Cycloalkyl groups are optionally mono-, di-, tri-, tetra-, or penta-substituted on any position as permitted by normal valency.

As used herein, the term "alkenyl" refers to a non-aromatic hydrocarbon radical, straight, or branched, containing at least one carbon-carbon double bond, and having from 2 to 10 carbon atoms unless otherwise specified. Up to five carbon-carbon double bonds may be present in such groups. For example, "$C_2$-$C_6$" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least (Structure 4.13c)

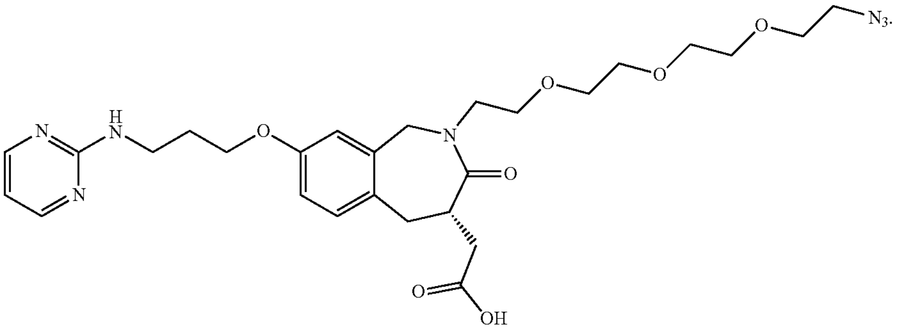

one carbon-carbon triple bond. Up to 5 carbon-carbon triple bonds may be present. Thus, "$C_2$-$C_6$ alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may be optionally mono-, di-, tri-, tetra-, or penta-substituted on any position as permitted by normal valency.

The azide reactive group as disclosed in any of Structure 4.1c, Structure 4.2c, Structure 4.3c, Structure 4.4c, Structure 4.5c, Structure 4.6c, Structure 4.8c, Structure 4.9c, Structure 4.10c, Structure 4.11c, Structure 4.12c, and Structure 4.13c can be used to attach the integrin targeting ligand to a molecule of interest, i.e., to a cargo molecule such as an RNAi agent. The cargo molecule can be any molecule that is desired to be targeted to an integrin-expressing cell.

As used herein, the term "alkyl" refers to a saturated aliphatic hydrocarbon group, straight chain or branched, having from 1 to 10 carbon atoms unless otherwise specified. For example, "$C_1$-$C_6$ alkyl" includes alkyl groups having 1, 2, 3, 4, 5, or 6 carbons in a linear or branched arrangement. Non-limiting examples of alkyl groups include methyl, ethyl, iso-propyl, tert-butyl, n-hexyl. As used herein, the term "aminoalkyl" refers to an alkyl group as defined above, substituted at any position with one or more amino groups as permitted by normal valency. The amino groups may be unsubstituted, monosubstituted, or di-substituted. Non-limiting examples of aminoalkyl groups include aminomethyl, dimethylaminomethyl, and 2-aminoprop-1-yl.

As used herein, the term "cycloalkyl" means a saturated or unsaturated nonaromatic hydrocarbon ring group having from 3 to 14 carbon atoms, unless otherwise specified.

As used herein, "alkoxyl" or "alkoxy" refers to —O-alkyl radical having the indicated number of carbon atoms. For example, $C_{1-6}$ alkoxy is intended to include $C_1$, $C_2$, $C_3$, $C_4$, $C_5$, and $C_6$ alkoxy groups. For example, $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, or hexanoyl), alkenoyl (e.g., acrvloyl) alkynoyl (e.g., ethvnoyl, propynoyl, butynoyl, pentynoyl, or hexynoyl), aryloyl (e.g., benzoyl), heteroaryloyl (e.g., pyrroloyl, imidazoloyl, quinolinoyl, or pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl, or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxycarbonyl.

As used herein, "aryl" or "aromatic" means any stable monocyclic or polycyclic carbon ring of up to 6 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N, and S. Examples of heteroaryl groups include, but are not limited to, acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, and tetrabydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, ti-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N, and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition of the number, severity, and/or frequency of one or more symptoms of a disease in a subject.

As used herein, the phrase "deliver to a cell." and the like, when referring to a cargo molecule, means functionally delivering the cargo molecule to the cell. The phrase "functionally delivering," means delivering the cargo molecule to the cell in a manner that enables the cargo molecule to have the expected biological activity. When specifically referring to a cargo molecule that is an RNAi agent, the expected biological activity is, for example, sequence-specific inhibition of gene expression.

Unless stated otherwise, use of the symbol

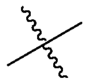

as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, a linking group is one or more atoms that connects one molecule or portion of a molecule to another to second molecule or second portion of a molecule. In the art, the terms linking group and spacers are sometimes used interchangeably. Similarly, as used in the art, the term scaffold is sometimes used interchangeably with a linking group. In some embodiments. In some embodiments, a linking group can include or consist of a PEG group or PEG moiety.

As used herein, the term "linked" or "conjugated" when referring to the connection between two molecules means that two molecules are joined by a covalent bond or that two molecules are associated via noncovalent bonds (e.g., hydrogen bonds or ionic bonds). In some examples, where the term "linked" refers to the association between two molecules via noncovalent bonds, the association between the two different molecules has a $K_D$ of less than $1\times10^{-4}$ M (e.g., less than $1\times10^{-5}$ M, less than $1\times10^{-6}$ M, or less than $1\times10^{-7}$ M) in physiologically acceptable buffer (e.g., phosphate buffered saline). Unless stated, the term linked as used herein may refer to the connection between a first compound and a second compound either with or without any intervening atoms or groups of atoms.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Multidentate αvβ3 Integrin Ligands and Scaffolds

As disclosed herein, in some embodiments, one or more αvβ3/5 integrin ligands may be linked to one or more cargo molecules. In some embodiments, only one integrin ligand is conjugated to a cargo molecule (referred to herein as a "monodentate" or "monovalent" ligand). In some embodiments, two integrin ligands are conjugated to a cargo molecule (referred to herein as a "bidentate" or "divalent" targeting group). In some embodiments, three integrin ligands are conjugated to a cargo molecule (referred to herein as a "tridentate" or "trivalent" targeting group). In some embodiments, four integrin ligands are conjugated to a cargo molecule (referred to herein as a "tetradentate" or "tetravalent" targeting group). In some embodiments, more than four integrin ligands are conjugated to a cargo molecule.

In some embodiments, where only one integrin ligand is conjugated to a cargo molecule (referred to herein as a "monodentate" ligand), the integrin ligand may be conjugated directly to the cargo molecule. In some embodiments, an integrin ligand disclosed herein can be conjugated to a cargo molecule via a scaffold or other linker structure.

In some embodiments, the integrin ligands disclosed herein include one or more scaffolds. Scaffolds, also sometimes referred to in the art as linking groups or linkers, can be used to facilitate the linkage of one or more cargo molecules to one or more integrin ligands disclosed herein. Useful scaffolds compatible with the ligands disclosed herein are generally known in the art. Non-limiting examples of scaffolds that can be used with the αvβ3 integrin ligands disclosed herein include, but are not limited to polymers and polyamino acids (e.g., bis-glutamic acid, poly-L-lysine, etc.). In some embodiments, scaffolds may include cysteine linkers or groups, DBCO-$PEG_{1-24}$-NHS, Propargyl-$PEG_{1-24}$-NHS, and/or multidentate DBCO and/or propargyl moieties.

In some embodiments, the scaffold used for linking one or more integrin ligands disclosed herein to one or more cargo molecules has the following structure:

(Scaffold 1)

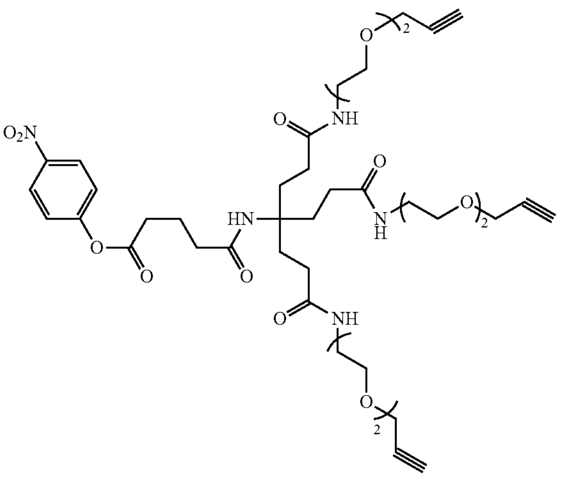

The use of Scaffold 1, for example, facilitates efficient conjugation with both the integrin ligand monomers and the one or more cargo molecules. Scaffold 1 includes an amine reactive p-nitrophenol (also called 4-nitrophenol) ester, an amide linkage, and three $PEG_2$ unit arms, as well as terminal alkynes. The 4-nitrophenol ester can be conjugated with the primary amine on a cargo molecule, such as the primary amine on an RNA trigger formulated with a terminal amine group (e.g., $NH_2$—$(CH_2)_6$), through amide formation. The terminal alkyne can be conjugated with azido modified ligands (both peptides and small molecules) through copper-catalyzed click chemistry.

In some embodiments, the cargo molecule is an RNAi agent. In some embodiments, Scaffold 1 may be attached to the terminal end of an RNAi agent, such as to the 5' terminal end of the sense strand of an RNAi agent. For example, the 5' terminal end of the sense strand of an RNAi agent may be modified to include a $C_6$ amine (—$(CH_2)_6$—$NH_2$) attached to the 5' end of the 5' terminal nucleotide of the RNAi agent. An RNAi agent having such a $C_6$ amine modification (or another other modification resulting in a terminal amine) may be readily conjugated to Scaffold 1, as shown by the representation in the following structure:

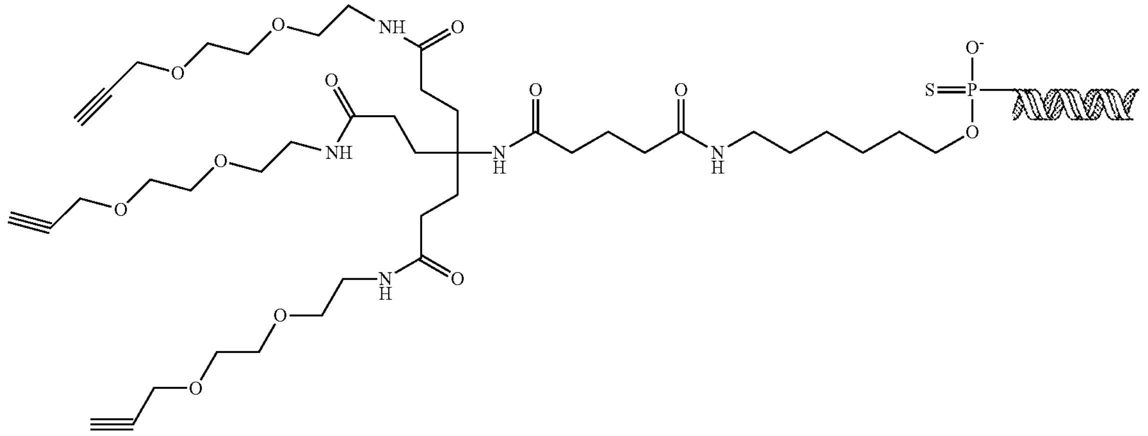 [SMILES: C#CCOCCOCCNC(=O)CCC(CCC(=O)NCCOCCOCC#C)(CCC(=O)NCCOCCOCC#C)NC(=O)CCCC(=O)NCCCCCCOP(C)([O-])=S]

(Structure 380), wherein 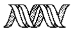 indicates an RNAi agent.

The alkyne groups of Structure 380, above, may then be conjugated to the integrin ligands disclosed herein to form tridentate integrin targeting groups.

In some embodiments, a scaffold may be synthesized using DBCO (dibenzocyclooctyne), which can be represented by the following structure:

(Structure 381)

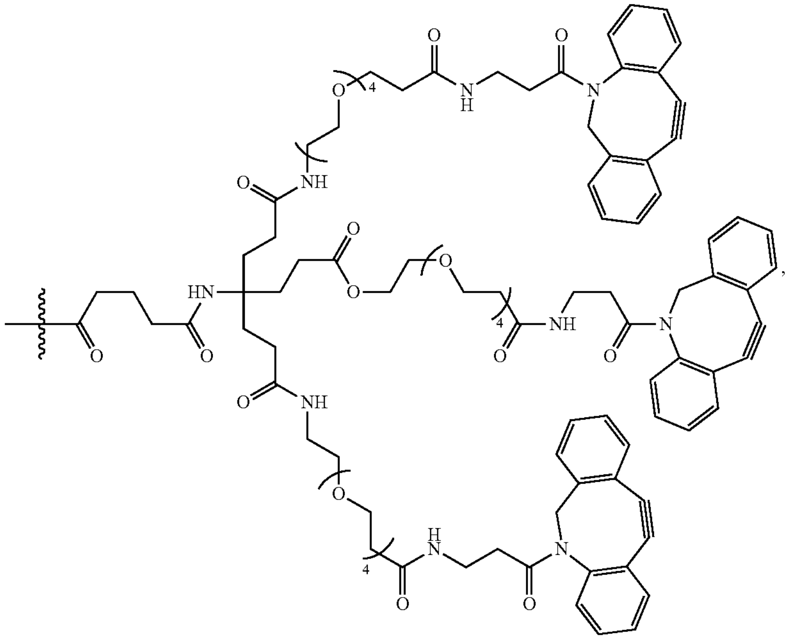

wherein  indicates attachment to a reactive group or a moiety comprising cargo molecule.

In some embodiments, triazole groups are formed between the RNAi agent and the integrin ligands disclosed herein, as shown in the following general structure:

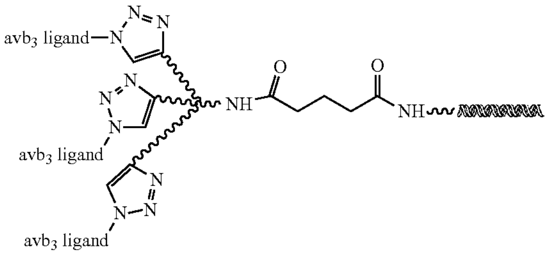

(Structure 390), wherein indicates any suitable scaffold or linker that can be used to bind a ligand to an RNAi agent, and indicates an RNAi agent.

In some embodiments, a scaffold may be synthesized as a phosphoramidite compound, an example of which is shown in the following structure:

(Structure 400)

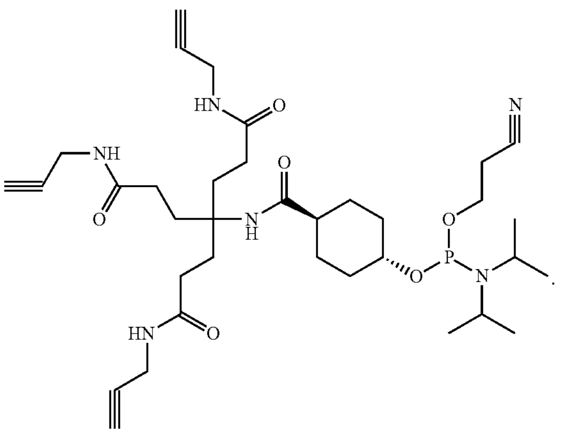

The trialkyne compound of Structure 400 allows for a tridentate ligand to be readily coupled to the 5' terminal end of the sense strand of an RNAi agent through a click reaction of an alkyne with a targeting ligand comprising an azide.

In some embodiments, an integrin targeting group disclosed herein comprises Structure 4.1a, Structure 4.2a, Structure 4.3a, Structure 4.4a, Structure 4.5a, Structure 4.6a, Structure 4.8a, Structure 4.9a, Structure 4.10a, Structure 4.11a, Structure 4.12a, and Structure 4.13a wherein the αvβ3 integrin targeting group is a tridentate targeting group and comprises three ligands.

Reactive Groups and Protected Reactive Groups

Reactive groups are well known in the art and provide for formation of covalent linkages between two molecules or reactants. Suitable reactive groups for use in the scope of the inventions herein include, but are not limited to: amino groups, amide groups, carboxylic acid groups, azides, alkynes, propargyl groups, BCN (biclclo[6.1.0]nonyne, DBCO (dibenzocyclooctyne) thiols, maleimide groups, aminooxy groups, N-hydroxysuccinimide (NHS) or other activated ester (for example, PNP, TFP, PFP), bromo groups, aldehydes, carbonates, tosylates, tetrazines, trans-cyclooctene (TCO), hydrazides, hydroxyl groups, disulfides, and orthopyridyl disulfide groups.

Incorporation of reactive groups can facilitate conjugation of an integrin ligand disclosed herein to a cargo molecule. Conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction and click chemistry cycloaddition reaction.

In some embodiments, the integrin targeting ligands disclosed herein are synthesized as a tetrafluorophenyl (TFP) ester, which can be displaced by a reactive amino group to attach a cargo molecule. In some embodiments, the integrin targeting ligands disclosed herein are synthesized as an azide, which can be conjugated to a propargyl or DBCO group, for example, via click chemistry cycloaddition reaction, to attach a cargo molecule.

Protected reactive groups are also commonly used in the art. A protecting group provides temporary chemical transformation of a reactive group into a group that does not react under conditions where the non-protected group reacts, e.g, to provide chemo-selectivity in a subsequent chemical reaction. Suitable protected reactive groups for use in the scope of the inventions herein include, but are not limited to, BOC groups (t-butoxycarbonyl), Fmoc (9-fluorenylmethoxycarbonyl), carboxybenzyl (CBZ) groups, benzyl esters, and PBF (2,2,4,6,7-pentamethyldihydrobenzofuran-5-sulfonyl).

Cargo Molecules (Including RNAi Agents)

A cargo molecule is any molecule which, when detached from the integrin ligands described herein, would have a desirable effect on a cell comprising an integrin receptor. A cargo molecule can be, but is not limited to, a pharmaceutical ingredient, a drug product, a prodrug, a substance with a known therapeutic benefit, a small molecule, an antibody, an antibody fragment, an immunoglobulin, a monoclonal antibody, a label or marker, a lipid, a natural or modified nucleic acid or polynucleotide, a peptide, a polymer, a polyamine, a protein, an aptamer, a toxin, a vitamin, a PEG, a hapten, a digoxigenin, a biotin, a radioactive atom or molecule, or a fluorophore. In some embodiments, one or more cargo molecules (e.g., the same or different cargo molecules) are linked to one or more integrin ligands to target the cargo molecules to a cell expressing integrin αvβ3 and/or integrin αvβ5.

In some embodiments, the one or more cargo molecules is a pharmaceutical ingredient or pharmaceutical composition. In some embodiments, the one or more cargo molecules is an oligonucleotide-based compound. As used herein, an "oligonucleotide-based compound" is a nucleotide sequence containing about 10-50 (e.g., 10 to 48, 10 to 46, 10 to 44, 10 to 42, 10 to 40, 10 to 38, 10 to 36, 10 to 34, 10 to 32, 10 to 30, 10 to 28, 10 to 26, 10 to 24, 10 to 22, 10 to 20, 10 to 18, 10 to 16, 10 to 14, 10 to 12, 12 to 50, 12 to 48, 12 to 46, 12 to 44, 12 to 42, 12 to 40, 12 to 38, 12 to 36, 12 to 34, 12 to 32, 12 to 30, 12 to 28, 12 to 26, 12 to 24, 12 to 22, 12 to 20, 12 to 18, 12 to 16, 12 to 14, 14 to 50, 14 to 48, 14 to 46, 14 to 44, 14 to 42, 14 to 40, 14 to 38, 14 to 36, 14 to 34, 14 to 32, 14 to 30, 14 to 28, 14 to 26, 14 to 24, 14 to 22, 14 to 20, 14 to 18, 14 to 16, 16 to 50, 16 to 48, 16 to 46, 16 to 44, 16 to 42, 16 to 40, 16 to 38, 16 to 36, 16 to 34, 16 to 32, 16 to 30, 16 to 28, 16 to 26, 16 to 24, 16 to 22, 16 to 20, 16 to 18, 18 to 50, 18 to 48, 18 to 46, 18 to 44, 18 to 42, 18 to 40, 18 to 38, 18 to 36, 18 to 34, 18 to 32, 18 to 30, 18 to 28, 18 to 26, 18 to 24, 18 to 22, 18 to 20, 20 to 50, 20 to 48, 20 to 46, 20 to 44, 20 to 42, 20 to 40, 20 to 38, 20 to 36, 20 to 34, 20 to 32, 20 to 30, 20 to 28, 20 to 26, 20 to 24, 20 to 22, 22 to 50, 22 to 48, 22 to 46, 22 to 44, 22 to 42, 22 to 40, 22 to 38, 22 to 36, 22 to 34, 22 to 32, 22 to 30, 22 to 28, 22 to 26, 22 to 24, 24 to 50, 24 to 48, 24 to 46, 24 to 44, 24 to 42, 24 to 40, 24 to 38, 24 to 36, 24 to 34, 24 to 32, 24 to 30, 24 to 28, 24 to 26, 26 to 50, 26 to 48, 26 to 46, 26 to 44, 26 to 42, 26 to 40, 26 to 38, 26 to 36, 26 to 34, 26 to 32, 26 to 30, 26 to 28, 28 to 50, 28 to 48, 28 to 46, 28 to 44, 28 to 42, 28 to 40, 28 to 38, 28 to 36, 28 to 34, 28 to 32, to 28 to 30, 30 to 50, 30 to 48, 30 to 46, 30 to 44, 30 to 42, 30 to 40, 30 to 38, 30 to 36, 30 to 34, 30 to 32, 32 to 50, 32 to 48, 32 to 46, 32 to 44, 32 to 42, 32 to 40, 32 to 38, 32 to 36, 32 to 34, 34 to 50, 34 to 48, 34 to 46, 34 to 44, 34 to 42, 34 to 40, 34 to 38, 34 to 36, 36 to 50, 36 to 48, 36 to 46, 36 to 44, 36 to 42, 36 to 40, 36 to 38, 38 to 50, 38 to 48, 38 to 46, 38 to 44, 38 to 42, 38 to 40, 40 to 50, 40 to 48, 40 to 46, 40 to 44, 40 to 42, 42 to 50, 42 to 48, 42 to 46, 42 to 44, 44 to 50, 44 to 48, 44 to 46, 46 to 50, 46 to 48, or 48 to 50) nucleotides or nucleotide base pairs. In some embodiments, an oligonucleotide-based compound has a nucleobase sequence that is at least partially complementary to a coding sequence in an expressed target nucleic acid or target gene (e.g., the gene transcript or mRNA of a target gene) within a cell. In some embodiments, the oligonucleotide-based compounds, upon delivery to a cell expressing a gene, are able to inhibit the expression of the underlying gene, and are referred to herein as "expression-inhibiting oligonucleotide-based compounds." The gene expression can be inhibited in vitro or in vivo.

"Oligonucleotide-based compounds" include, but are not limited to: single-stranded oligonucleotides, single-stranded antisense oligonucleotides, short or small interfering RNAs (siRNAs), double-strand RNAs (dsRNA), micro RNAs (miRNAs), short hairpin RNAs (shRNA), ribozymes, interfering RNA molecules, and dicer substrates. In some embodiments, an oligonucleotide-based compound is a single-stranded oligonucleotide, such as an antisense oligonucleotide. In some embodiments, an oligonucleotide-based compound is a double-stranded oligonucleotide. In some embodiments, an oligonucleotide-based compound is a double-stranded oligonucleotide that is an RNAi agent.

In some embodiments, the one or more cargo molecules is/are an "RNAi agent," which as defined herein is a chemical composition that includes an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short or small interfering RNAs (siRNAs), double-strand RNAs (dsRNA), micro RNAs (miRNAs), short hairpin RNAs (shRNA), and dicer substrates. The antisense strand of the RNAi agents described herein is at least partially complementary to the mRNA being targeted. RNAi agents can include one or more modified nucleotides and/or one or more non-phosphodiester linkages.

Typically, RNAi agents can be comprised of at least a sense strand (also referred to as a passenger strand) that includes a first sequence, and an antisense strand (also referred to as a guide strand) that includes a second sequence. The length of an RNAi agent sense and antisense strands can each be 16 to 49 nucleotides in length. In some embodiments, the sense and antisense strands of an RNAi agent are independently 17 to 26 nucleotides in length. In some embodiments, the sense and antisense strands are independently 19 to 26 nucleotides in length. In some embodiments, the sense and antisense strands are independently 21 to 26 nucleotides in length. In some embodiments, the sense and antisense strands are independently 21 to 24 nucleotides in length. In some embodiments, the sense and antisense strands are each 21 nucleotides in length. The sense and antisense strands can be either the same length or different lengths. The RNAi agents include an antisense strand sequence that is at least partially complementary to a sequence in the target gene, and upon delivery to a cell expressing the target, an RNAi agent may inhibit the expression of one or more target genes in vivo or in vitro.

Oligonucleotide-based compounds generally, and RNAi agents specifically, may be comprised of modified nucleotides and/or one or more non-phosphodiester linkages. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides, 2'-modified nucleotides, 3' to 3' linkages (inverted) nucleotides, non-natural base-comprising nucleotides, bridged nucleotides, peptide nucleic acids, 2',3'-seco nucleotide mimics (unlocked nucleobase analogues, locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e. a nucleotide with a group other than a hydroxyl group at the 2' position of the five-membered sugar ring) include, but are not limited to, 2'-O-methyl nucleotides, 2'-deoxy-2'-fluoro nucleotides, 2'-deoxy nucleotides, 2'-methoxyethyl (2'-O-2-methoxylethyl) nucleotides, 2'-amino nucleotides, and 2'-alkyl nucleotides.

Moreover, one or more nucleotides of an oligonucleotide-based compound, such as an RNAi agent, may be linked by non-standard linkages or backbones (i.e., modified internucleoside linkages or modified backbones). A modified internucleoside linkage may be a non-phosphate-containing covalent internucleoside linkage. Modified internucleoside linkages or backbones include, but are not limited to, 5'-phosphorothioate groups, chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'.

It is not necessary for all positions in a given compound to be uniformly modified. Conversely, more than one modification may be incorporated in a single oligonucleotide-based compound or even in a single nucleotide thereof.

In some embodiments, the cargo molecule is an RNAi agent for inhibiting HIF-2 alpha (EPAS1) gene expression. The cargo molecule may be an RNAi agent described in International Patent Application Publication No. WO 2016/

196239 and WO 2014/134255, each of which is herein incorporated by reference in its entirety.

The RNAi agent sense strands and antisense strands may be synthesized and/or modified by methods known in the art. For example, the disclosure of RNAi agents directed to the inhibition of HIF-2 alpha gene expression may be found, for example, in International Patent Application Publication No. WO 2016/196239, which is incorporated by reference herein in its entirety.

In some embodiments, the one or more cargo molecule(s) can include or consist of a PEG moiety that can acts as a pharmacokinetic (PK) enhancer or modulator. In some embodiments, the one or more cargo molecules can include a PEG moiety having about 20-900 ethylene oxide ($CH_2$—$CH_2$—O) units (e.g., 20 to 850, 20 to 800, 20 to 750, 20 to 700, 20 to 650, 20 to 600, 20 to 550, 20 to 500, 20 to 450, 20 to 400, 20 to 350, 20 to 300, 20 to 250, 20 to 200, 20 to 150, 20 to 100, 20 to 75, 20 to 50, 100 to 850, 100 to 800, 100 to 750, 100 to 700, 100 to 650, 100 to 600, 100 to 550, 100 to 500, 100 to 450, 100 to 400, 100 to 350, 100 to 300, 100 to 250, 100 to 200, 100 to 150, 200 to 850, 200 to 800, 200 to 750, 200 to 700, 200 to 650, 200 to 600, 200 to 550, 200 to 500, 200 to 450, 200 to 400, 200 to 350, 200 to 300, 200 to 250, 250 to 900, 250 to 850, 250 to 800, 250 to 750, 250 to 700, 250 to 650, 250 to 600, 250 to 550, 250 to 500, 250 to 450, 250 to 400, 250 to 350, 250 to 300, 300 to 900, 300 to 850, 300 to 800, 300 to 750, 300 to 700, 300 to 650, 300 to 600, 300 to 550, 300 to 500, 300 to 450, 300 to 400, 300 to 350, 350 to 900, 350 to 850, 350 to 800, 350 to 750, 350 to 700, 350 to 650, 350 to 600, 350 to 550, 350 to 500, 350 to 450, 350 to 400, 400 to 900, 400 to 850, 400 to 800, 400 to 750, 400 to 700, 400 to 650, 400 to 600, 400 to 550, 400 to 500, 400 to 450, 450 to 900, 450 to 850, 450 to 800, 450 to 750, 450 to 700, 450 to 650, 450 to 600, 450 to 550, 450 to 500, 500 to 900, 500 to 850, 500 to 800, 500 to 750, 500 to 700, 500 to 650, 500 to 600, 500 to 550, 550 to 900, 550 to 850, 550 to 800, 550 to 750, 550 to 700, 550 to 650, 550 to 600, 600 to 900, 600 to 850, 600 to 800, 600 to 750, 600 to 700, 600 to 650, 650 to 900, 650 to 850, 650 to 800, 650 to 750, 650 to 700, 700 to 900, 700 to 850, 700 to 800, 700 to 750, 750 to 900, 750 to 850, 750 to 800, 800 to 900, 850 to 900, or 850 to 900 ethylene oxide units). In some embodiments, the one or more cargo molecule(s) consist of a PEG moiety having approximately 455 ethylene oxide units (about 20 kilodalton (kDa) molecular weight). In some embodiments, a PEG moiety has a molecular weight of about 2 kilodaltons. In some embodiments, a PEG moiety has a molecular weight of about 20 kilodaltons. In some embodiments, a PEG moiety has a molecular weight of about 40 kilodaltons. The PEG moieties described herein may be linear or branched. The PEG moieties may be discrete (monodispersed) or non-discrete (polydispersed). PEG moieties for use as a PK enhancing cargo molecule may be purchased commercially. In some embodiments, the one or more cargo molecule(s) include a PEG moiety that can act as a PK modulator or enhancer, as well as a different cargo molecule, such as a pharmaceutically active ingredient or compound.

The described integrin ligands include salts or solvates thereof. Solvates of an integrin ligand is taken to mean adductions of inert solvent molecules onto the integrin ligand which form owing to their mutual attractive force. Solvates are, for example, mono- or dihydrates or addition compounds with alcohols, such as, for example, with methanol or ethanol.

Free amino groups or free hydroxyl groups can be provided as substituents of integrin ligands with corresponding protecting groups.

The αvβ3 integrin ligands also include, e.g., derivatives, i.e., integrin ligands modified with, for example, alkyl or acyl groups, sugars or oligopeptides, which are cleaved either in vitro or in an organism.

In some embodiments, an integrin ligand disclosed herein facilitates the delivery of a cargo molecule into the cytosol of a cell presenting integrin αvβ3 and/or integrin αvβ5 on its surface, either through ligand-mediated endocytosis, pinocytosis, or by other means. In some embodiments, an integrin ligand disclosed herein facilitates the delivery of a cargo molecule to the plasma membrane of a cell presenting integrin αvβ3 and/or integrin αvβ5.

Pharmaceutical Compositions

In some embodiments, the present disclosure provides pharmaceutical compositions that include, consist of, or consist essentially of, one or more of the integrin ligands disclosed herein.

As used herein, a "pharmaceutical composition" comprises a pharmacologically effective amount of an Active Pharmaceutical Ingredient (API), and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions described herein can contain other additional components commonly found in pharmaceutical compositions. In some embodiments, the additional component is a pharmaceutically-active material. Pharmaceutically-active materials include, but are not limited to: anti-pruritics, astringents, local anesthetics, or anti-inflammatory agents (e.g., antihistamine, diphenhydramine, etc.), small molecule drug, antibody, antibody fragment, aptamers, and/or vaccine.

The pharmaceutical compositions may also contain preserving agents, solubilizing agents, stabilizing agents, wetting agents, emulsifiers, sweeteners, colorants, odorants, salts for the variation of osmotic pressure, buffers, coating agents, or antioxidants. They may also contain other agent with a known therapeutic benefit.

The pharmaceutical compositions can be administered in a number of ways depending upon whether local or systemic treatment is desired and upon the area to be treated. Administration can be made by any way commonly known in the art, such as, but not limited to, topical (e.g., by a transdermal patch), pulmonary (e.g., by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (e.g., via an implanted device), intracranial, intraparenchymal, intrathecal, and intraventricular, administration. In some embodiments, the pharmaceutical compositions described herein are administered by intravenous injection or infusion or subcutaneous injection. The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels, or solutions; or parenterally, for example using injectable solutions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of any of the ligands described herein that can be in microcrystalline form, for example, in the form of an aqueous microcrystalline suspension. Liposomal formulations or biodegradable polymer systems can also be used to present any of the ligands described herein for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). As used herein, “pharmacologically effective amount,” “therapeutically effective amount,” or simply “effective amount” refers to that amount of an the pharmaceutically active agent to produce a pharmacological, therapeutic or preventive result.

Medicaments containing an αvβ3 integrin ligand are also an object of the present invention, as are processes for the manufacture of such medicaments, which processes comprise bringing one or more compounds containing a αvβ3 integrin ligand, and, if desired, one or more other substances with a known therapeutic benefit, into a pharmaceutically acceptable form.

The described integrin ligands and pharmaceutical compositions comprising integrin ligands disclosed herein may be packaged or included in a kit, container, pack, or dispenser. The integrin ligands and pharmaceutical compositions comprising the integrin ligands may be packaged in pre-filled syringes or vials.

Linking Groups, Pharmacokinetic (PK) Enhancers, Pharmacodynamic (PD) Modulators, Delivery Vehicles, and Targeting Groups In some embodiments, an αvβ3 ligand is conjugated to one or more non-nucleotide groups including, but not limited to, a linking group, a pharmacokinetic (PK) enhancer (also referred to as a PK modulator), a pharmacodynamic (PD) modulator, a delivery polymer, or a delivery vehicle. The non-nucleotide group can enhance targeting, delivery, or attachment of the cargo molecule. Examples of scaffolds for targeting groups and linking groups are disclosed herein. The non-nucleotide group can be covalently linked to the 3' and/or 5' end of either the sense strand and/or the antisense strand. In embodiments where the cargo molecule is an RNAi agent, the RNAi agent contains a non-nucleotide group linked to the 3' and/or 5' end of the sense strand. In some embodiments, a non-nucleotide group is linked to the 5' end of an RNAi agent sense strand. An integrin ligand disclosed herein can be linked directly or indirectly to the cargo molecule via a linker/linking group. In some embodiments, an integrin ligand is linked to the cargo molecule via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent. In some embodiments a non-nucleotide group enhances or modulates the pharmacodynamic properties of an RNAi agent or conjugate to which it is attached to improve cell- or tissue-specific distribution and cell-specific uptake of the RNAi agent or conjugate.

Targeting groups or targeting moieties enhance the pharmacokinetic or biodistribution properties of a cargo molecule to which they are attached to improve cell-specific (including, in some cases, organ specific) distribution and cell-specific (or organ specific) uptake of the cargo molecule. In some embodiments, a targeting group may comprise an αvβ3 ligand as described herein. In some embodiments, a targeting group comprises a linker. In some embodiments, a targeting group comprises a PK enhancer. In some embodiments, an αvβ3 integrin ligand is linked to a cargo molecule using a linker, such as a PEG linker or one, two, or three abasic and/or ribitol (abasic ribose) residues, which in some instances can serve as linkers. Targeting groups may comprise one or more targeting ligands. In some embodiments, a targeting group may comprise one to four integrin ligands disclosed herein. In some embodiments, a targeting group is a tridentate targeting group and comprises three integrin ligands disclosed herein.

Cargo molecules can be synthesized having a reactive group, such as an amino group (also referred to herein as an amine). In embodiments where the cargo molecule is an RNAi agent, the reactive group may be linked at the 5'-terminus and/or the 3'-terminus. The reactive group can be used subsequently to attach an αvβ3 integrin ligand using methods typical in the art.

For example, in some embodiments, an RNAi agent is synthesized having an $NH_2$—$C_6$ group at the 5'-terminus of the sense strand of the RNAi agent. The terminal amino group subsequently can be reacted to form a conjugate with, for example, a group that includes an integrin targeting ligand. In some embodiments, an RNAi agent is synthesized having one or more alkyne groups at the 5'-terminus of the sense strand of the RNAi agent. The terminal alkyne group (s) can subsequently be reacted to form a conjugate with, for example, a group that includes an αvβ3 integrin targeting ligand.

In some embodiments, a linking group is conjugated to the αvβ3 ligand. The linking group facilitates covalent linkage of the αvβ3 ligand to a cargo molecule, PK enhancer, delivery polymer, or delivery vehicle. Examples of linking groups, include, but are not limited to: Alk-SMPT-C6, Alk-SS—C6, DBCO-TEG, Me-Alk-SS—C6, and C6-SS-Alk-Me, reactive groups such a primary amines and alkynes, alkyl groups, abasic residues/nucleotides, amino acids, tri-alkyne functionalized groups, ribitol, and/or PEG groups.

A linker or linking group is a connection between two atoms that links one chemical group (such as an RNAi agent) or segment of interest to another chemical group (such as an αvβ3 integrin ligand, PK enhancer, PD modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, αvβ3 ligands are linked to cargo molecules without the use of an additional linker. In some embodiments, the αvβ3 ligand is designed having a linker readily present to facilitate the linkage to a cargo molecule. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

Examples of certain linking groups and scaffolds are provided in Table A.

TABLE A

| Structures Representing Various Linking Groups and Scaffolds |
| --- |
| 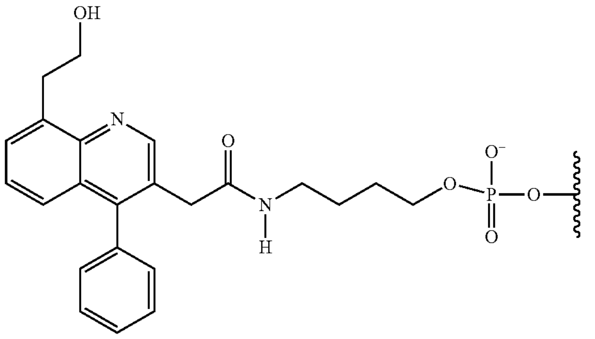 |
| (PAZ) |
| When positioned at the 3' terminal end of oligonucleotide: |
| 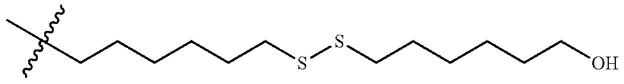 |
| (C6-SS-C6) |

TABLE A-continued

Structures Representing Various Linking Groups and Scaffolds

When positioned internally in oligonucleotide:

linkage towards 5′ end of oligonucleotide linkage towards 3′ end of oligonucleotide

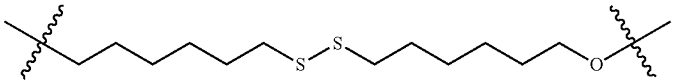

(C6-SS-C6)

When positioned at the 3' terminal end of oligonucleotide:

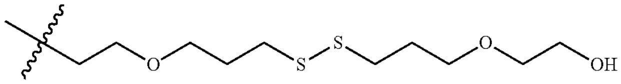 [SMILES: *CCOCCCSSCCCOCCO]

When positioned internally in oligonucleotide:

linkage towards 5′ end of oligonucleotide linkage towards 3′ end of oligonucleotide

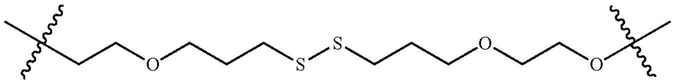

(6-SS-6)

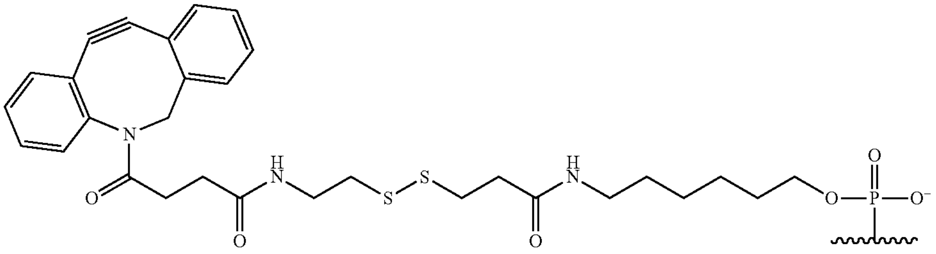

(C6-SS-Alk) or (Alk-SS-C6)

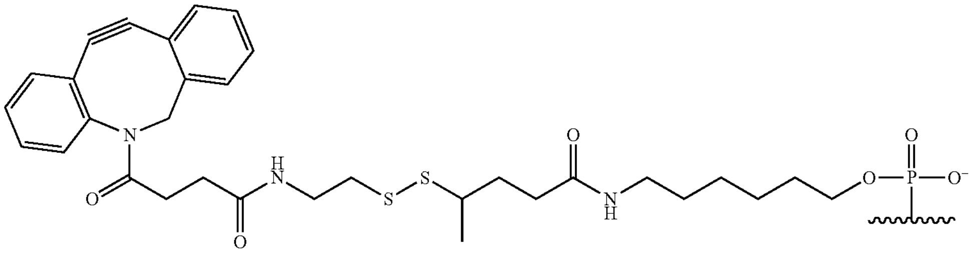

(C6-SS-Alk-Me)

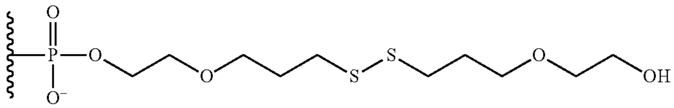

(PEG-C3-SS)

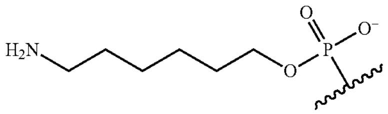

(NH2-C6)

TABLE A-continued
Structures Representing Various Linking Groups and Scaffolds
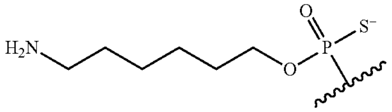
(NH2-C6)s
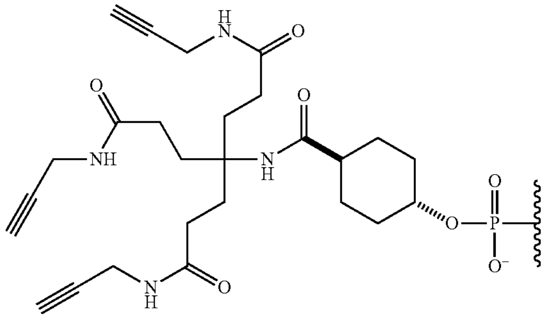
(TriAlk1)
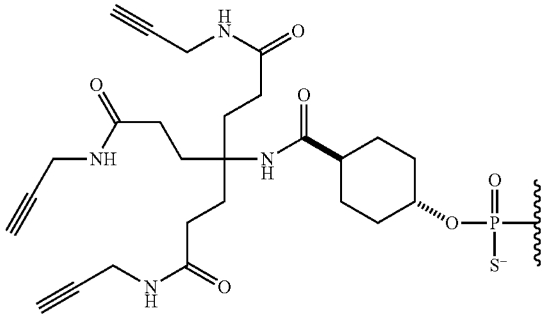
(TriAlk1)s
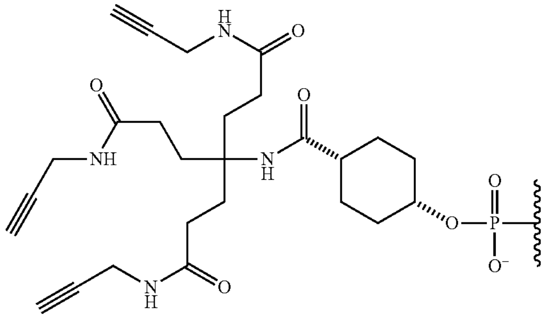
(TriAlk2)
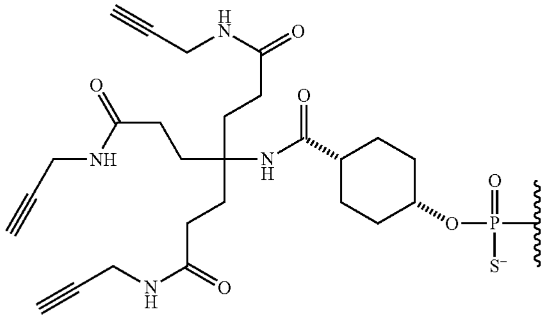
(TriAlk2)s TABLE A-continued
| Structures Representing Various Linking Groups and Scaffolds |
| --- |
| 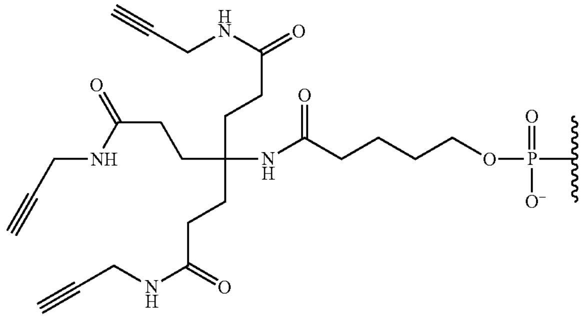 |
| (TriAlk3) |
| 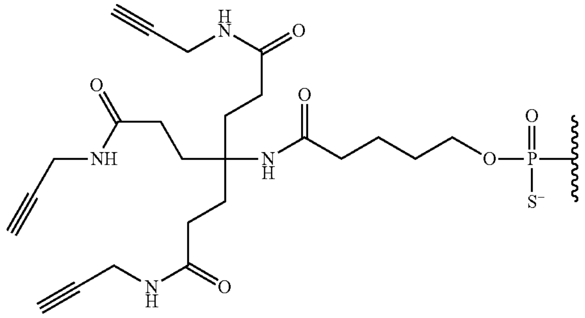 |
| (TriAlk3)s |
| 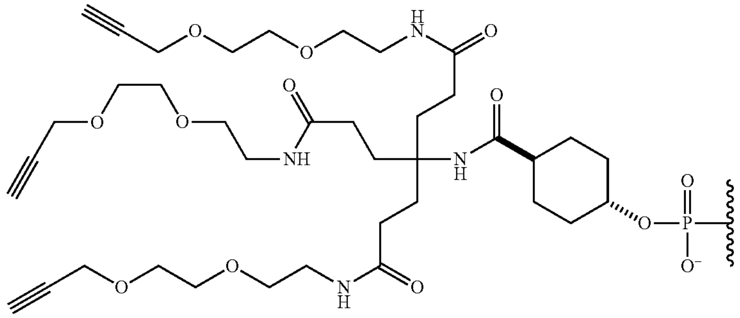 |
| (TriAlk4) |
| 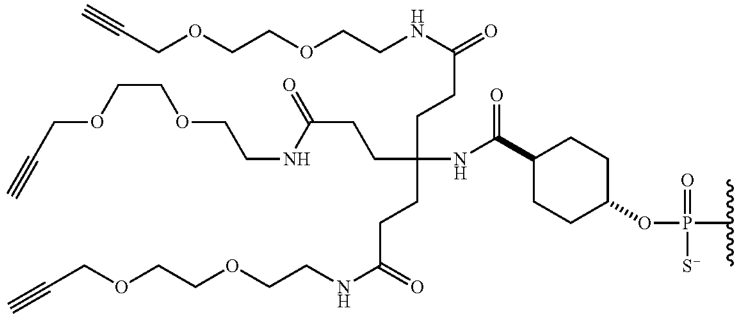 |
| (TriAlk4)s |

TABLE A-continued
| Structures Representing Various Linking Groups and Scaffolds |
| --- |
| 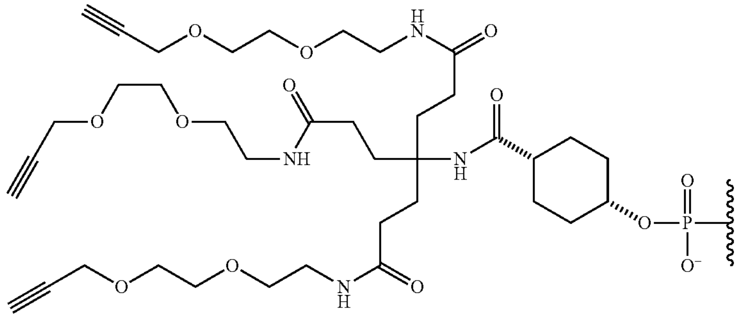 |
| (TriAlk5) |
| 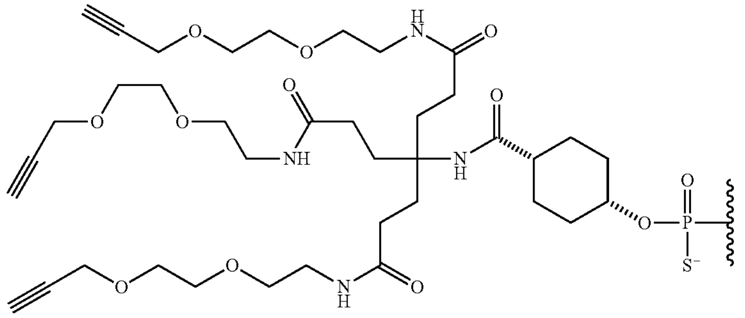 |
| (TriAlk5)s |
| 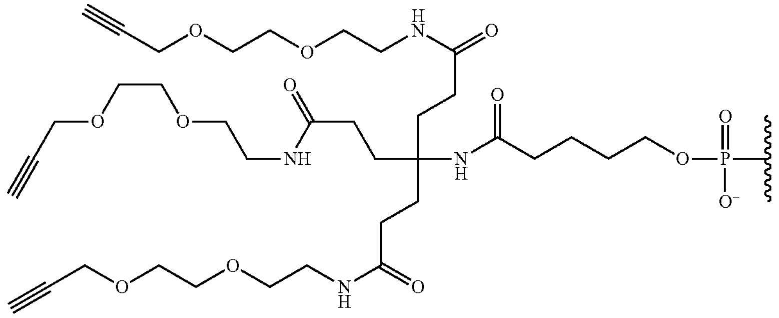 |
| (TriAlk6) |
| 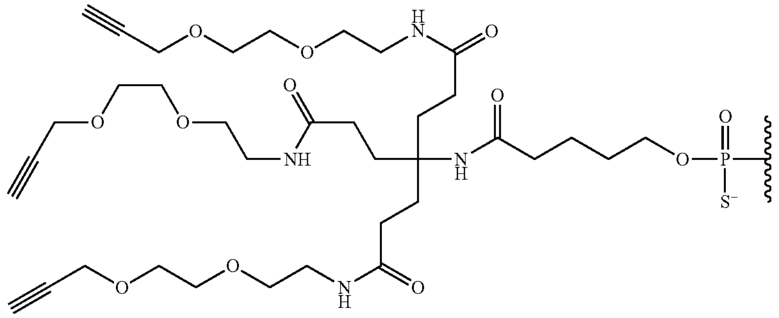 |
| (TriAlk6)s |

TABLE A-continued
| Structures Representing Various Linking Groups and Scaffolds |
| --- |
| 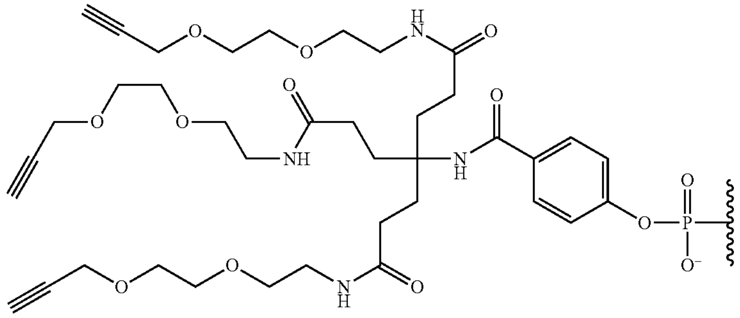 |
| (TriAlk7) |
| 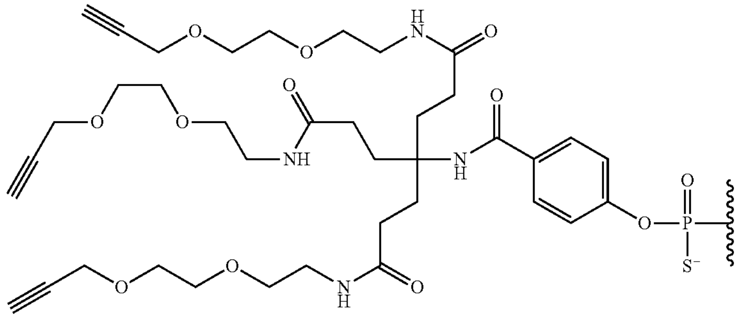 |
| (TriAlk7)s |
| 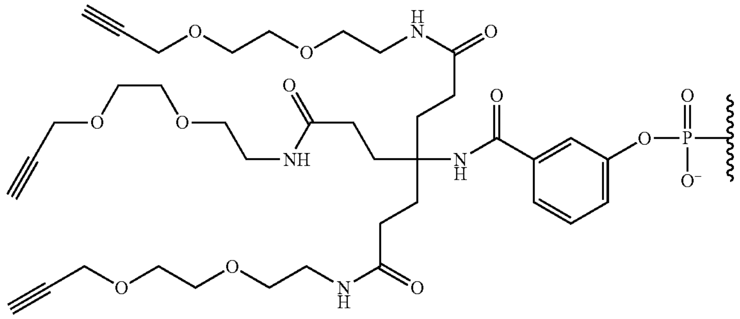 |
| (TriAlk8) |
| 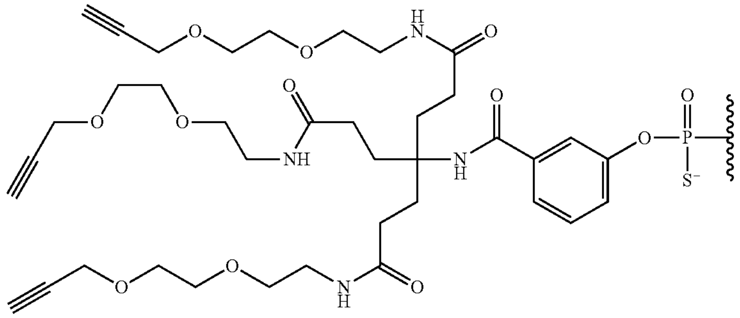 |
| (TriAlk8)s |

TABLE A-continued
Structures Representing Various Linking Groups and Scaffolds
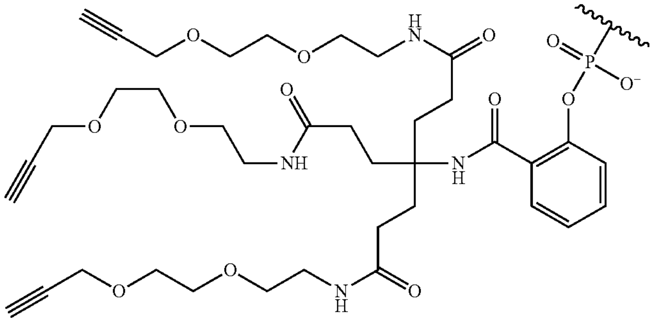
(TriAlk9)
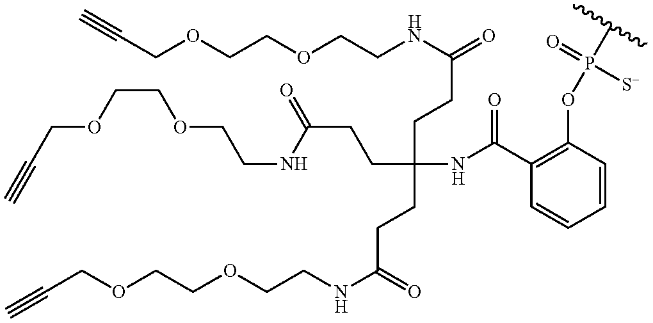
(TriAlk9)s
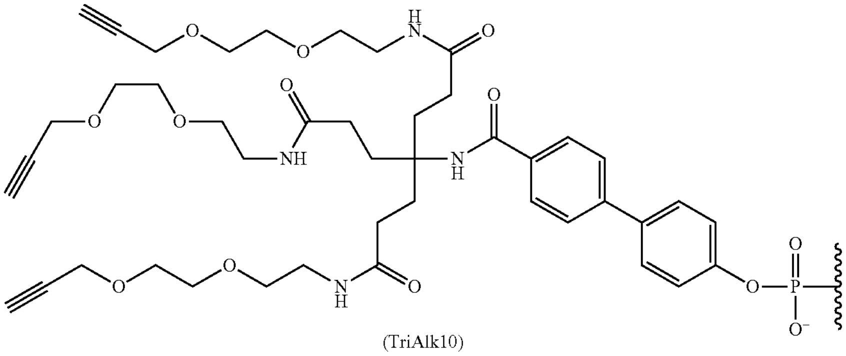 [SMILES: *P(=O)([O-])Oc1ccc(-c2ccc(C(=O)NC(CCC(=O)NCCOCCOCC#C)(CCC(=O)NCCOCCOCC#C)CCC(=O)NCCOCCOCC#C)cc2)cc1]
(TriAlk10)
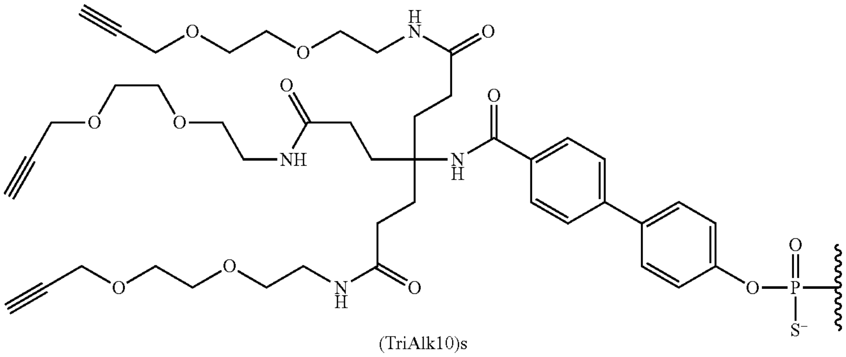
(TriAlk10)s TABLE A-continued
| Structures Representing Various Linking Groups and Scaffolds |
| --- |
| 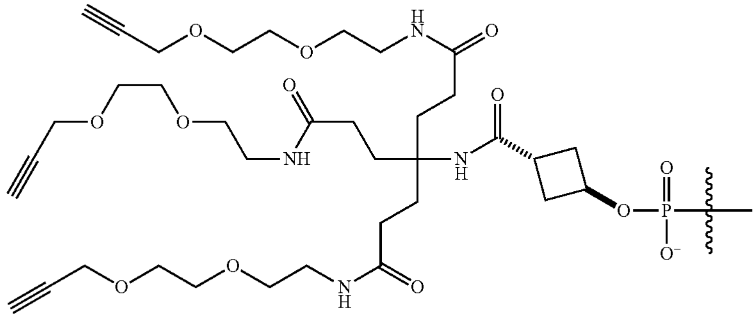 |
| (TriAlk11) |
| 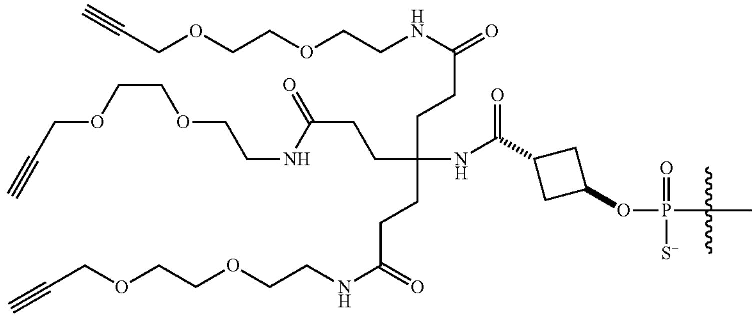 |
| (TriAlk11)s |
| 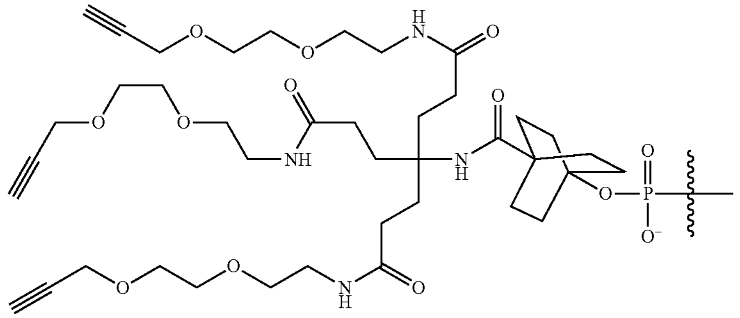 |
| (TriAlk12) |
| 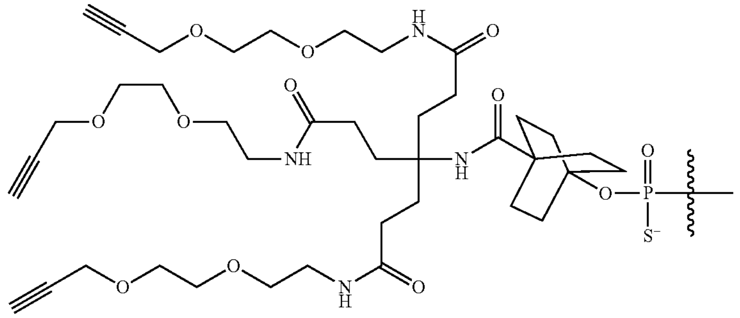 |
| (TriAlk12)s |

TABLE A-continued

Structures Representing Various Linking Groups and Scaffolds

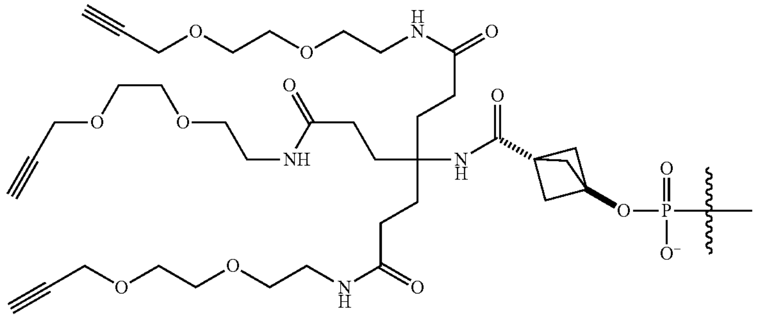

(TriAlk13)

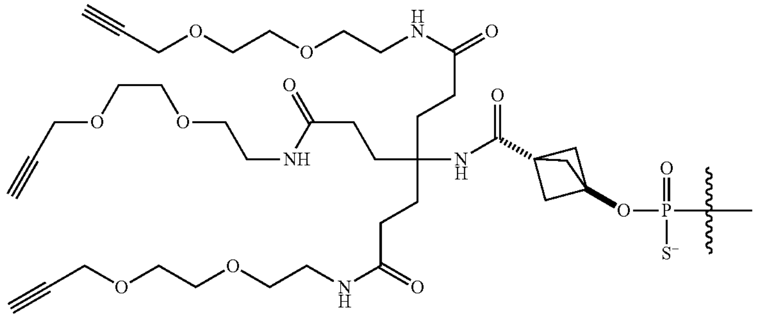

(TriAlk13)s

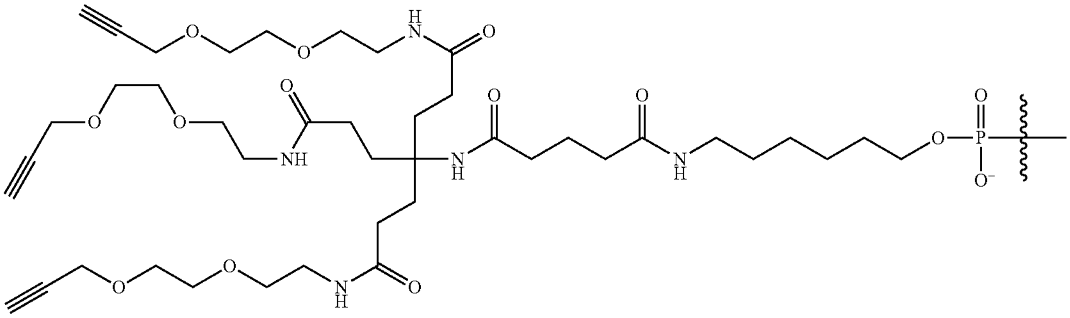

(TriAlk14)

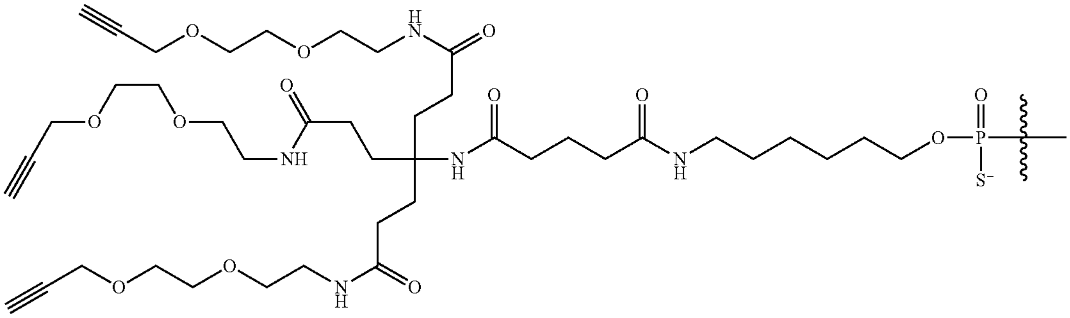

(TriAlk14)s wherein indicates the point of attachment to a cargo molecule.

Alternatively, other linking groups known in the art may be used. Examples of suitable linking groups are provided in PCT Application No. PCT/US19/18232, which is incorporated by reference herein in its entirety.

Internally Linked Targeting Ligands

In some embodiments when the integrin targeting ligands described herein are bound or linked to an RNAi molecule, the integrin targeting ligand may be bound to internal nucleotides of the sense strand or the antisense strand. In some embodiments, up to 15 targeting ligands may be conjugated to internal nucleotides on the sense strand of an RNAi agent. In some embodiments, 1, 2, 3, 4, 5, 6, 7, 8, 9, 10, 11, 12, 13, 14, or 15 targeting ligands may be conjugated to internal nucleotides on the sense strand of a HIF-2 alpha RNAi agent. In some embodiments, 1 to 5 (e.g., 1, 2, 3, 4, or 5) targeting ligands are conjugated to internal nucleotides on the sense strand of an RNAi agent. In some embodiments, 3 to 4 targeting ligands are conjugated to internal nucleotides on the sense strand of an RNAi agent.

In some embodiments, placement of internal targeting ligands may impact the efficacy or potency of an RNAi agent. In some embodiments of αvβ3 integrin targeting ligands bound to RNAi agents, a targeting group is conjugated to the 5' end of the sense strand, and at least 10 nucleotides are positioned between the tridentate targeting group located on the 5' end of the sense strand and the next closest targeting ligand located on the sense strand. In some embodiments, at least 5 nucleotides are positioned between the tridentate targeting group located on the 5' end of the sense strand and the next closest targeting ligand located on the sense strand.

In some embodiments where two or more targeting ligands are conjugated to internal nucleotides located on the sense strand of an RNAi agent, there is a space of at least one nucleotide that is not conjugated to a targeting ligand positioned between the two internal nucleotides that are conjugated to targeting ligands. In some embodiments where two or more targeting ligands are conjugated to the sense strand of an RNAi agent, at least two nucleotides that are not conjugated to a targeting ligand are positioned between two internal nucleotides that are conjugated to targeting ligands.

In some embodiments, targeting ligands are conjugated to the 2nd, 4th, and 6th nucleotides on the sense strand as numbered from 3' to 5', starting from the farthest 3' nucleotide that forms a base pair with a nucleotide on the antisense strand. In some embodiments, targeting ligands are conjugated to the 2nd, 4th, 6th, and 8th nucleotides (3'→5') from the 3' terminal nucleotide on the sense strand that forms a base pair with the antisense strand.

Examples of modified nucleotides for attaching internal targeting ligands are shown in Table B below:

TABLE B

| Structures Representing Modified Nucleotides for Attaching Targeting Ligands. |
|---|
| 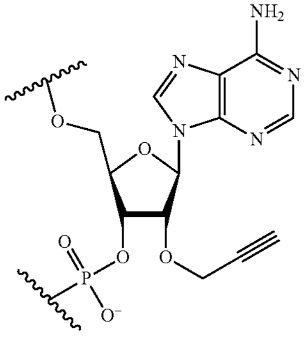 aAlk |

TABLE B-continued

| Structures Representing Modified Nucleotides for Attaching Targeting Ligands. |
|---|
| 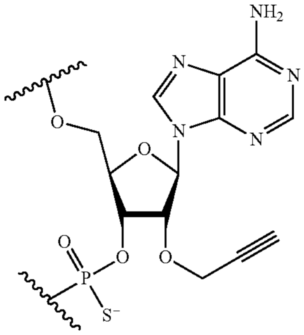 aAlks |
| 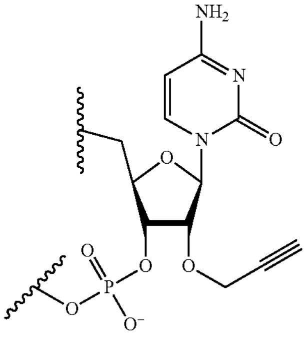 cAlk |
| 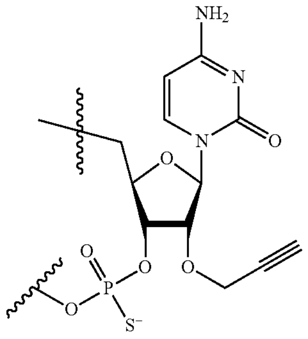 cAlks |
| 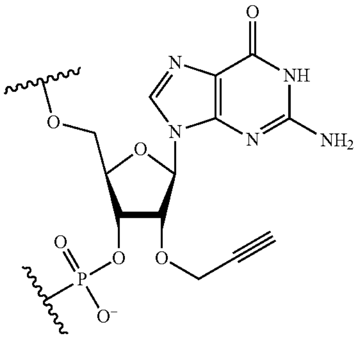 gAlk |

TABLE B-continued

Structures Representing Modified Nucleotides for Attaching Targeting Ligands.

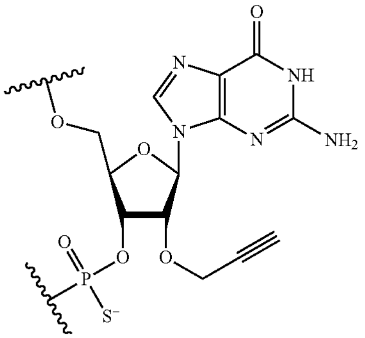

gAlks

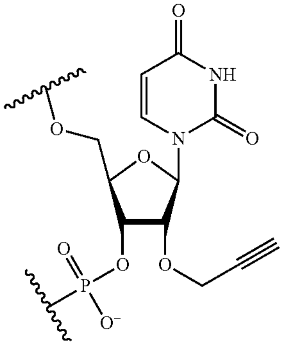

uAlk

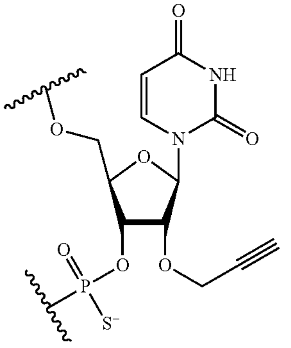

aAlks

The above provided embodiments and items are now illustrated with the following, non-limiting examples.

EXAMPLES

The following examples are not limiting and are intended to illustrate certain embodiments disclosed herein.

Example 1. Synthesis of Integrin Targeting Ligands

Some of the abbreviations used in the following experimental details of the synthesis of the examples are defined as follows: h or hr=hour(s); min=minute(s); mol=mole(s); mmol=millimole(s); M=molar; M=micromolar; g=gram(s); g=microgram(s); rt or RT=room temperature; L=liter(s); mL=milliliter(s); wt=weight; $Et_2O$=diethyl ether; THF=tetrahydrofuran; DMSO=dimethyl sulfoxide; EtOAc=ethyl acetate; $Et_3N$ or TEA=triethylamine; i-$Pr_2NEt$ or DIPEA or DIEA=diisopropylethylamine; $CH_2Cl_2$ or DCM=methylene chloride; $CHCl_3$=chloroform; $CDCl_3$=deuterated chloroform; $CCl_4$=carbon tetrachloride; MeOH=methanol; EtOH=ethanol; DMF=dimethylformamide; BOC=t-butoxycarbonyl; CBZ=benzyloxycarbonyl; TBS=t-butyldimethylsilyl; TBSCl or TBDMSCl=t-butyldimethylsilyl chloride; TFA=trifluoroacetic acid; DMAP=4-dimethylaminopyridine; $NaN_3$=sodium azide; $Na_2SO_4$=sodium sulfate; $NaHCO_3$=sodium bicarbonate; NaOH=sodium hydroxide; $MgSO_4$=magnesium sulfate; $K_2CO_3$=potassium carbonate; KOH=potassium hydroxide; $NH_4OH$=ammonium hydroxide; $NH_4Cl$=ammonium chloride; $SiO_2$=silica; Pd—C=palladium on carbon; HCl=hydrogen chloride or hydrochloric acid; NMM=N-methylmorpholine; $H_2$=hydrogen gas; KF=potassium fluoride; EDC-HCl=N-(3-Dimethylaminopropyl)-N'-ethylcarbodiimide hydrochloride; MTBE=methyl-tert-butyl ether; MeOH=methanol; Ar=argon; $N_2$=nitrogen; $SiO_2$=silica; $R_T$=retention time; PTSA=para-toluenesulfonic acid; PPTS=pyridinium para-toluenesulfonate.

a. Synthesis of Structure 4.1c (Compound 78)

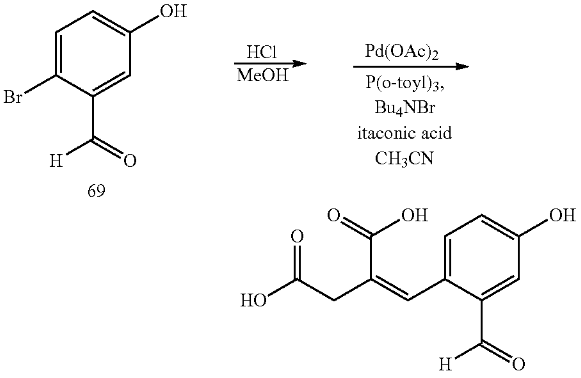

69

70

Compound 70 was prepared and isolated as described by Wallace et al., 8 Organic Process Research & Development 738-743 (2004).

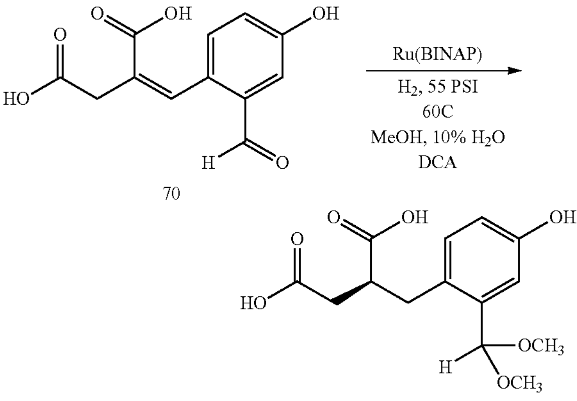

70

71

Compound 71 repared and isolated as described by Wallace et al., 8 Organic Process Research & Development 738-743 (2004), using commercially available ruthenium BINAP catalyst (CAS #199684-47-4) at 55 PSI H2.

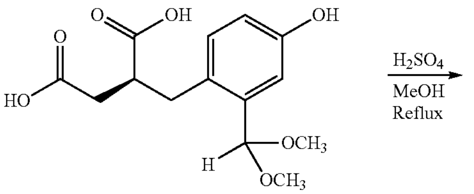

71

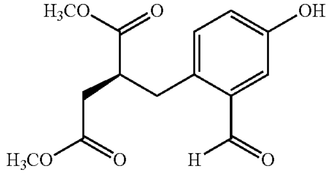

72

Compound 71 was treated with $H_2SO_4$ in MeOH at reflux for 17 hours. Upon completion, all volatiles were removed on rotary evaporator and compound 72 was isolated over silica eluting a gradient of ethyl acetate in hexanes.

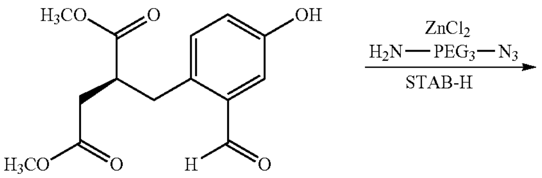

72

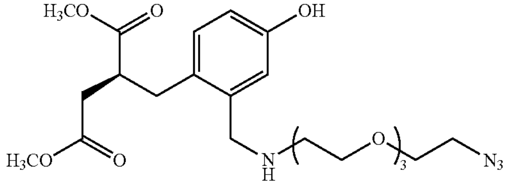

73

To mixture of compound 72 and $H_2N$-$PEG_3$-$N_3$ was added acetonitrile followed by $ZnCl_2$. The suspension was refluxed for 3 hours. The suspension was subsequently cooled, treated with a solution of STAB-H in DMAC and stirred for 16 hours. Upon completion, the reaction was quenched by addition of saturated aqueous sodium bicarbonate. The organic phase was diluted with 6 volumes of ethyl acetate and separated. The aqueous phase was back extracted once with 2 volumes of ethyl acetate. The organic phases were combined, dried over sodium sulfate, filtered and concentrated. Compound 73 was isolated by separation over silica eluting an isocratic mixture of DCM:EtOAc: MeOH:TEA (48:48:3:1).

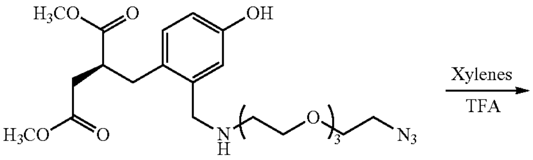

73

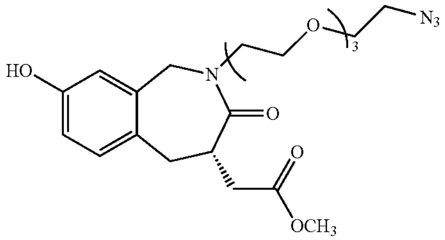

74

To compound 73 in a mixture of xylenes and DMAC was added TFA and was heated to reflux for 18 hours. Upon completion, all volatiles were removed on rotary evaporator and compound 74 was isolated over silica eluting an isocratic mixture of 1:1 DCM and ethyl acetate.

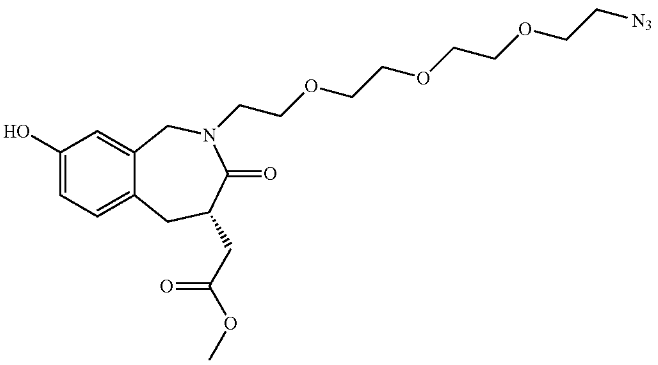

74

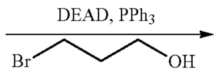

63

-continued

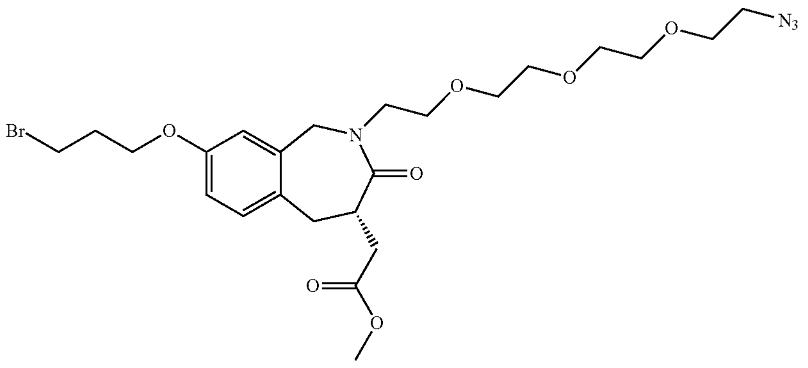

75

To a solution of triphenylphosphine (262 mg, 1.0 mmol) in THF (750 μL) was added diethyl azodicarboxylate solution (40 wt. % in toluene, 455 μL, 1.0 mmol)) at 0° C. The mixture was added to a neat mixture of compound 74 (150 mg, 0.33 mmol) and compound 63 (3-bromo-1-propanol (185 mg, 1.33 mmol)). The cooling bath was removed, and the reaction mixture was stirred overnight at room temperature. The reaction mixture was concentrated under reduced pressure and purified by reverse phase HPLC (Phenomenex Gemini C18, 250×50 mm, 10 μm, 60 mL/min, 0.1% TFA in water/ACN, gradient elution). Yield of compound 75: 102 mg (54%).

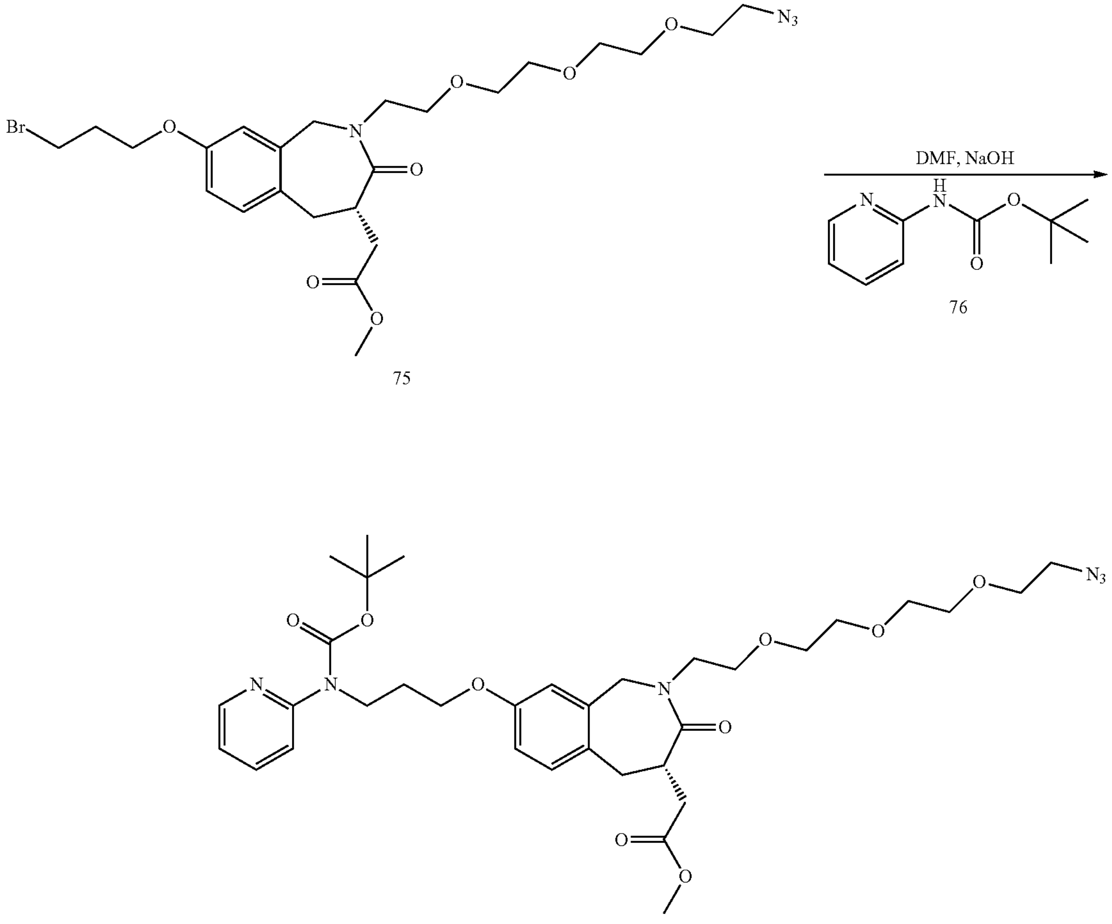

75

76

77

To a solution of compound 76 (2-(boc-amino)pyridine (42 mg, 0.21 mmol)) in DMF (500 μL) was added sodium hydride (60% dispersion in mineral oil, 7.9 mg, 0.20 mmol) at 0° C. The mixture was stirred at 0° C. for 30 minutes then added to a solution of compound 75 (102 mg, 0.18 mmol) in DMF (330 μL) dropwise at 0° C. The cooling bath was removed, and the reaction mixture was stirred overnight at room temperature. Residual compound 75 was detected by LCMS. To a solution of compound 76 (2-(boc-amino) pyridine (12.5 mg, 0.064 mmol)) in DMF (150 μL) was added sodium hydride (60% dispersion in mineral oil, 2.3 mg, 0.058 mmol) at 0° C. The mixture was stirred at 0° C. for 30 minutes then added to the reaction mixture. The cooling bath was removed, and the reaction mixture was stirred at room temperature for 3 hours. The reaction mixture was quenched with water (50 μL), concentrated under reduced pressure, and was used in the next step without further purification.

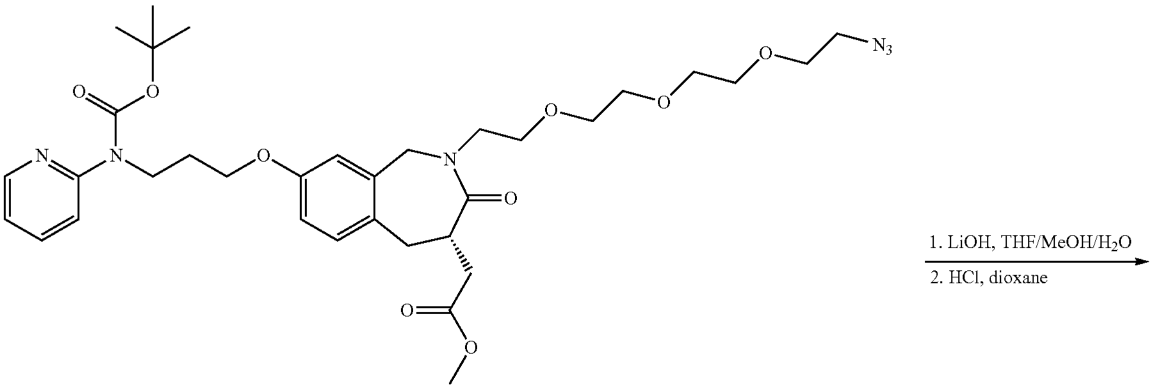

77

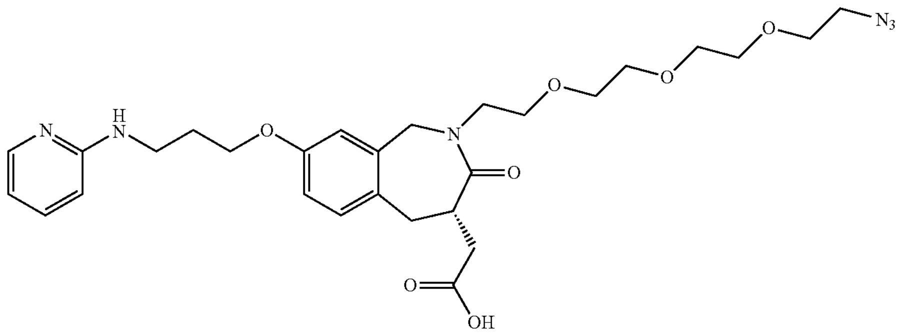

78

To a solution of compound 77 (122 mg, 0.18 mmol) in THF (732 μL) and methanol (732 μL) was added lithium hydroxide monohydrate (37 mg, 0.89 mmol) as a solution in water (366 μL). The reaction mixture was stirred at 40° C. for 1 hour and then concentrated under reduced pressure. To the residue was added HCl (4 M in dioxane, 2.2 mL, 8.9 mmol) and water (200 μL) at 0° C. The reaction mixture was warmed to room temperature. After stirring for 2 hours, the reaction mixture was concentrated under reduced pressure. The residue was purified by reverse phase HPLC (Phenomenex Gemini C18, 250×50 mm, 10 μm, 60 mL/min, 0.1% TFA in water/ACN, gradient elution). Yield of compound 78: 14 mg (14% over 3 steps).

b. Synthesis of Structure 4.2c (Compound 80)

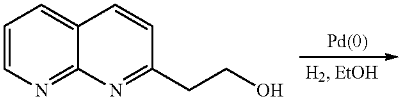

79a

-continued

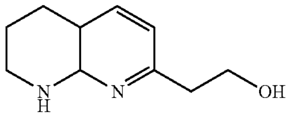

79b

To a solution containing compound 79a (commercially acquired) was added EtOH. The flask was charged with 1 atmosphere of $H_2$ and stirred at room temperature for 2 hours. Upon completion, the suspension was filtered over celite and the filtrate concentrated in vacuo. Compound 79b was isolated over silica eluting a gradient of MeOH in DCM containing 0.1% TEA.

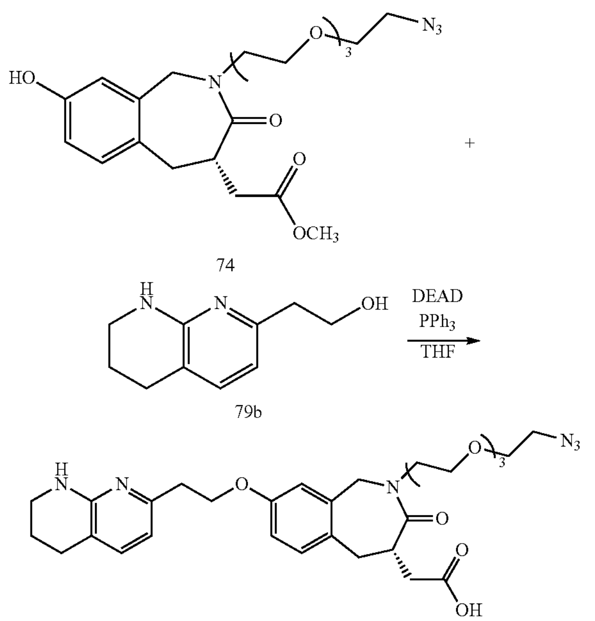

74

79b

80

To a solution of $PPh_3$ in THF was added dropwise a solution of DEAD at room temperature with vigorous stirring. The mixture was transferred to a vial containing a mixture of compound 74 and compound 79b, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous After stirring at room temperature for 1.5 hours, the mixture was acidified to a pH of 3 with $H_2SO_4$, concentrated, and purified by reverse phase HPLC (Phenomenex Gemini C18, 21.2x250 mm, 5 μm, 0.1% TFA in acetonitrile/water, gradient elution), yielding compound 80.

c. Synthesis of Structure 4.3c (Compound 84)

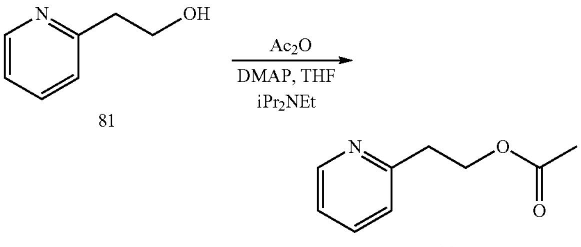

81

82

To a solution containing compound 81, DMAP and DIEA in THF was added $AC_2O$ dropwise at 0° C. The mixture was allowed to warm to room temperature and was stirred for 16 hours. Upon completion, all volatiles were removed on rotary evaporator and compound 82 was isolated by elution over a silica plug with ethyl acetate.

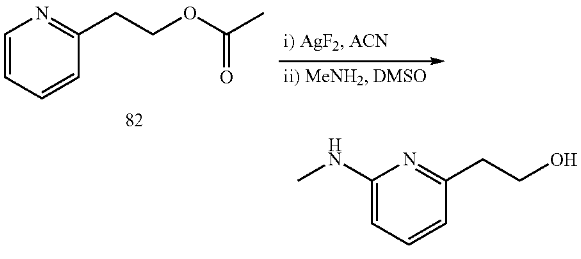

82

83

To a solution of compound 82 in acetonitrile was added silver fluoride portionwise, and the suspension was vigorously stirred for 1.5 hours. Upon completion, the suspension was filtered over a silica plug and the filtrate was concentrated. To the crude fluorinated intermediate was added DMSO then methylamine. The reaction vial was sealed and heated to 100° C. for 1 hour. Upon completion, the mixture was diluted with 10 volumes of EtOAc, washed once with saturated aqueous ammonium chloride, and the organic phase was separated. The separated aqueous was back extracted twice with EtOAc. The organic phases were combined, dried over sodium sulfate, filtered and concentrated. Compound 83 was isolated by separation over silica eluting an isocratic mixture of DCM:EtOAc:MeOH (48.75%:48.75%:2.5%).

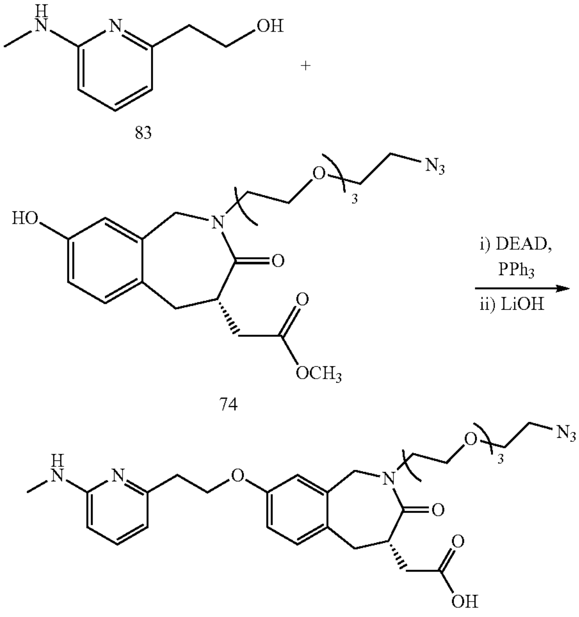

83

74

84

To a solution of $PPh_3$ in THF was added dropwise a solution of DEAD at room temperature with vigorous stirring. The mixture was transferred to a vial containing a mixture of compound 83 and compound 74, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous After stirring at room temperature for 1.5 hours, the mixture was acidified to a pH of 3 with $H_2SO_4$, concentrated, and purified by reverse phase HPLC (Phenomenex Gemini C18, 21.2×250 mm, 5 μm, 0.1% TFA in acetonitrile/water, gradient elution), yielding compound 84.

d. Synthesis of Structure 4.4c (Compound 90)

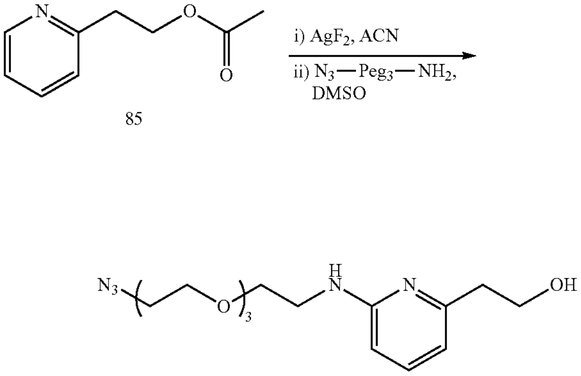

85

86

To a solution of compound 85 in acetonitrile at 0° C. was added portionwise silver fluoride. The suspension was stirred vigorously for 1.25 hours at room temperature. Upon completion, the suspension was filtered over a silica plug and the filtrate concentrated on rotary evaporator. To the crude fluorinated intermediate obtained was added DMSO, followed by $N_3$-$PEG_3$-$NH_2$. The vial was sealed and heated to 100° C. for 1 hour. Upon completion, the mixture was diluted with 10 volumes of EtOAc and washed with a 50:50 mixture of brine:saturated aqueous ammonium chloride and separated. The aqueous phase was back extracted twice with ethyl acetate. The combined organic phases were dried over sodium sulfate, filtered and concentrated. Compound 86 was isolated eluting a gradient of MeOH in DCM containing 1% TEA.

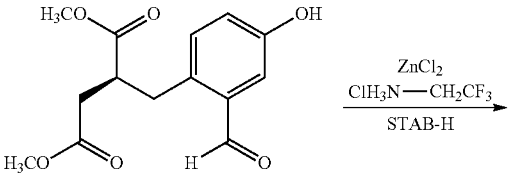

87

-continued

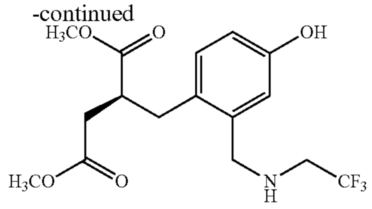

88

To mixture of compound 87 and trifluoroethylamine hydrochloride was added acetonitrile followed by $ZnCl_2$, and the suspension was refluxed for 3 hours. The suspension was subsequently cooled, treated with a solution of STAB-H in DMAC and stirred for 16 hours. Upon completion, the reaction was quenched by addition of saturated aqueous sodium bicarbonate. The organic phase was diluted with 6 volumes of ethyl acetate and separated. The aqueous phase was back extracted once with 2 volumes of ethyl acetate. The organic phases were combined, dried over sodium sulfate, filtered and concentrated. Compound 88 was isolated by separation over silica eluting an isocratic mixture of DCM:EtOAc:MeOH:TEA (48:48:3:1).

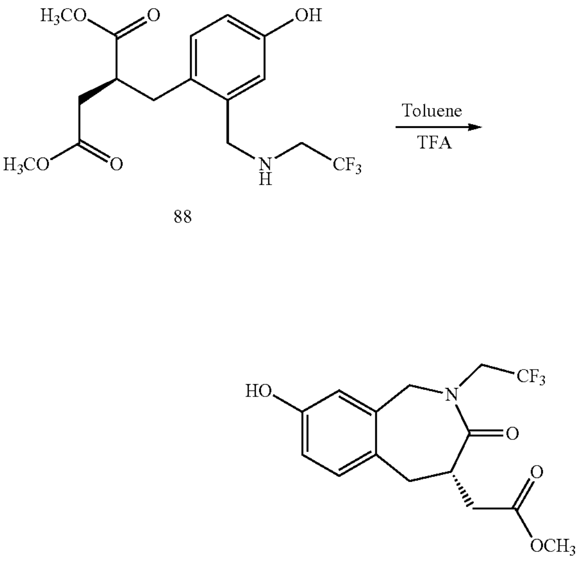

88

89

A solution of compound 87 in toluene was treated with TFA and heated to 120° C. in a sealed vial for 7 hours. Upon completion, all volatiles were removed and compound 88 was isolated eluting a gradient of ethyl acetate in hexanes.

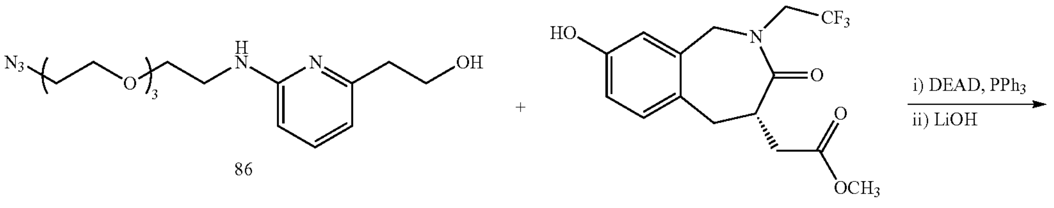

86

+

89

-continued

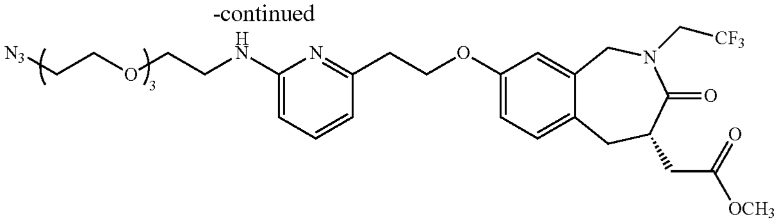

90

To a solution of $PPh_3$ in THF was added dropwise a solution of DEAD at room temperature with vigorous stirring. The mixture was transferred to a vial containing a mixture of compound 86 and compound 89, and the reaction mixture was stirred at room temperature overnight. Volatiles were removed from the reaction mixture and the crude was dissolved in EtOH. LiOH was added as a solution in $H_2O$, and additional water was added until the reaction mixture became homogeneous After stirring at room temperature for 1.5 hours, the mixture was acidified to a pH of 3 with $H_2SO_4$, concentrated, and purified by reverse phase HPLC (Phenomenex Gemini C18, 21.2×250 mm, 5 μm, 0.1% TFA in acetonitrile/water, gradient elution), yielding compound 90.

e. Synthesis of Structure 4.5c (Compound 94)

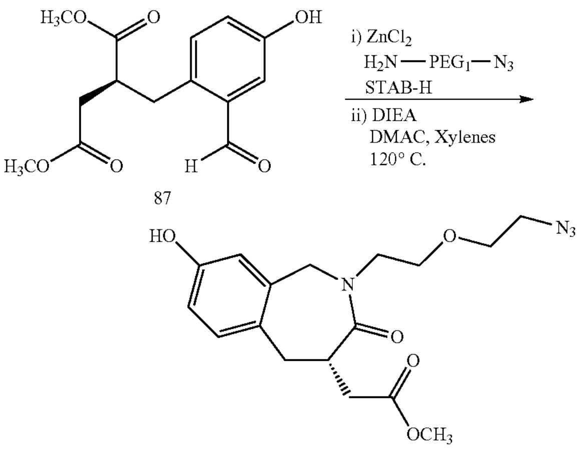

87

91

To mixture of compound 87 and $H_2N$-$PEG_1$-$N_3$ was added acetonitrile followed by $ZnCl_2$ and the suspension was refluxed for 3 hours. The suspension was subsequently cooled, treated with a solution of STAB-H in DMAC and stirred for 16 hours. Upon completion, the reaction was quenched by addition of saturated aqueous sodium bicarbonate. The organic phase was diluted with 6 volumes of ethyl acetate and separated. The basic aqueous layer was back extracted once with 2 volumes of ethyl acetate. The organics were combined, dried over sodium sulfate, filtered and concentrated.

The crude intermediate amine obtained was then subjected to base catalyzed cyclization as described for the synthesis of compound 89 in Example 1.14. Compound 91 was isolated using a Gemini C18 250×21.2 mm column eluting a gradient acetonitrile in $H_2O$ containing 0.1% TFA.

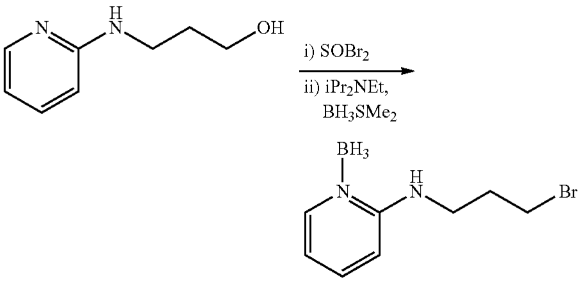

93

Compound 93 was prepared from compound 92 as described according to Zajac M. Et. Al. J. Org. Chem. 2008, 73, 6901.

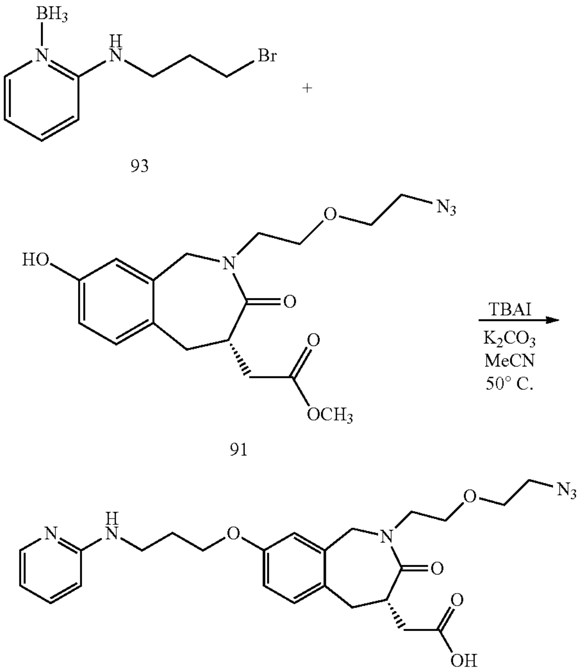

93

91

94

Compound 94 was prepared as described using modified procedures published as according to Zajac M. Et. Al. J. Org. Chem. 2008, 73, 6901. Compound 94 was isolated after de-esterfication by reverse phase HPLC (Phenomenex Gemini C18, 250×50 mm, 10 μm, 60 mL/min, 0.1% TFA in water/ACN, gradient elution).

f. Synthesis of Structure 4.6c (Compound 96)

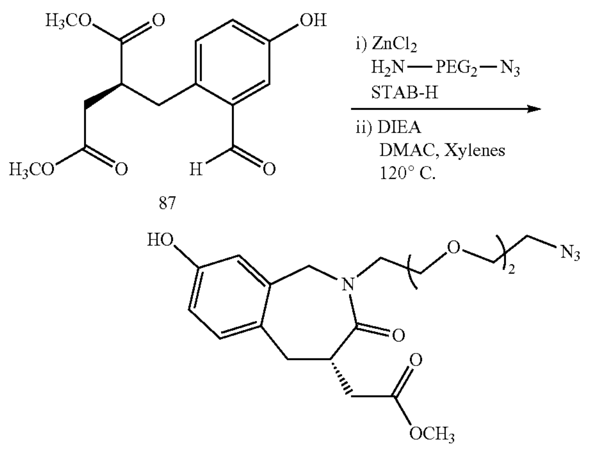

87

95

Compound 87 was reductively aminated with $H_2N$-$PEG_2$-azide as described in the synthesis of compound 88 in Example 1.14, above. The crude intermediate amine obtained was then subjected to base catalyzed cyclization, as described in synthesis of compound 89 in Example 1.14, above. Compound 95 was isolated reverse phase HPLC (Phenomenex Gemini C18, 250×50 mm, 10 μm, 60 mL/min, 0.1% TFA in water/ACN, gradient elution).

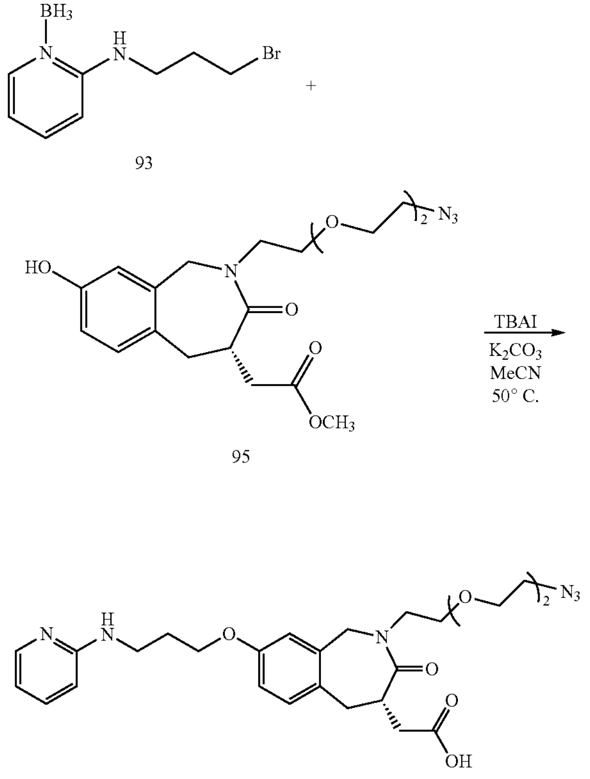

93

95

96

Compound 96 was prepared as described using modified procedures published as according to Zajac M. Et. Al. J. Org. Chem. 2008, 73, 6901. Compound 96 was isolated after de-esterfication by reverse phase HPLC (Phenomenex Gemini C18, 250×50 mm, 10 μm, 60 mL/min, 0.1% TFA in water/ACN, gradient elution).

g. Synthesis of Structure 4.8c (Compound 98)

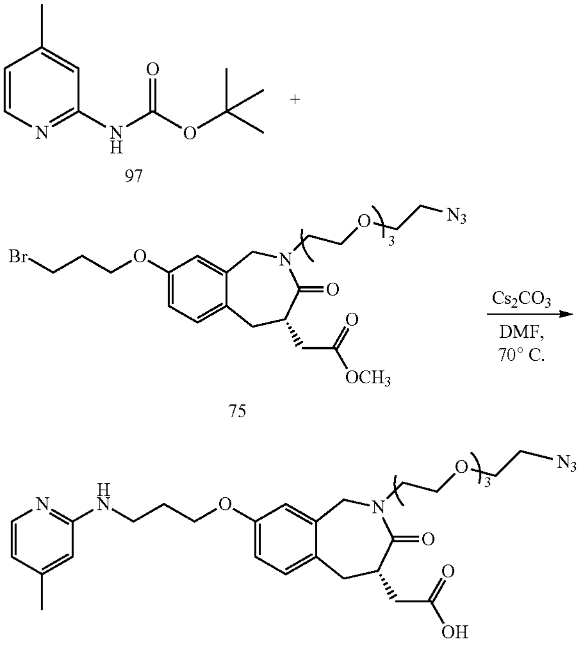

97

75

98

To a solution of compound 75 in DMF was added compound 97 followed by cesium carbonate, and the suspension was vigorously stirred at 70° C. for 4 hours. Upon completion, LiOH as a solution in $H_2O$ was added, THF was added to aid in solubility, and the solution was heated to 40° C. for 2 hours. Upon complete removal of carboxylate ester, the pH was neutralized with HCl. Subsequently, an additional 32 equivalents of HCl were added and the solution was stirred for 2 hours at 40° C. Upon completion, compound 98 was isolated by direct injection onto reverse phase HPLC (Phenomenex Gemini C18, 250×50 mm, 10 μm, 60 mL/min, 0.1% TFA in water/ACN, gradient elution).

h. Synthesis of Structure 4.9c (Compound 99)

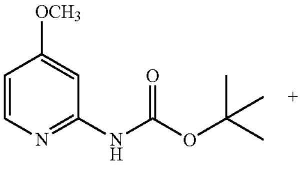

61

-continued

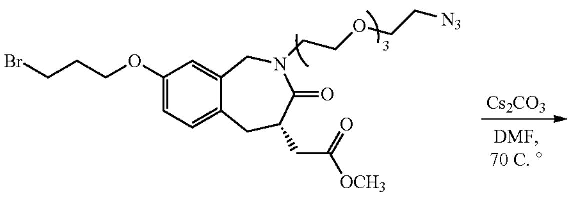

75

-continued

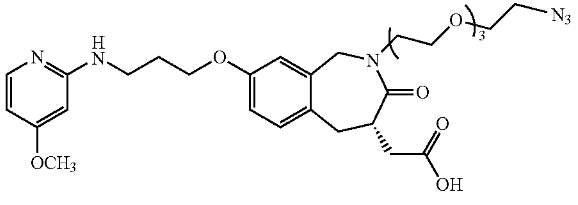

99

To a solution of compound 75 in DMF was added compound 61 followed by cesium carbonate, and the suspension was vigorously stirred at 70° C. for 4 hours. Upon completion, LiOH as a solution in $H_2O$ was added, THF was added to aid in solubility, and the solution was heated to 40° C. for 2 hours. Upon complete removal of carboxylate ester, the pH was neutralized with HCl. Subsequently an additional 32 equivalents of HCl were added and the solution was stirred for 2 hours at 40° C. Upon completion, compound 99 was isolated by direct injection onto reverse phase HPLC (Phenomenex Gemini C18, 250×50 mm, 10 μm, 60 mL/min, 0.1% TFA in water/ACN, gradient elution).

i. Synthesis of Structure 4.10c

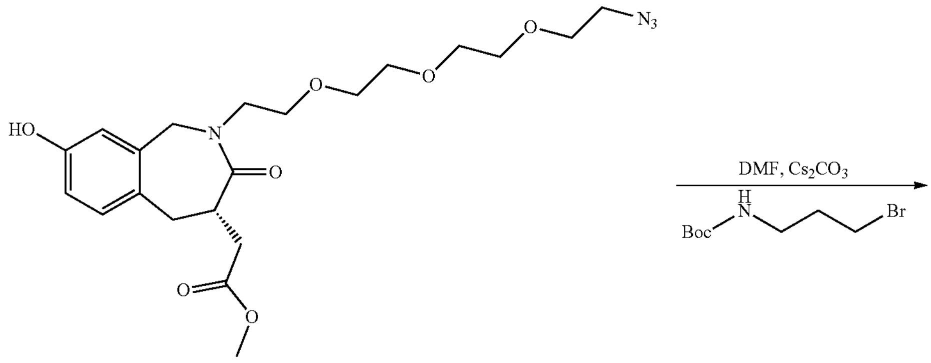

74

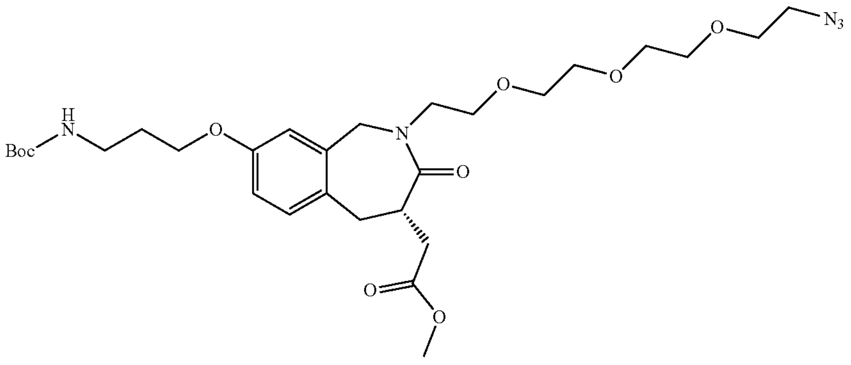

101

To a solution of compound 74 (250 mg, 0.55 mmol) and 3-(boc-amino)propyl bromide (264 mg, 1.11 mmol) in DMF (1 mL) was added cesium carbonate (362 mg, 1.11 mmol). The mixture was heated at 60° C. for 1 h. The reaction mixture was quenched with sat. aq. $NaHCO_3$ (2 mL) and extracted with EtOAc (3×10 mL). The combined organic phase was dried over $Na_2SO_4$, filtered, and concentrated. The residue was purified by CombiFlash using silica gel as the stationary phase and was eluted with a gradient of MeOH in DCM (0-5%). Yield of compound 101: 311 mg (92%). Mass calculated for $C_{29}H_{45}N_5O_9$ $[M+H]^+$: 608.33, found: 608.43.

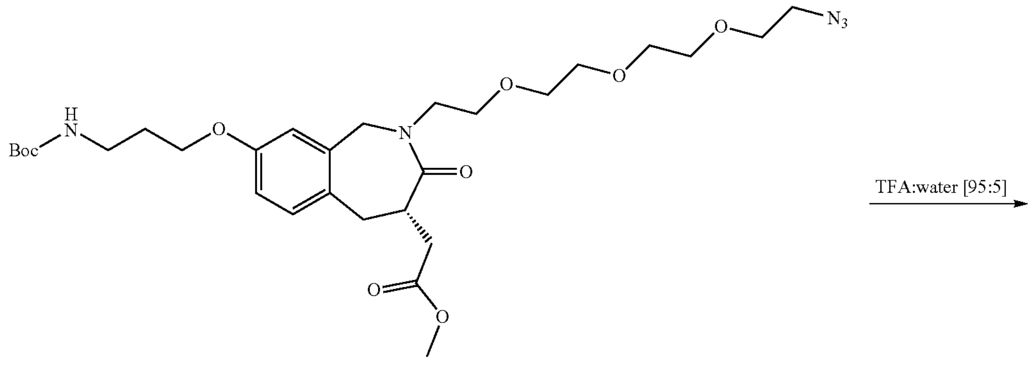

101

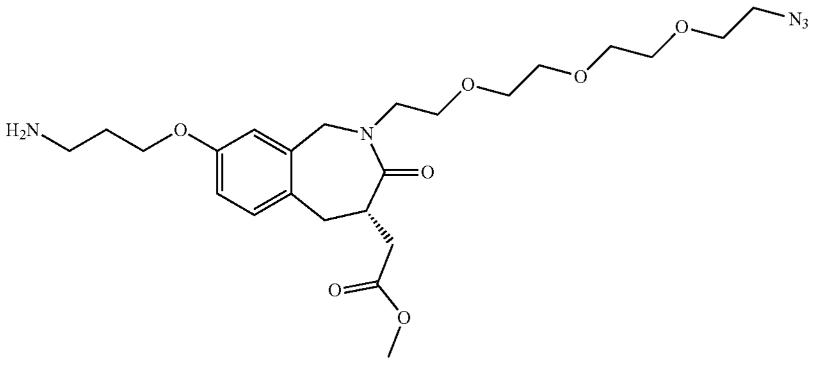

102

Compound 101 (311 mg, 0.51 mmol) was dissolved in TFA:water [95:5] (3 mL) and stirred at room temperature for 1 h. The reaction mixture was concentrated under reduced pressure. The residue was purified by CombiFlash using silica gel as the stationary phase and was eluted with a gradient of MeOH in DCM containing 1% triethylamine (0-5%). Based on $^1$H NMR, the product was contaminated with TFA*TEA salt. The mixture was dissolved in EtOAc (10 mL) and was washed with sat. aq. $NaHCO_3$ (5 mL). The aqueous phase was back extracted with EtOAc:butanol [3:1] (4×5 mL). The combined organic phase was dried over $Na_2SO_4$, filtered, and concentrated. Yield of compound 102: 178 mg (68%). Mass calculated for $C_{24}H_{37}N_5O_7$ $[M+H]^+$: 508.28, found: 508.69.

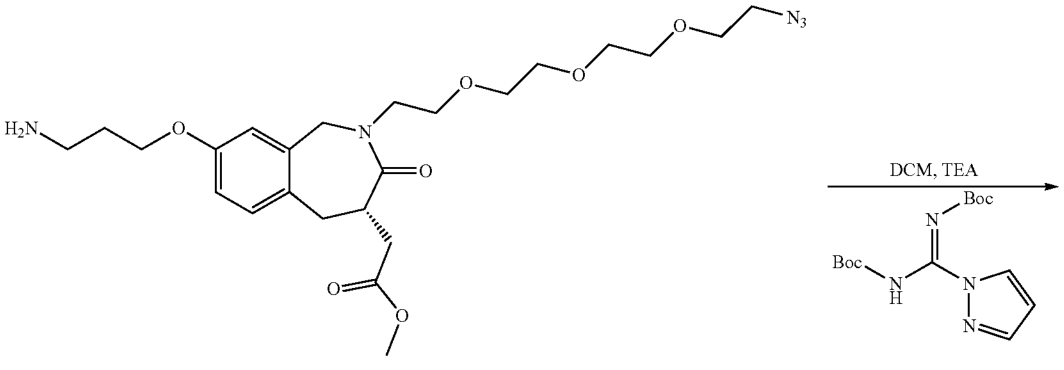

102

-continued

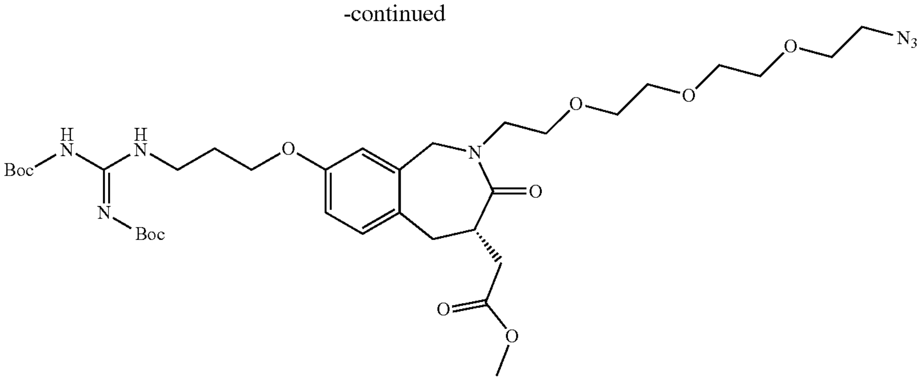

103

To a solution of compound 102 (40 mg, 0.079 mmol) and N,N-Di-Boc-H-pyrazole-1-carboxamidine (49 mg, 0.16 mmol) in DCM (400 μL) was added TEA (33 μL, 24 mg, 0.24 mmol). The reaction mixture was stirred at room temperature for 30 m. The reaction mixture was concentrated, and the residue was purified by CombiFlash® using silica gel as the stationary phase and was eluted with a gradient of MeOH in DCM (0-5%). Yield of compound 103: 45 mg (76%). Mass calculated for $C_{35}H_{55}N_7O_{11}$ $[M+H]^+$: 750.41, found: 750.58.

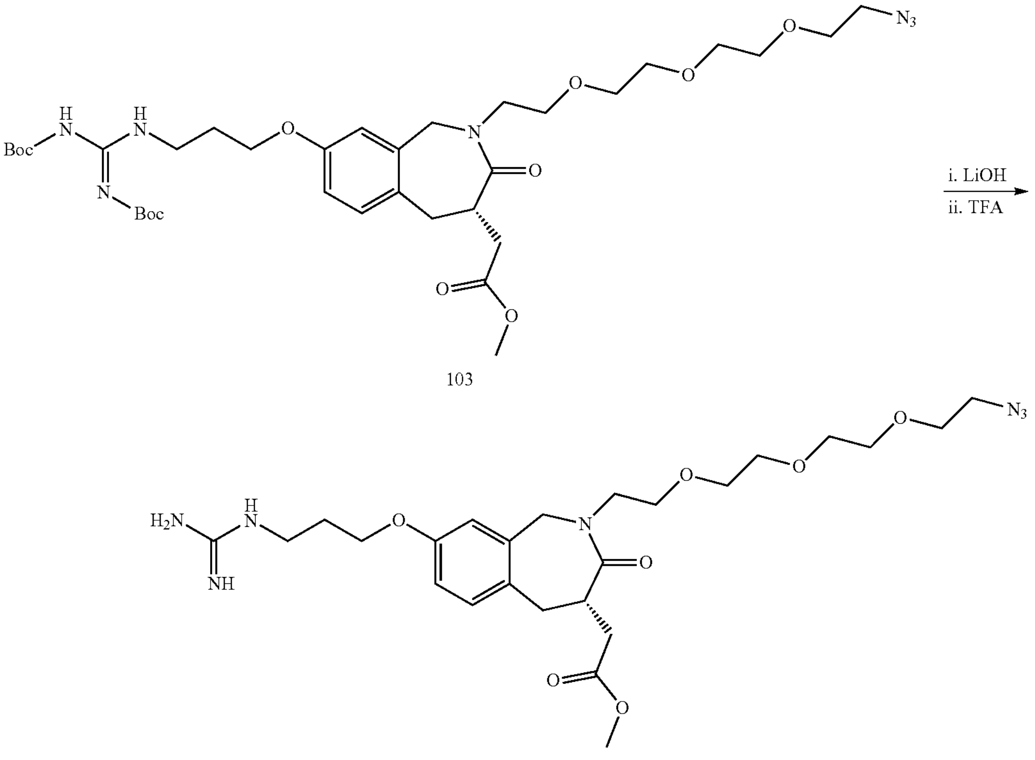

103

104

To a solution of compound 103 (43 mg, 0.057 mmol) in THF:water [1:1] (640 μL) was added LiOH (4.1 mg, 0.17 mmol). The mixture was stirred at room temperature for 1.5 h then acidified to pH=7 using 6 N HCl. The reaction mixture was concentrated under reduced pressure. The residue was dissolved in TFA:water [95:5] (430 μL) and stirred for 1.5 h at room temperature. The reaction mixture was concentrated, and the residue was purified by RP-HPLC (Phenomenex Gemini C18, 250×21.2 mm, 5 μm, water/ACN 0.1% TFA, 18-35% gradient). Yield of compound 104

(Structure 4.10c) as TFA salt: 32 mg (86%). Mass calculated for $C_{24}H_{37}N_7O_7$ $[M+H]^+$: 536.29, found: 536.42.

j. Synthesis of Structure 4.11c

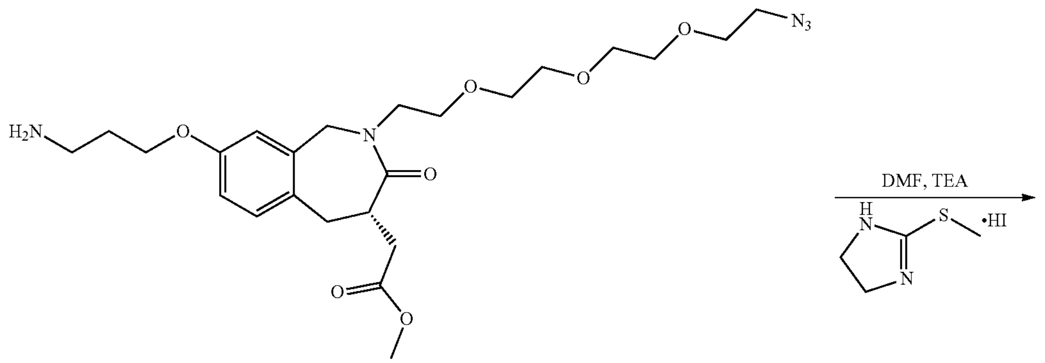

102

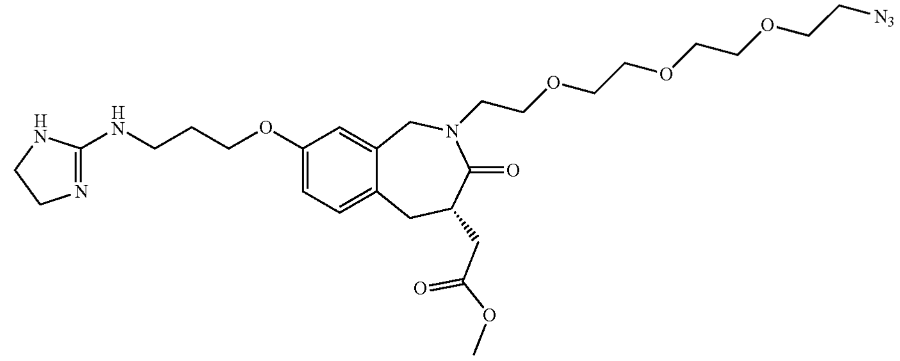

105

To a solution of compound 102 (35 mg, 0.069 mmol) and 2-methylthio-2-imidazoline hydriodide (84 mg, 0.34 mmol) in DMF (150 μL) was added triethylamine (72 μL, 52 mg, 0.52 mmol) at room temperature. The reaction mixture was stirred at 60° C. for 1 h, concentrated under reduced pressure, and used in the next step without further purification. Mass calculated for $C_{27}H_{41}N_7O_7$ $[M+H]^+$: 576.32, found: 576.48.

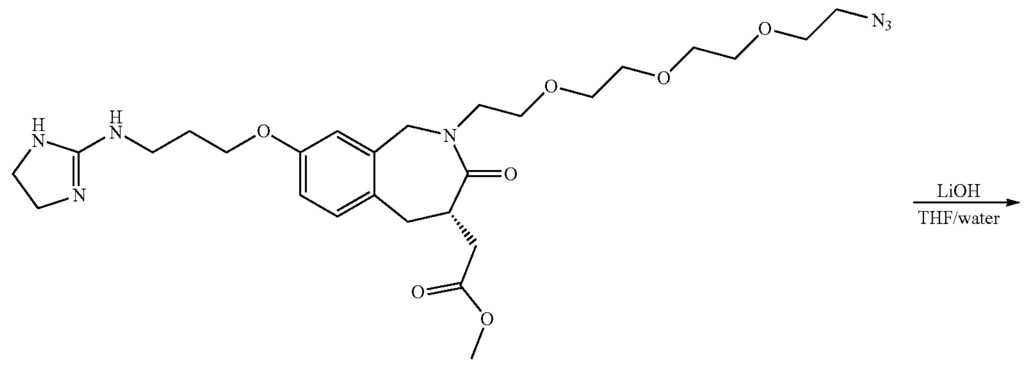

105

-continued

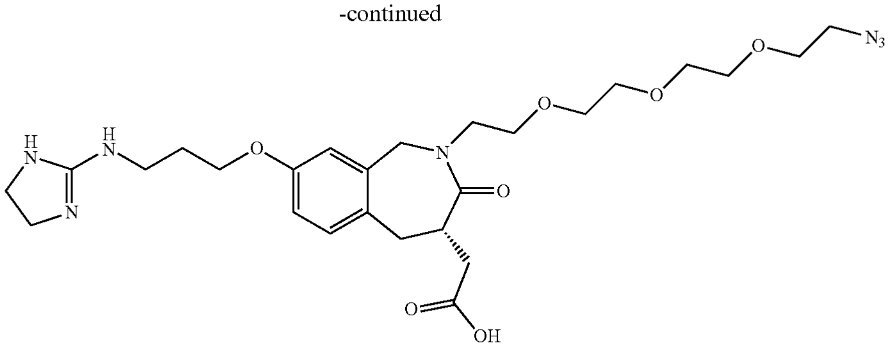

106

To a solution of compound 105 (36 mg, 0.063 mmol) in THF (270 μL) and water (135 μL) was added LiOH (9.0 mg, 0.38 mmol) as a solution in water (135 μL). The reaction mixture was heated at 50° C. for 30 m then acidified to pH=7 using 6 N HCl. The mixture was concentrated under reduced pressure. The residue was purified by RP-HPLC (Phenomenex Gemini C18, 250×21.2 mm, 5 μm, water/ACN 0.1% TFA, 18-35% gradient). Yield of compound 106 as TFA salt (Structure 4.11c): 25 mg (58%). Mass calculated for $C_{26}H_{39}N_7O_7$ $[M+H]^+$: 562.30, found: 562.52.

k. Synthesis of Structure 4.12c

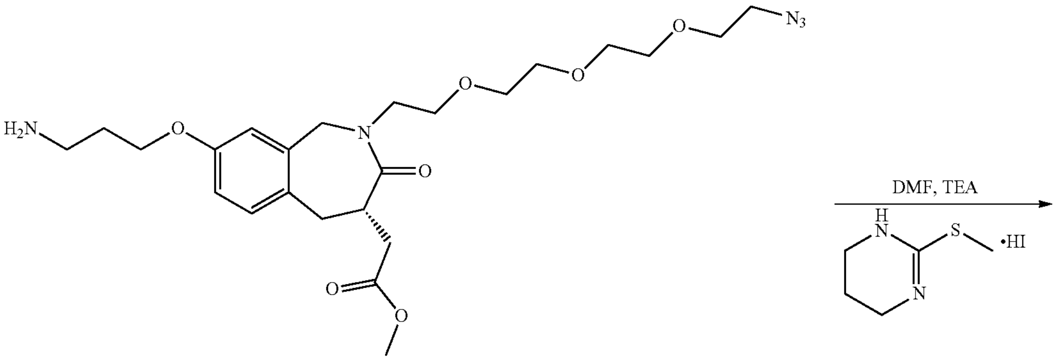

102

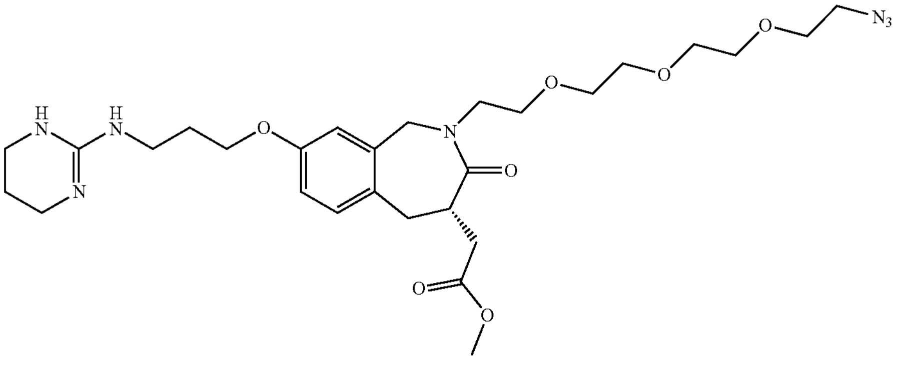

107

To a solution of compound 102 (45 mg, 0.089 mmol) and 2-(methylthio)-1,4,5,6-tetrahydropyrimidine hydroiodide (46 mg, 0.18 mmol) in DMF (200 μL) was added TEA (37 μL, 27 mg, 0.27 mmol). The reaction mixture was stirred at rt for 1 h then 60° C. for 1.5 h. Additional 2-(methylthio)-1,4,5,6-tetrahydropyrimidine hydroiodide (69 mg, 0.27 mmol) and TEA (56 μL, 41 mg, 0.41 mmol) were added and the reaction mixture was stirred for an additional 6 h at 60° C. The reaction mixture was concentrated and used in the next step without further purification. Mass calculated for $C_{28}H_{43}N_7O_7$ $[M+H]^+$: 590.33, found: 590.43.

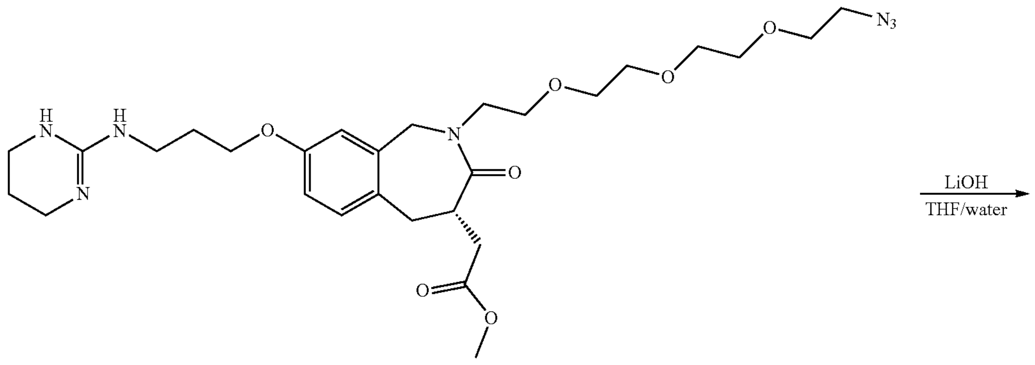

107

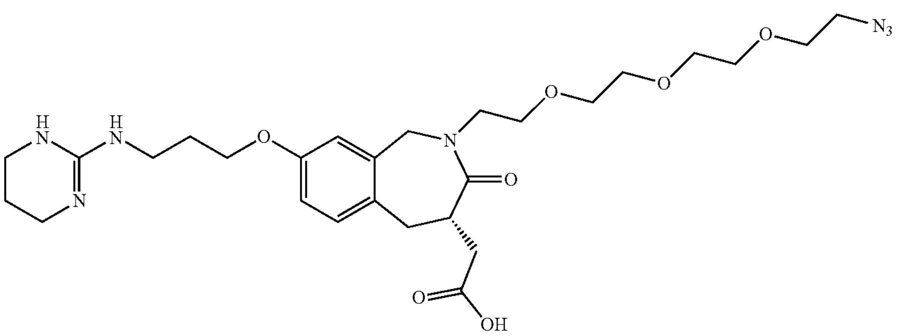

108

To a solution of compound 107 (52 mg, 0.088 mmol) in THF:water [1:1] (780 μL) was added LiOH (6.3 mg, 0.26 mmol). The reaction mixture was heated at 40° C. for 16 h. Additional LiOH (6.3 mg, 0.26 mmol) was added and the reaction mixture was heated at 50° C. for 1.5 h. The reaction mixture was acidified to pH=7 using 6 N HCl and concentrated. The residue was purified by RP-HPLC (Phenomenex Gemini C18, 250×21.2 mm, 5 μm, water/ACN 0.1% TFA, 18-35% gradient). Yield of compound 108 (Structure 4.12c) as TFA salt: 25 mg (41%). Mass calculated for $C_{27}H_{41}N_7O_7$ $[M+H]^+$: 576.32, found: 576.39.

1. Synthesis of Structure 4.13c

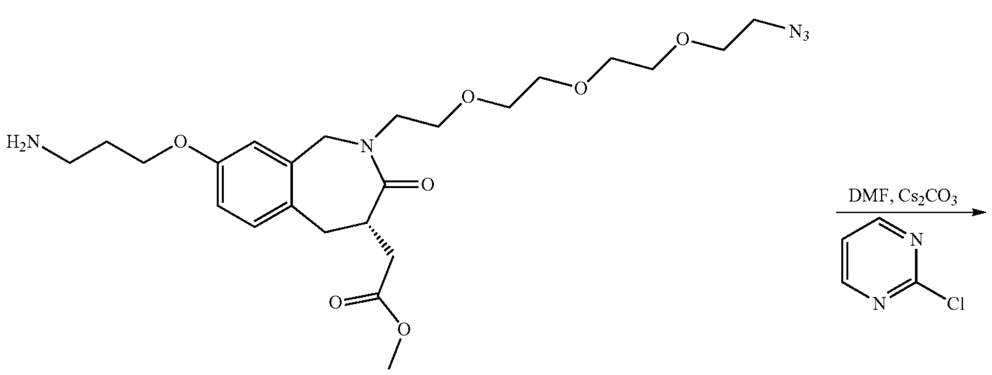

102

-continued

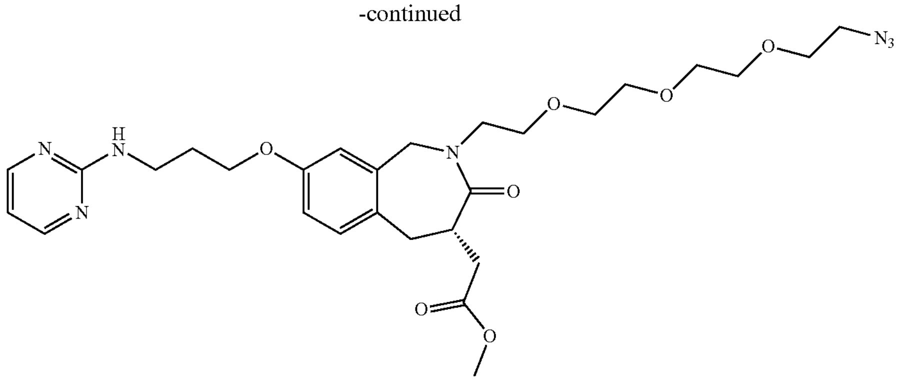

109

To a solution of compound 102 (20 mg, 0.039 mmol) and 2-chloro pyrimidine (4.8 mg, 0.042 mmol) in DMF (100 μL) was added cesium carbonate (26 mg, 0.079 mmol). The reaction mixture was heated at 70° C. for 2.5 h. The reaction mixture was concentrated and used in the next step without further purification. Mass calculated for $C_2H_{39}N_7O_7$ $[M+H]^+$: 586.30, found: 586.29.

Example 2. Synthesis of Tridentate Integrin Targeting Ligands, RNAi Agents, and Conjugation of Integrin Targeting Ligands to Cargo Molecules (RNAi Agents)

The integrin targeting ligands can be conjugated to one or more RNAi agents useful for inhibiting the expression of

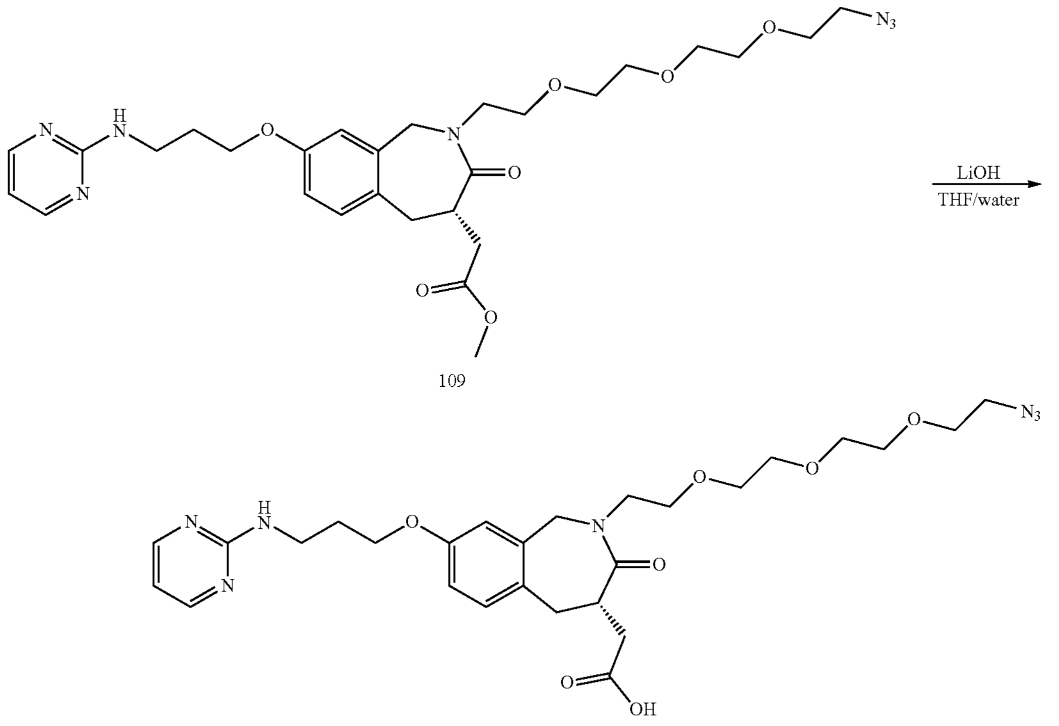

109

110

To a solution of compound 109 (23 mg, 0.039 mmol) in THF:water [1:1] (200 μL) was added LiOH (2.8 mg, 0.12 mmol). The reaction mixture was heated at 40° C. for 1 h then acidified to pH=6 using 6 M HCl. The reaction mixture was concentrated and purified by RP-HPLC (Phenomenex Gemini C18, 250×21.2 mm, 5 μm, water/ACN 0.1% TFA, 20-40% gradient). Yield of compound 110 (Structure 4.13c): 16 mg (73%). Mass calculated for $C_{27}H_{37}N_7O_7$ $[M+H]^+$: 572.29, found: 572.43.

one or more targeted genes in cells that express integrins. The integrin targeting ligands disclosed herein facilitate the delivery of the RNAi agents to the targeted cells and/or tissues. Example 1, above, described the synthesis of certain integrin targeting ligands disclosed herein. The following describes the general procedures for the syntheses of certain integrin targeting ligand-RNAi agent conjugates that are illustrated in the non-limiting Examples set forth herein.

A. Synthesis of RNAi Agents.

RNAi agents can be synthesized using methods generally known in the art. For the synthesis of the RNAi agents illustrated in the Examples set forth herein, the sense and antisense strands of the RNAi agents were synthesized according to phosphoramidite technology on solid phase used in oligonucleotide synthesis. Depending on the scale, a MerMade96E® (Bioautomation), a MerMadel2® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the following 2'-O-methyl phosphoramidites were used: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-dimethoxytrityl-2'-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. TFA aminolink phosphoramidites were also commercially purchased (ThermoFisher).

In some examples, the integrin targeting ligands disclosed herein are conjugated to the RNAi agents by linking the components to a scaffold that includes a tri-alkyne group, or to a modified nucleotide comprising a propargyl group as shown in Table B, above. In some examples, the tri-alkyne group is added by using a tri-alkyne-containing phosphoramidite, which can be added at the 5' terminal end of the sense strand of an RNAi agent. When used in connection with the RNAi agents presented in certain Examples herein, tri-alkyne-containing phosphoramidites were dissolved in anhydrous dichloromethane or anhydrous acetonitrile (50 mM), while all other amidites were dissolved in anhydrous acetonitrile (50 mM), and molecular sieves (3A) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 90 sec (2' O-Me), and 60 sec (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

Alternatively, where the integrin targeting ligands are conjugated to the RNAi agents via a tri-alkyne scaffold, instead of using a phosphoramidite approach, tri-alkyne-containing compounds can be introduced post-synthetically (see, for example, section E, below). When used in connection with the RNAi agents presented in certain Examples set forth herein, when attaching a tri-alkyne group post-synthetically to the 5' end of the sense strand the 5' terminal nucleotide of the sense strand was functionalized with a nucleotide that included a primary amine at the 5' end to facilitate attachment to the tri-alkyne-containing scaffold. TFA aminolink phosphoramidite was dissolved in anhydrous acetonitrile (50 mM) and molecular sieves (3A) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 min (RNA), 90 sec (2' O-Me), and 60 sec (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

In the examples set forth herein, the following shows the modified nucleotide sequence for the duplexes synthesized:

```
Duplex AD04545:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 2)
(NH2-C6)scsaacguaaCfGfAfuuucaugaasa(invAb)

Duplex AD04546:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 3)
(NH2-C6)scsaacguaaCfGfAfuuucaugaasa(invAb)(C6-S-
Mal-L)

Duplex AD05614:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 4)
(TriAlk1)scsaacguaaCfGfAfuuucaugaasa(invAb)(6-S-
Mal-L)

Duplex AD05615:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 5)
(TriAlk2)scsaacguaaCfGfAfuuucaugaasa(invAb)(6-S-
Mal-L)

Duplex AD05616:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 6)
(TriAlk3)scsaacguaaCfGfAfuuucaugaasa(invAb)(6-S-
Mal-L)
```

-continued

```
Duplex AD05617:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 7)
(TriAlk6)scsaacguaaCfGfAfuuucaugaasa(invAb)(6-S-

Mal-L)

Duplex AD05620:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 8)
(TriAlk4)scsaacguaaCfGfAfuuucaugaasa(invAb)(6-S-

Mal-L)

Duplex AD05971:
Modified Antisense Strand Sequence (5' → 3):
                                        (SEQ ID NO: 1)
usUfsusCfaUfgAfaAfuCfgUfuAfcGfuUfsg

Modified Sense Strand Sequence (5' → 3):
                                        (SEQ ID NO: 9)
(NH2-C6)scsaacguaaCfGfAfuuuAlkcaAlkugAlkaaAlksa

(invAb)(C6-S-Mal-C18 diacid moiety)
```

For the modified nucleotide sequences listed above, a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; aAlk, cAlk, gAlk, and uAlk represent 2'-O-propargyl adenosine, cytidine, guanosine, or uridine, respectively; (invAb) represents an inverted abasic residue (inverted abasic deoxyribonucleotide); s represents a phosphorothioate linkage; (NH2-C6)s represents:

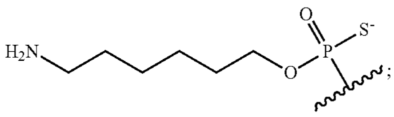 [SMILES: *P(=O)([S-])OCCCCCCN]

;

and (C6-S-Mal-L) represents:

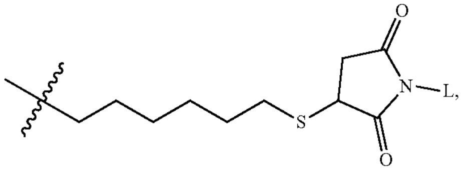

, and 6-S-Mal-L represents:

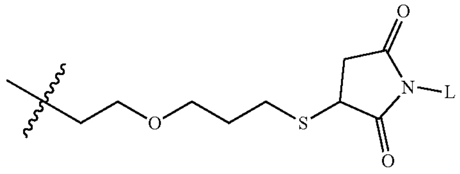

wherein L is a PEG chain, or ethyl, as indicated in the examples below. For the embodiments herein, when viewing the respective strand 5'→3', the inverted abasics are inserted such that the 3' position of the deoxyribose is linked at the 3' end of the preceding monomer on the respective strand.

Structures for "TriAlk1," TriAlk2," "TriAlk3," "TriAlk4," and TriAlk6," are shown in Table A above. Each trialkyne linking agent was functionalized with three integrin ligands as shown in the respective examples, according to the procedures in Example 2 below.

B. Cleavage and Deprotection of Support Bound Oligomer.

After finalization of the solid phase synthesis, the dried solid support was treated with a 1:1 volume solution of 40 wt. % methylamnine in water and 28% to 319% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5 PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate. pH 6.7 and 20% Acetonitrile or filtered water.

D. Annealing.

Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. The conversion factor used was either 0.037 mg/(mL·cm), or, alternatively for some experiments, a conversion factor was calculated from an experimentally determined extinction coefficient.

E. Conjugation of Tri-Alkyne Scaffold.

Either prior to or after annealing, the 5' or 3' amine functionalized sense strand of an RNAi agent can be conjugated to a tri-alkyne scaffold. Example tri-alkyne scaffold structures that can be used in forming the constructs disclosed herein include the following:

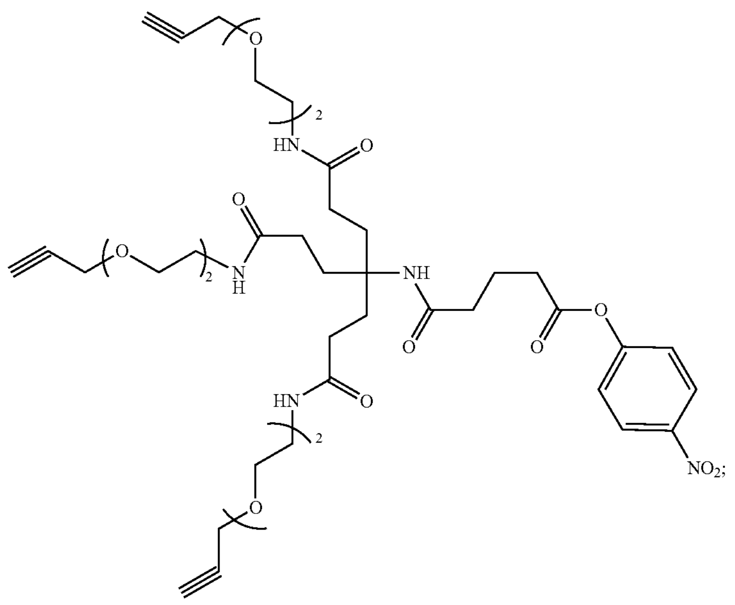
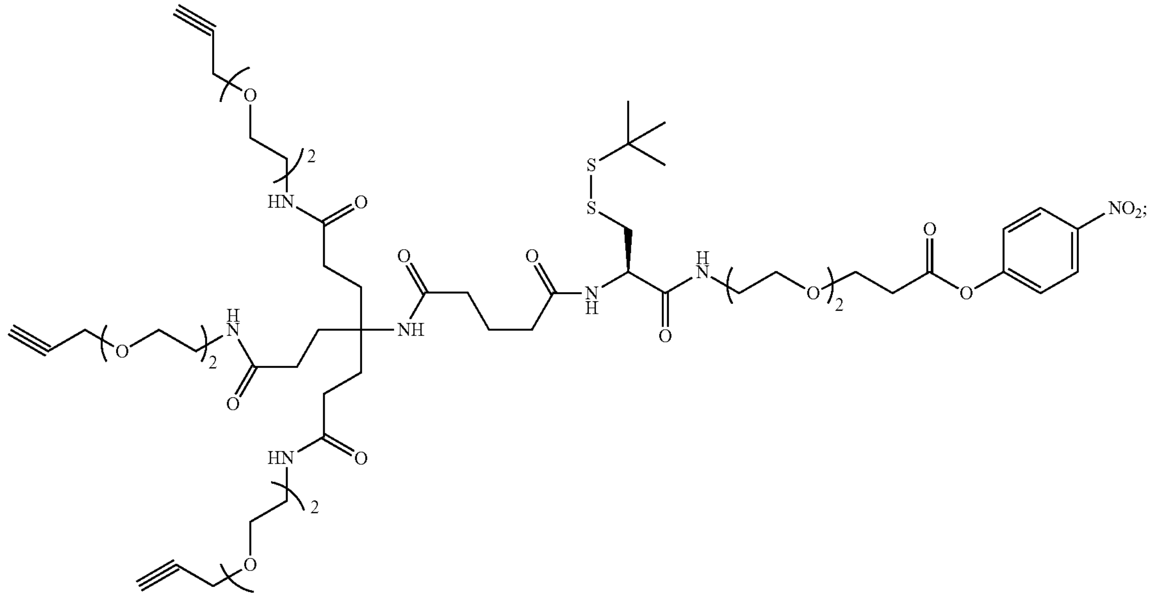

-continued

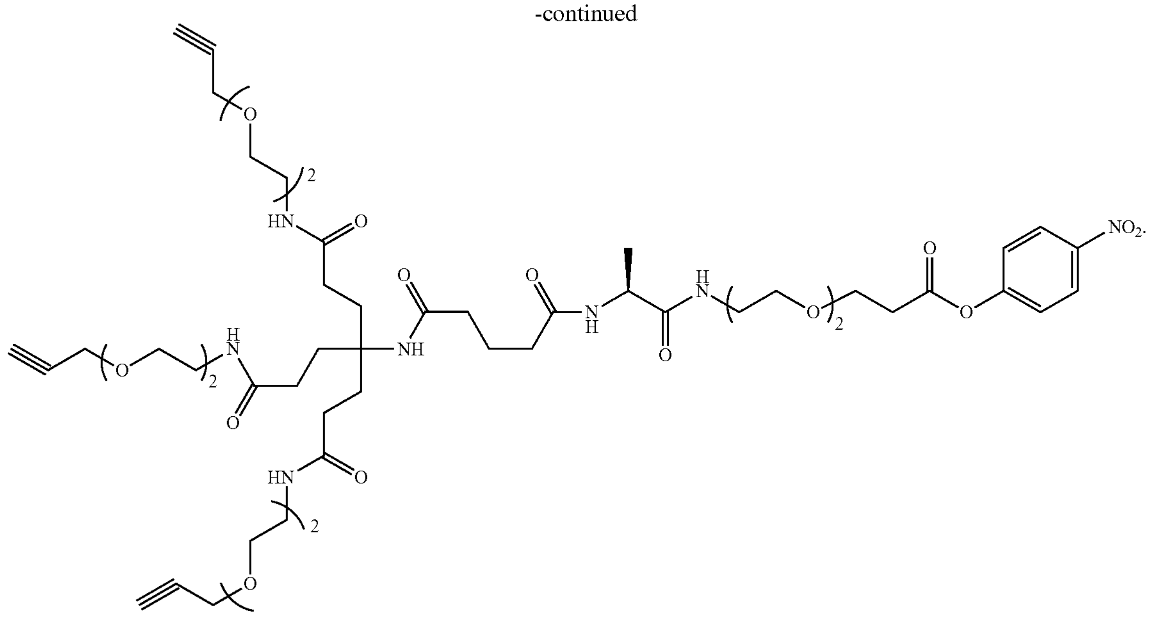

The following describes the conjugation of tri-alkyne scaffold to the annealed duplex: Amine functionalized duplex was dissolved in 90% DMSO/10% $H_2O$, at ~50-70 mg/mL. 40 eq triethylamine was added, followed by 3 eq tri-alkyne-PNP. Once complete, the conjugate was precipitated twice in a solvent system of 1× phosphate buffered saline/acetonitrile (1:14 ratio), and dried.

F. Conjugation of Integrin Targeting Ligands.

Either prior to or after annealing, the 5' or 3' tridentate alkyne functionalized sense strand is conjugated to the integrin targeting ligands. The following example describes the conjugation of αvβ3/5 integrin targeting ligands to the annealed duplex: Stock solutions of 0.5M Tris(3-hydroxypropyltriazolylmethyl)amine (THPTA), 0.5M of Cu(II) sulfate pentahydrate ($Cu(II)SO_4.5H_2O$) and 2M solution of sodium ascorbate were prepared in deionized water. A 75 mg/mL solution in DMSO of integrin targeting ligand was made. In a 1.5 mL centrifuge tube containing tri-alkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed. integrin targeting ligand was added to the reaction (6 eq/duplex, 2 eq/alkyne, ~15 μL) and the solution is vortexed. Using pH paper, pH was checked and confirmed to be pH ~8. In a separate 1.5 mL centrifuge tube, 50 μL of 0.5M THPTA was mixed with 10 uL of 0.5M $Cu(II)SO_4.5H_2$, vortexed, and incubated at room temp for κ min. After 5 min, THPTA/Cu solution (7.2 μL, 6 eq 5:1 THPTA:Cu) was added to the reaction vial, and vortexed. Immediately afterwards, 2M ascorbate (5 μL, 50 eq per duplex, 16.7 per alkyne) was added to the reaction vial and vortexed. Once the reaction was complete (typically complete in 0.5-1 h), the reaction was immediately purified by non-denaturing anion exchange chromatography.

G. Functionalization of Thiol Group on Cysteine Linker.

In some embodiments, a cysteine linker can be used to facilitate conjugation of the integrin targeting ligands to the RNAi agent. Either prior to or after annealing, the 5' or 3' tridentate alkyne-Cys(Stbu)-$PEG_2$ functionalized sense strand is functionalized with a maleimide-containing moiety, or can be reduced and left as the free thiol, as shown in the following structure:

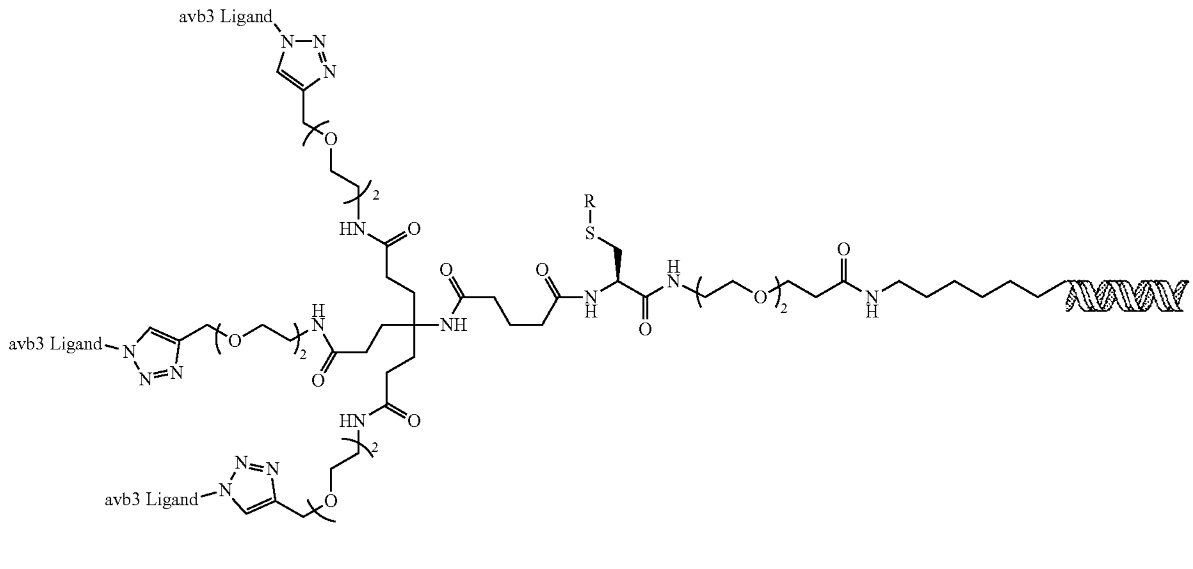

-continued

R = H or 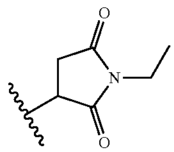

The following example describes the modification of the tri-alkyne-Cys(Stbu)-PEG$_2$-duplex with N-ethyl maleimide: Tri-alkyne-Cys(Stbu)-PEG$_2$-duplex (35 mg) was dissolved in 500 μL deionized $H_2O$. HEPES buffer (1M, pH 8.5, 82 μL), was added to the reaction, and the solution was vortexed. A solution of 1 M Dithiothreitol (DTT, 100 eq, 236 μL) was added and the solution was placed on a vortex shaker for 3 h. After confirmation of reduction of the disulfide by denaturing RP-HPLC, the conjugate was precipitated three times in a solvent system of 1× phosphate buffered saline/acetonitrile (1:14 ratio). The precipitated pellet was reconstituted in 0.5 mL of 0.1 M HEPES, pH 6.5, and N-ethyl maleimide (3 mg, 10 eq) was added to the solution, and placed on a vortex mixer for −15 min. After completion of the reaction, the conjugate was precipitated three times in a solvent system of 1× phosphate buffered saline/acetonitrile (1:14 ratio), desalted, and dried.

Example 3. Kidney Tumor Bearing Mouse Model (Orthotopic Xenograft)

Creation of SEAP-Expressing Clear Cell Renal Cell Carcinoma (ccRCC) A498 Cells.

A pCR3.1 expression vector expressing the reporter gene secreted alkaline phosphatase (SEAP) under the CMV promoter was prepared by directional cloning of the SEAP coding sequence PCR amplified from Clontech's pSEAP2-basic vector. Convenient restriction sites were added onto primers used to amplify the SEAP coding sequence for cloning into the pCR3.1 vector (Invitrogen). The resultant construct pCR3-SEAP was used to create a SEAP-expressing A498 ccRCC cell line. Briefly, pCR3-SEAP plasmid was transfected into A498 ccRCC cells by electroporation following manufacturer's recommendation. Stable transfectants were selected by G418 resistance. Selected A498-SEAP clones were evaluated for SEAP expression and integration stability.

Implantation of SEAP-Expressing Clear Cell Renal Cell Carcinoma (ccRCC) A498 Cells.

Female athymic nude mice were anesthetized with 3% isoflourane and placed in the right lateral decubitus position. A small, 0.5-1 cm, longitudinally abdominal incision in the left flank was made. Using a moist cotton swab, the left kidney was lifted out of the peritoneum and gently stabilized. Just before injection, a 1.0 ml syringe was filled with the cell/Matrigel mixture and a 27 gauge needle catheter was attached to the syringe tip. The filled syringe was then attached to a syringe pump (Harvard Apparatus, model PHD2000) and primed to remove air. The tip of a 27-gauge needle catheter attached to a syringe was inserted just below the renal capsule near the caudal pole and the tip of the needle was then carefully advanced cranially along the capsule 3-4 mm. A 10 μl aliquot of 2:1 (vol:vol) cell/Matrigel® mixture containing about 300,000 cells was slowly injected into the kidney parenchyma using a syringe pump. The needle was left in the kidney for 15-20 seconds to ensure the injection was complete. The needle was then removed from the kidney and a cotton swab was placed over the injection site for 30 seconds to prevent leakage of the cells or bleeding. The kidney was then gently placed back into the abdomen and the abdominal wall was closed. Serum was collected every 7-14 days after implantation to monitor tumor growth using a commercial SEAP assay kit. For most studies, tumor mice were used 5-6 weeks after implantation, when tumor measurements were typically around 4-8 mm.

Determination of HIF2 mRNA Expression.

For the studies reported in the Examples herein, mice were euthanized the identified day after injection and total RNA was isolated from kidney tumor using Trizol reagent following manufacturer's recommendation. Relative HiF2α mRNA levels were determined by RT-qPCR as described below and compared to mice treated with delivery buffer (isotonic glucose) only.

In preparation for quantitative PCR, total RNA was isolated from tissue samples homogenized in TriReagent (Molecular Research Center, Cincinnati, OH) following the manufacturer's protocol. Approximately 500 ng RNA was reverse-transcribed using the High Capacity cDNA Reverse Transcription Kit (Life Technologies). For human (tumor) Hif2α (EPAS1) expression, pre-manufactured TaqMan gene expression assays for human Hif2a (Catalog #4331182) and CycA (PPIA) Catalog #: 4326316E) were used in biplex reactions in triplicate using TaqMan Gene Expression Master Mix (Life Technologies) or VeriQuest Probe Master Mix (Affymetrix). Quantitative PCR was performed by using a 7500 Fast or StepOnePlus Real-Time PCR system (Life Technologies). The $\Delta\Delta C_T$ method was used to calculate relative gene expression.

Example 4. In Vivo Administration of Integrin Targeting Ligands Conjugated to RNAi Agents Targeting HIF-2 Alpha in Kidney Tumor Bearing Mice RNAi agents that included a sense strand and an antisense strand synthesized according to phosphoramidite technology on solid phase in accordance with general procedures known in the art and commonly used in oligonucleotide synthesis, as set forth in Example 2 herein. The RNAi agents were designed target Hif2α (EPAS1), and were comprised of modified nucleotides and more than one non-phosphodiester linkage.

On study day 1, kidney tumor bearing mice (see Example 4) were dosed via tail vein injection according to the following dosing Groups:

TABLE 1

Dosing Groups of Mice in Example 4.

| Group | RNAi Agent and Dose | Dosing Regimen |
|---|---|---|
| 1 | Isotonic glucose (d5w (5% dextrose in water)) (no RNAi agent) | Single injection on day 1 |
| 4 | 7.5 mg/kg of Hif2α RNAi agent (AD04546) conjugated to a tridentate integrin targeting ligand of Structure 4.1a, and further including a 40 kDa PEG moiety linked to the construct, formulated in isotonic glucose. | Single injection on day 1 |
| 5 | 7.5 mg/kg of Hif2α RNAi agent (AD04546) conjugated to a tridentate integrin targeting ligand of Structure 4.3a, and further including a 40 kDa PEG moiety linked to the construct, formulated in isotonic glucose. | Single injection on day 1 |

The RNAi agents were synthesized having nucleotide sequences directed to target the human Hif2α gene, and included a functionalized amine reactive group ($NH_2$—$C_6$) at the 5' terminal end of the sense strand to facilitate conjugation to the integrin targeting ligands.

The RNAi agents in this and other examples were synthesized having a PK modulator referred to as "20 kDA PEG moiety" or "40 kDA PEG moiety" having the structure:

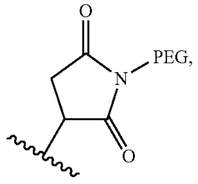

wherein  indicates the point of attachment to the RNAi agent at the C6-S— group as indicated in AD04546 (see Example 2), and PEG indicates a 20 kDa or 40 kDa PEG chain. The PK modulator was conjugated to the 3' end of the sense strand by reducing the C6-SS—C6 or 6-SS-6 group, as shown in Table A, which then underwent Michael addition with the following compound:

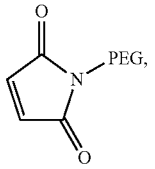

wherein PEG indicates a 20 kDa or 40 kDa PEG chain.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to GAPDH expression and expressed as fraction of vehicle control group (isotonic glucose) (geometric mean, +/−95% confidence interval), as explained in Example 3.

TABLE 2

Average Relative Hif2α mRNA Expression at Sacrifice in Example 4.

| Group ID | Average Relative huHIF2α mRNA Expression | Low (error) | High (error) |
|---|---|---|---|
| Group 1 (isotonic glucose) | 1.000 | 0.087 | 0.095 |
| Group 4 (7.5 mg/kg RNAi agent-tridentate integrin targeting ligand of Structure 4.1a, 40 kDa PEG) | 0.294 | 0.008 | 0.009 |
| Group 5 (7.5 mg/kg RNAi agent-tridentate integrin targeting ligand of Structure 4.3a, 40 kDa PEG) | 0.376 | 0.033 | 0.036 |

As shown in Table 2 above, each of the Hif2α RNAi agent-integrin targeting ligand conjugates showed a reduction in mRNA expression in mice compared to control. For example, Group 4, which included a dose of 7.5 mg/kg RNAi agent conjugated to the tridentate integrin targeting ligand of Structure 4.1a, showed approximately 71% knockdown of Hif2α mRNA (0.294).

Example 5. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 3) were dosed via tail vein injection according to the following dosing Groups:

TABLE 3

Dosing Groups of Mice in Example 5.

| Group | RNAi Agent and Dose | Dosing Regimen |
|---|---|---|
| 1 | Isotonic glucose (d5w (5% dextrose in water)) (no RNAi agent) | Single injection on day 1 |
| 3 | 7.5 mg/kg of Hif2α RNAi agent (AD04546) conjugated to a tridentate integrin targeting group having three integrin targeting ligands of Structure 4.1a, and further including a 40 kDa PEG moiety linked to the construct, formulated in isotonic glucose. | Single injection on day 1 |
| 4 | 7.5 mg/kg of Hif2α RNAi agent (AD05614) conjugated to a tridentate integrin targeting group having three integrin targeting ligands of Structure 4.1a, and further including a 40 kDa PEG moiety linked to the construct, formulated in isotonic glucose. | Single injection on day 1 |
| 5 | 7.5 mg/kg of Hif2α RNAi agent (AD05615) conjugated to a tridentate integrin targeting group having three integrin targeting ligands of Structure 4.1a, and further including a 40 kDa PEG moiety linked to the construct, formulated in isotonic glucose. | Single injection on day 1 |
| 6 | 7.5 mg/kg of Hif2α RNAi agent (AD05616) conjugated to a tridentate integrin targeting group having three integrin targeting ligands of Structure 4.1a, and further including a 40 kDa PEG moiety linked to the construct, formulated in isotonic glucose. | Single injection on day 1 |

TABLE 3-continued

Dosing Groups of Mice in Example 5.

| Group | RNAi Agent and Dose | Dosing Regimen |
|---|---|---|
| 7 | 7.5 mg/kg of Hif2α RNAi agent (AD05617) conjugated to a tridentate integrin targeting group having three integrin targeting ligands of Structure 4.1a, and further including a 40 kDa PEG moiety linked to the construct, formulated in isotonic glucose. | Single injection on day 1 |
| 8 | 7.5 mg/kg of Hif2α RNAi agent (AD05614) conjugated to a tridentate integrin targeting group having three integrin targeting ligands of Structure 4.5a, and further including a 40 kDa PEG moiety linked to the construct, formulated in isotonic glucose. | Single injection on day 1 |
| 9 | 7.5 mg/kg of Hif2α RNAi agent (AD05614) conjugated to a tridentate integrin targeting group having three integrin targeting ligands of Structure 4.6a, and further including a 40 kDa PEG moiety linked to the construct, formulated in isotonic glucose. | Single injection on day 1 |
| 10 | 7.5 mg/kg of Hif2α RNAi agent (AD05620) conjugated to a tridentate integrin targeting group having three integrin targeting ligands of Structure 4.5a, and further including a 40 kDa PEG moiety linked to the construct, formulated in isotonic glucose. | Single injection on day 1 |
| 11 | 7.5 mg/kg of Hif2α RNAi agent (AD04546) conjugated to a tridentate integrin targeting group having three integrin targeting ligands of Structure 4.4a, and further including a 40 kDa PEG moiety linked to the construct, formulated in isotonic glucose. | Single injection on day 1 |

The RNAi agents were synthesized having nucleotide sequences directed to target the human Hif2α gene, and certain groups included a functionalized amine reactive group ($NH_2$—$C_6$) at the 5' terminal end of the sense strand to facilitate conjugation to the integrin targeting ligands, while other groups included a trialkyne group at the 5' terminal end of the sense strand to facilitate conjugation to the integrin targeting ligands. The RNAi agents were synthesized having a 40 kDa PEG moiety linked to the 3' terminal end as a PK enhancer.

Three (3) tumor bearing mice were dosed in each Group (n=3). Mice were sacrificed on study day 8 after injection, and total RNA was isolated from kidney tumor according to the procedure set forth in Example 4. Relative Human HIF2a mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 3.

TABLE 4

Average Relative Hif2α mRNA Expression at Sacrifice in Example 6.

| Group ID | Average Relative huHIF2α mRNA Expression | Low (error) | High (error) |
|---|---|---|---|
| Group 1 (isotonic glucose) | 1.000 | 0.113 | 0.128 |
| Group 3 (7.5 mg/kg RNAi agent AD04546-tridentate integrin targeting ligand of Structure 4.1a, PEG 40 kDa) | 0.377 | 0.071 | 0.087 |
| Group 4 (7.5 mg/kg RNAi agent AD05614-tridentate integrin targeting ligand of Structure 4.1a, PEG 40 kDa) | 0.357 | 0.028 | 0.030 |
| Group 5 (7.5 mg/kg RNAi agent AD05615-tridentate integrin targeting ligand of Structure 4.1a, PEG 40 kDa) | 0.369 | 0.029 | 0.032 |

TABLE 4-continued

Average Relative Hif2α mRNA Expression at Sacrifice in Example 6.

| Group ID | Average Relative huHIF2α mRNA Expression | Low (error) | High (error) |
|---|---|---|---|
| Group 6 (7.5 mg/kg RNAi agent AD05616-tridentate integrin targeting ligand of Structure 4.1a, PEG 40 kDa) | 0.290 | 0.035 | 0.039 |
| Group 7 (7.5 mg/kg RNAi agent AD05617-tridentate integrin targeting ligand of Structure 4.1a, PEG 40 kDa) | 0.348 | 0.023 | 0.025 |
| Group 8 (7.5 mg/kg RNAi agent AD05614-tridentate integrin targeting ligand of Structure 4.5a, PEG 40 kDa) | 0.424 | 0.034 | 0.037 |
| Group 9 (7.5 mg/kg RNAi agent AD05614-tridentate integrin targeting ligand of Structure 4.6a, PEG 40 kDa) | 0.382 | 0.033 | 0.036 |
| Group 10 (7.5 mg/kg RNAi agent AD05620-tridentate integrin targeting ligand of Structure 4.5a, PEG 40 kDa) | 0.307 | 0.053 | 0.064 |
| Group 11 (7.5 mg/kg RNAi agent AD04546-tridentate integrin targeting ligand of Structure 4.4a, PEG 40 kDa) | 0.338 | 0.033 | 0.036 |

As shown in Table 4 above, each of the Hif2α RNAi agent-integrin targeting ligand conjugates showed a reduction in mRNA expression compared to control.

Example 6. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 3) were dosed via tail vein injection according to the following dosing Groups:

TABLE 5

Dosing Groups of Mice in Example 6.

| Group | RNAi Agent and Dose | Dosing Regimen |
|---|---|---|
| 1 | Isotonic glucose (d5w (5% dextrose in water)) (no RNAi agent) | Single injection on day 1 |
| 4 | 7.5 mg/kg of Hif2α RNAi agent (AD04546) conjugated to a tridentate integrin targeting group having three integrin targeting ligands of Structure 4.8a, and further including a Mal-C18-diacid moiety linked to the construct, formulated in isotonic glucose. | Single injection on day 1 |
| 5 | 7.5 mg/kg of Hif2α RNAi agent (AD04546) conjugated to a tridentate integrin targeting group having three integrin targeting ligands of Structure 4.9a, and further including a Mal-C18-diacid moiety linked to the construct, formulated in isotonic glucose. | Single injection on day 1 |

The RNAi agents were synthesized having nucleotide sequences directed to target the human Hif2α gene, and included a functionalized amine reactive group ($NH_2$—$C_6$) at the 5' terminal end of the sense strand to facilitate conjugation to the integrin targeting ligands.

The RNAi agents were synthesized having a PD modulator referred to as "Mal-C18-diacid moiety" having the structure:

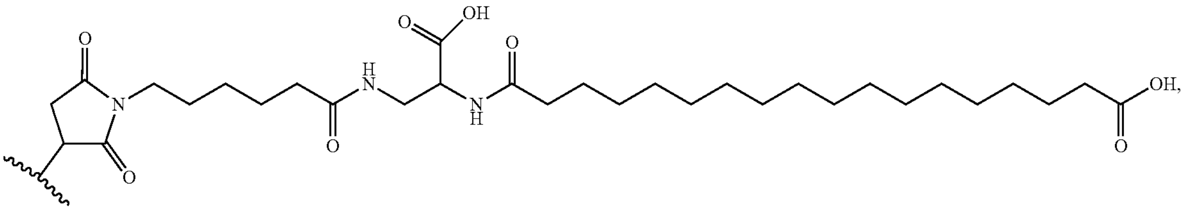 [SMILES: *C1CC(=O)N(CCCCCC(=O)NCC(NC(=O)CCCCCCCCCCCCCCCCC(=O)O)C(=O)O)C1=O]

wherein ~ indicates the point of attachment to the RNAi agent at the C6-S— group as indicated in AD04546 (see Example 2). The PD modulator was conjugated to the 3' end of the sense strand by reducing the C6-SS—C6 group, as shown in Table A, which then underwent Michael addition with the following compound:

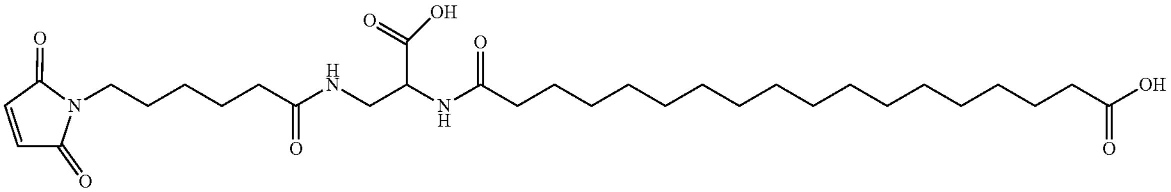 [SMILES: O=C(O)CCCCCCCCCCCCCCCCC(=O)NC(CNC(=O)CCCCCN1C(=O)C=CC1=O)C(=O)O]

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 3.

TABLE 6

Average Relative Hif2α mRNA Expression at Sacrifice in Example 6.

| Group ID | Average Relative huHIF2α mRNA Expression | Low (error) | High (error) |
|---|---|---|---|
| Group 1 (isotonic glucose) | 1.000 | 0.094 | 0.103 |
| Group 4 (7.5 mg/kg RNAi agent AD05614-tridentate integrin targeting ligand of Structure 4.8a, PEG 40 kDa) | 0.795 | 0.119 | 0.139 |
| Group 5 (7.5 mg/kg RNAi agent AD05615-tridentate integrin targeting ligand of Structure 4.9a, PEG 40 kDa) | 0.463 | 0.048 | 0.054 |

Example 7. In Vivo Administration of Integrin Targeting Ligands Conjugated to RNAi Agents Targeting HIF-2 Alpha in Kidney Tumor Bearing Mice RNAi agents that included a sense strand and an antisense strand were synthesized according to phosphoramidite technology on solid phase in accordance with general procedures known in the art and commonly used in oligonucleotide synthesis as set forth in Example 2 herein. The RNAi agents had the respective modified nucleotide sequences set forth in Example 2 herein and were designed to target Hif2α (EPAS1).

On study day 1, kidney tumor bearing mice (see Example 3) were dosed via tail vein injection according to the following dosing Groups:

TABLE 7

Dosing Groups of Mice in Example 7.

| Group | RNAi Agent and Dose | Dosing Regimen |
|---|---|---|
| 1 | Isotonic glucose (d5w (5% dextrose in water)) (no RNAi agent) | Single injection on day 1 |
| 8 | 5.0 mg/kg of HIF-2 alpha RNAi agent AD05971, linked at the 5' terminal end of the sense strand to a tridentate targeting group having three integrin targeting ligands of Structure 4.10a, with an integrin targeting ligand of Structure 4.10a linked internally at the 2' position of each of nucleotides 2, 4, 6, and 8 (3' → 5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 9 | 5.0 mg/kg of HIF-2 alpha RNAi agent AD05971, linked at the 5' terminal end of the sense strand to a tridentate targeting group having three integrin targeting ligands of Structure 4.11a, with an integrin targeting ligand of Structure 4.11a linked internally at the 2' position of each of nucleotides 2, 4, 6, and 8 (3' → 5') from the first nucleotide that forms a base pair with the antisense strand[(i)], and further linked at the 3' terminal end of the sense strand to PD modulator Mal-C18-diacid, formulated in isotonic glucose. | Single injection on day 1 |
| 10 | 5.0 mg/kg of HIF-2 alpha RNAi agent AD05971, linked at the 5' terminal end of the sense strand to a tridentate targeting group having three integrin targeting ligands of Structure 4.12a, with an integrin targeting ligand of Structure 4.12a linked internally at the 2' position of each of nucleotides 2, 4, 6, and 8 (3' → 5') from the first nucleotide that forms a base pair with the antisense strand[(i)], | Single injection on day 1 |

TABLE 7-continued

| Dosing Groups of Mice in Example 7. | | |
|---|---|---|
| Group | RNAi Agent and Dose | Dosing Regimen |
| | and further linked at the 3' terminal end of the sense strand to PD modulator Mal-C18-diacid, formulated in isotonic glucose. | |
| 11 | 5.0 mg/kg of HIF-2 alpha RNAi agent AD05971, linked at the 5' terminal end of the sense strand to a tridentate targeting group having three integrin targeting ligands of Structure 4.13a, with an integrin targeting ligand of Structure 4.13a linked internally at the 2' position of each of nucleotides 2, 4, 6, and 8 (3' → 5') from the first nucleotide that forms a base pair with the antisense strand[(i)], and further linked at the 3' terminal end of the sense strand to PD modulator Mal-C18-diacid, formulated in isotonic glucose. | Single injection on day 1 |

[(i)]The avb3 targeting ligands are linked to the 2'-O-propargyl nucleotides (represented by aAlk, gAlk, and uAlk in the modified sense strand sequence), which when viewed 5' → 3' on the sense strand sequence are at nucleotides 14, 16, 18, and 20 on the sense strand.

Three (3) tumor bearing mice were dosed in each Group (n=3). Mice were sacrificed on study day 8 after injection, and total RNA was isolated from kidney tumor according to the procedure set forth in Example 4. Relative Human HIF2α mRNA expression was then quantitated by probe-based quantitative PCR (RT-qPCR), normalized to human Cyclophilin A (PPIA) expression and expressed as fraction of vehicle control group (isotonic glucose) (geometric mean, +/−95% confidence interval), as explained in Example 3.

TABLE 8

Average Relative Hif2α mRNA Expression at Sacrifice in Example 8.

| Group ID | Average Relative huHIF2α mRNA Expression | Low (error) | High (error) |
|---|---|---|---|
| Group 1 (isotonic glucose) | 1.000 | 0.083 | 0.090 |
| Group 8 (5.0 mg/kg RNAi agent-tridentate integrin targeting ligand of Structure 4.10a, three internal ligands of Structure 4.10a, and C-18-diacid PD modulator) | 0.561 | 0.036 | 0.038 |
| Group 9 (5.0 mg/kg RNAi agent-tridentate integrin targeting ligand of Structure 4.11a, three internal ligands of Structure 4.11a, and C-18-diacid PD modulator) | 0.466 | 0.070 | 0.082 |
| Group 10 (5.0 mg/kg RNAi agent-tridentate integrin targeting ligand of Structure 4.12a, three internal ligands of Structure 4.12a, and C-18-diacid) | 0.543 | 0.033 | 0.035 |
| Group 11 (5.0 mg/kg RNAi agent-tridentate integrin targeting ligand of Structure 4.13a, three internal ligands of Structure 4.13a, and C-18-diacid) | 0.556 | 0.065 | 0.073 |

As shown in Table 8 above, each of the Hif2α RNAi agent-integrin targeting ligand conjugates showed a reduction in mRNA expression in mice compared to control.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An integrin targeting ligand comprising the structure of any of the following:

(Structure 4.1a)

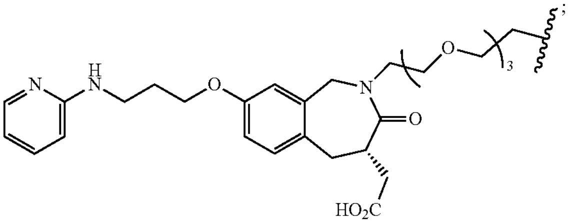

(Structure 4.2a)

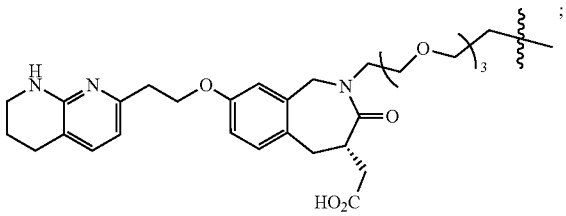

(Structure 4.3a)

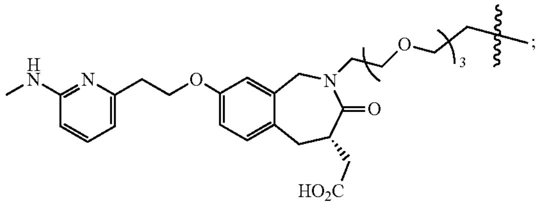

(Structure 4.4a)

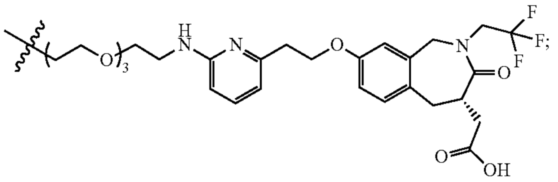

(Structure 4.5a)

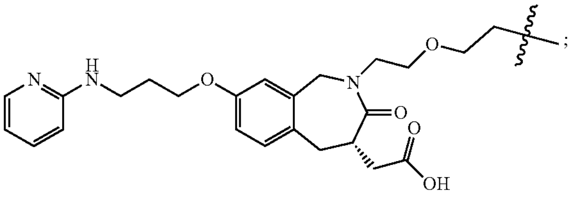

(Structure 4.6a)

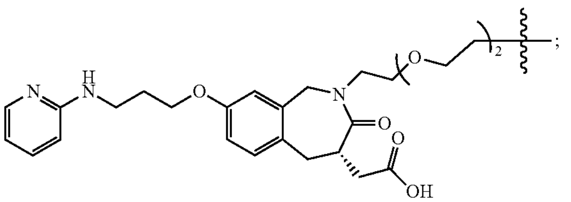

-continued (Structure 4.8a)

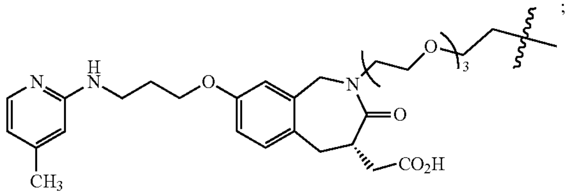

(Structure 4.9a)

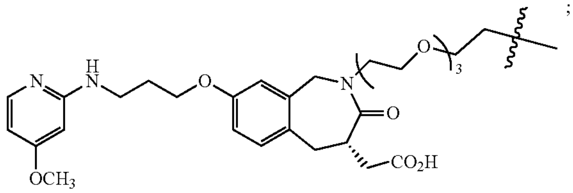

(Structure 4.10a)

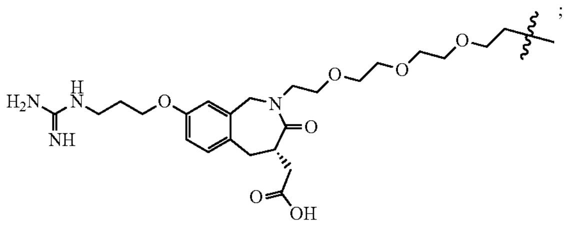

(Structure 4.11a)

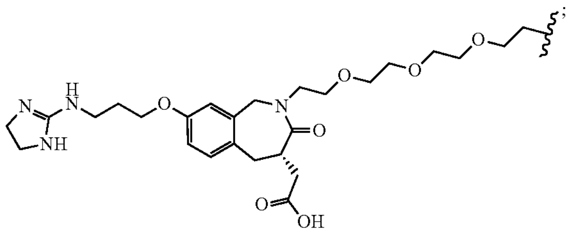

(Structrure 4.12a)

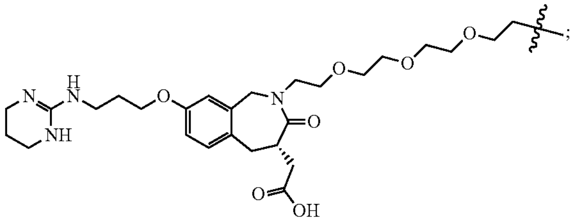

(Structure 4.13a)

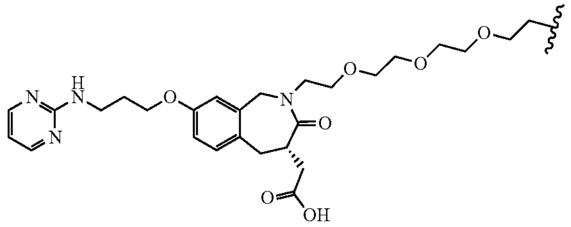

or a pharmaceutically acceptable salt thereof, wherein ⌇ indicates the point of connection to a moiety comprising a cargo molecule, wherein the cargo molecule is an RNAi agent.

2. The integrin targeting ligand of claim 1, further comprising a polyethylene glycol linker having 2-20 ethylene oxide units.

3. A composition comprising the integrin ligand of claim 1, and a pharmaceutically acceptable excipient.

4. A composition comprising the integrin ligand of claim 1, wherein the RNAi agent is capable of inhibiting the expression of a target gene in a cell expressing an integrin.

5. The composition of claim 4, wherein the integrin is integrin αvβ3, αvβ5, or both αvβ3 and αvβ5.

6. A method of delivering the RNAi agent to a cell expressing integrin αvβ3, αvβ5, or both αvβ3 and αvβ5, in a subject, the method comprising administering to the subject a composition of claim 4.

7. A method of delivering the RNAi agent to a cell or tissue of a subject in vivo, the method comprising administering to the subject a composition of claim 4.

8. A method of inhibiting the expression of a target gene in a cell that expresses integrin αvβ3, integrin αvβ5, or both integrin αvβ3 and αvβ5, in vivo, the method comprising administering to a subject an effective amount of a composition of claim 4.

9. The method of claim 8, wherein the target gene is EPAS1 (HIF2 alpha).

10. The method of claim 9, wherein the cell is a clear cell renal carcinoma tumor cell.

* * * * *